US007132268B2

(12) United States Patent
Miyake et al.

(10) Patent No.: US 7,132,268 B2
(45) Date of Patent: Nov. 7, 2006

(54) PROCESS FOR PRODUCING ISOPRENOID COMPOUNDS BY MICROORGANISMS AND A METHOD FOR SCREENING COMPOUNDS WITH ANTIBIOTIC OR WEEDING ACTIVITY

(75) Inventors: Koichiro Miyake, Hofu (JP); Shinichi Hashimoto, Sagamihara (JP); Hiroaki Motoyama, Yokohama (JP); Akio Ozaki, Machida (JP); Haruo Seto, Tokyo (JP); Tomohisa Kuzuyama, Tokyo (JP); Shunji Takahashi, Chiba (JP)

(73) Assignee: Kyowa Hakko Kogyo Co., Ltd., Tokyo (JP)

( * ) Notice: Subject to any disclaimer, the term of this patent is extended or adjusted under 35 U.S.C. 154(b) by 0 days.

(21) Appl. No.: 10/938,613

(22) Filed: Sep. 13, 2004

(65) Prior Publication Data
US 2005/0032169 A1 Feb. 10, 2005

Related U.S. Application Data

(62) Division of application No. 09/673,198, filed as application No. PCT/JP99/01987 on Apr. 14, 1999, now Pat. No. 6,806,076.

(30) Foreign Application Priority Data

| Apr. 14, 1998 | (JP) | ................. 10-103101 |
| Aug. 5, 1998 | (JP) | ................. 10-221910 |
| Feb. 15, 1999 | (JP) | ................. 11-035739 |

(51) Int. Cl.
*C12P 5/00* (2006.01)
*C12N 9/02* (2006.01)

(52) U.S. Cl. ............. 435/166; 435/167; 435/183; 435/189; 435/252.3; 435/320.1; 536/23.2

(58) Field of Classification Search ............. 435/166, 435/167, 183, 252.3, 320.1, 189, 233; 536/23.2
See application file for complete search history.

(56) References Cited

U.S. PATENT DOCUMENTS 6,465,225 B1 10/2002 Fuhr et al. .......... 210/198

FOREIGN PATENT DOCUMENTS

| AU | 752714 | 1/2000 |
| AU | 757440 | 2/2000 |
| DE | 298 00 547 | 4/1999 |
| WO | WO 00/17233 | 3/1930 |
| WO | WO 97/43437 | 11/1997 |
| WO | WO 00/00816 | 1/2000 |
| WO | WO 00/08169 | 2/2000 |
| WO | WO 00/34448 | 6/2000 |
| WO | WO 00/42205 | 7/2000 |
| WO | WO 00/44912 | 8/2000 |

OTHER PUBLICATIONS

Proc. Natl. Acad. Sci., USA, vol. 56 (1966), pp. 1586-1593.
Rohmer, et al., "Isoprenoid biosynthesis in bacteria: a novel pathway for the early steps leading to isopentenyl diphosphate", *Biochem. J.*, vol. 295 (1993), pp. 517-524.
Sprenger, et al., "Identification of a thiamin-dependent synthase in *Escherichia coli* required for . . . ", *Proc. Natl. Acad. Sci.*, USA, vol. 94 (1997), pp. 12857-12862.
Fujisaki, et al., "Cloning and Nucleotide Sequence of the ispA Gene Responsible for . . . ", *J. Biochem.*, vol. 108 (1990), pp. 995-1000.
Blattner, et al., "The Complete Genome Sequence of *Escherichia coli* K-12", *Science*, vol. 277 (1997), pp. 1453-1462.
Yamanaka, et al., "Identification and Characterization of the *smbA* Gene, a Suppressor of the . . . ", *Journal of Bacteriology*, vol. 174, No. 23 (1992), pp. 7517-7526.
Database Accession No. AX032992 (XP-002227808).
Database Accession No. AAX77621 and AAY08880 (XP-002227806).
Database Accession No. AE000148 (XP-002227803).
Database Accession No. AF035440.1 (XP-002227804).
Database Accession No. AAZ88977 (XP-002227807).
Elson, et al., "The Chemoprevention of Cancer by Mevalonate-Derived . . . ", Journal of Nutrition, vol. 124, No. 5 (1994), pp. 607-614.
Harker, et al., "Expression of prokaryotic 1-deoxy-D-xylulose-5-phosphatases in . . . ", FEBS, vol. 448, No. 1 (1999), pp. 115-119.
Lange, et al., "A family of transketolases that directs isoprenoid biosynthesis . . . ", Proc. Natl. Aca. Sci USA, vol. 95 (1998) pp. 2100-2104.
Database EMBL 'Online!, "*Escherichia coli* genomic DNA", Database Accession No. D83536 XP-002286672, position 3045-4238 (Mar. 8, 1996).
Database EMBL 'Online!, "A 1-deoxy-D-xylolose 5-phosphate reductoisomerase catalyzing the formation of 2-C-methyl-D-erythritol . . . ", Database Accession No. P45568, XP-002286673 (Nov. 1, 1995).
Kuroda, et al., "Studies of New Phosphonic Acid Antibiotics", *The Journal of Antibiotics*, vol. 33, No. 1 (1980), pp. 29-35.
Lois, et al., "Cloning and characterization of a gene from *Escherichia coli* encoding a transketolase-like enzyme . . . ", *Proc. Natl. Adam. Sci.*, vol. 95 (1998), pp. 2105-2110.

(Continued)

Primary Examiner—Tekchand Saidha
(74) Attorney, Agent, or Firm—Fitzpatrick, Cella, Harper & Scinto

(57) ABSTRACT

The present invention provides a process for producing isoprenoid compounds or proteins encoded by DNA using DNA that contains one or more of the DNA encoding proteins having activity to improve efficiency in the biosynthesis of isoprenoid compounds effective in pharmaceuticals for cardiac diseases, osteoporosis, homeostasis, prevention of cancer, and immunopotentiation, health food and antifouling paint products against barnacles; the DNA; the protein; and a method for screening a substance with antibiotic and weeding activities comprising screening a substance inhibiting enzymatic reaction on the non-mevalonate pathway.

8 Claims, 2 Drawing Sheets

OTHER PUBLICATIONS

Youvan, et al., "Nucleotide and Deduced Polypeptide Sequences of the Photosynthetic . . . ", Cell, vol. 37, No. 3 (1984), pp. 949-957.

Database EMBL 'Online!, "1-deoxy-D-xylulose 5-phosphate synthase . . . ", Database Accession No. P26242, XP-002286674 (May 1, 1992).

Database EMBL 'Online!, "R.capsulatus complete photosynthesis . . . ", Database Accession No. Z11165 XP-002286675 (Nov. 12, 1991).

Kazuyama, et al., "Fosmidomycin, a Specific Inhibitor of 1-Deoxy-D-Xylulose 5-Phosphate . . . ", Tetrahedron Letters, vol. 39, No. 43 (1998), pp. 7913-7916.

```
                              SEQUENCE LISTING

<160> NUMBER OF SEQ ID NOS: 34

<210> SEQ ID NO 1
<211> LENGTH: 620
<212> TYPE: PRT
<213> ORGANISM: Escherichia coli

<400> SEQUENCE: 1

Met Ser Phe Asp Ile Ala Lys Tyr Pro Thr Leu Ala Leu Val Asp Ser
  1               5                  10                  15

Thr Gln Glu Leu Arg Leu Leu Pro Lys Glu Ser Leu Pro Lys Leu Cys
             20                  25                  30

Asp Glu Leu Arg Arg Tyr Leu Leu Asp Ser Val Ser Arg Ser Ser Gly
         35                  40                  45

His Phe Ala Ser Gly Leu Gly Thr Val Glu Leu Thr Val Ala Leu His
     50                  55                  60
```

-continued

```
Tyr Val Tyr Asn Thr Pro Phe Asp Gln Leu Ile Trp Asp Val Gly His
 65                  70                  75                  80

Gln Ala Tyr Pro His Lys Ile Leu Thr Gly Arg Arg Asp Lys Ile Gly
                 85                  90                  95

Thr Ile Arg Gln Lys Gly Gly Leu His Pro Phe Pro Trp Arg Gly Glu
            100                 105                 110

Ser Glu Tyr Asp Val Leu Ser Val Gly His Ser Ser Thr Ser Ile Ser
        115                 120                 125

Ala Gly Ile Gly Ile Ala Val Ala Ala Glu Lys Glu Gly Lys Asn Arg
    130                 135                 140

Arg Thr Val Cys Val Ile Gly Asp Gly Ala Ile Thr Ala Gly Met Ala
145                 150                 155                 160

Phe Glu Ala Met Asn His Ala Gly Asp Ile Arg Pro Asp Met Leu Val
                165                 170                 175

Ile Leu Asn Asp Asn Glu Met Ser Ile Ser Glu Asn Val Gly Ala Leu
            180                 185                 190

Asn Asn His Leu Ala Gln Leu Leu Ser Gly Lys Leu Tyr Ser Ser Leu
        195                 200                 205

Arg Glu Gly Gly Lys Lys Val Phe Ser Gly Val Pro Pro Ile Lys Glu
    210                 215                 220

Leu Leu Lys Arg Thr Glu Glu His Ile Lys Gly Met Val Val Pro Gly
225                 230                 235                 240

Thr Leu Phe Glu Glu Leu Gly Phe Asn Tyr Ile Gly Pro Val Asp Gly
                245                 250                 255

His Asp Val Leu Gly Leu Ile Thr Thr Leu Lys Asn Met Arg Asp Leu
            260                 265                 270

Lys Gly Pro Gln Phe Leu His Ile Met Thr Lys Lys Gly Arg Gly Tyr
        275                 280                 285

Glu Pro Ala Glu Lys Asp Pro Ile Thr Phe His Ala Val Pro Lys Phe
    290                 295                 300

Asp Pro Ser Ser Gly Cys Leu Pro Lys Ser Ser Gly Gly Leu Pro Ser
305                 310                 315                 320

Tyr Ser Lys Ile Phe Gly Asp Trp Leu Cys Glu Thr Ala Ala Lys Asp
                325                 330                 335

Asn Lys Leu Met Ala Ile Thr Pro Ala Met Arg Glu Gly Ser Gly Met
            340                 345                 350

Val Glu Phe Ser Arg Lys Phe Pro Asp Arg Tyr Phe Asp Val Ala Ile
        355                 360                 365

Ala Glu Gln His Ala Val Thr Phe Ala Ala Gly Leu Ala Ile Gly Gly
    370                 375                 380

Tyr Lys Pro Ile Val Ala Ile Tyr Ser Thr Phe Leu Gln Arg Ala Tyr
385                 390                 395                 400

Asp Gln Val Leu His Asp Val Ala Ile Gln Lys Leu Pro Val Leu Phe
                405                 410                 415

Ala Ile Asp Arg Ala Gly Ile Val Gly Ala Asp Gly Gln Thr His Gln
            420                 425                 430

Gly Ala Phe Asp Leu Ser Tyr Leu Arg Cys Ile Pro Glu Met Val Ile
        435                 440                 445

Met Thr Pro Ser Asp Glu Asn Glu Cys Arg Gln Met Leu Tyr Thr Gly
450                 455                 460

Tyr His Tyr Asn Asp Gly Pro Ser Ala Val Arg Tyr Pro Arg Gly Asn
465                 470                 475                 480

Ala Val Gly Val Glu Leu Thr Pro Leu Glu Lys Leu Pro Ile Gly Lys
```

```
                       485                 490                 495
Gly Ile Val Lys Arg Arg Gly Glu Lys Leu Ala Ile Leu Asn Phe Gly
                500                 505                 510

Thr Leu Met Pro Glu Ala Ala Lys Val Ala Glu Ser Leu Asn Ala Thr
            515                 520                 525

Leu Val Asp Met Arg Phe Val Lys Pro Leu Asp Glu Ala Leu Ile Leu
        530                 535                 540

Glu Met Ala Ala Ser His Glu Ala Leu Val Thr Val Glu Glu Asn Ala
545                 550                 555                 560

Ile Met Gly Gly Ala Gly Ser Gly Val Asn Glu Val Leu Met Ala His
                565                 570                 575

Arg Lys Pro Val Pro Val Leu Asn Ile Gly Leu Pro Asp Phe Phe Ile
            580                 585                 590

Pro Gln Gly Thr Gln Glu Met Arg Ala Glu Leu Gly Leu Asp Ala
        595                 600                 605

Ala Gly Met Glu Ala Lys Ile Lys Ala Trp Leu Ala
    610                 615                 620

<210> SEQ ID NO 2
<211> LENGTH: 299
<212> TYPE: PRT
<213> ORGANISM: Escherichia coli

<400> SEQUENCE: 2

Met Asp Phe Pro Gln Gln Leu Glu Ala Cys Val Lys Gln Ala Asn Gln
1               5                   10                  15

Ala Leu Ser Arg Phe Ile Ala Pro Leu Pro Phe Gln Asn Thr Pro Val
            20                  25                  30

Val Glu Thr Met Gln Tyr Gly Ala Leu Leu Gly Gly Lys Arg Leu Arg
        35                  40                  45

Pro Phe Leu Val Tyr Ala Thr Gly His Met Phe Gly Val Ser Thr Asn
    50                  55                  60

Thr Leu Asp Ala Pro Ala Ala Ala Val Glu Cys Ile His Ala Tyr Ser
65                  70                  75                  80

Leu Ile His Asp Asp Leu Pro Ala Met Asp Asp Asp Leu Arg Arg
                85                  90                  95

Gly Leu Pro Thr Cys His Val Lys Phe Gly Glu Ala Asn Ala Ile Leu
            100                 105                 110

Ala Gly Asp Ala Leu Gln Thr Leu Ala Phe Ser Ile Leu Ser Asp Ala
        115                 120                 125

Asp Met Pro Glu Val Ser Asp Arg Asp Arg Ile Ser Met Ile Ser Glu
    130                 135                 140

Leu Ala Ser Ala Ser Gly Ile Ala Gly Met Cys Gly Gly Gln Ala Leu
145                 150                 155                 160

Asp Leu Asp Ala Glu Gly Lys His Val Pro Leu Asp Ala Leu Glu Arg
                165                 170                 175

Ile His Arg His Lys Thr Gly Ala Leu Ile Arg Ala Ala Val Arg Leu
            180                 185                 190

Gly Ala Leu Ser Ala Gly Asp Lys Gly Arg Arg Ala Leu Pro Val Leu
        195                 200                 205

Asp Lys Tyr Ala Glu Ser Ile Gly Leu Ala Phe Gln Val Gln Asp Asp
    210                 215                 220

Ile Leu Asp Val Val Gly Asp Thr Ala Thr Leu Gly Lys Arg Gln Gly
225                 230                 235                 240
```

```
Ala Asp Gln Gln Leu Gly Lys Ser Thr Tyr Pro Ala Leu Leu Gly Leu
            245                 250                 255

Glu Gln Ala Arg Lys Ala Arg Asp Leu Ile Asp Asp Ala Arg Gln
        260                 265                 270

Ser Leu Lys Gln Leu Ala Glu Gln Ser Leu Asp Thr Ser Ala Leu Glu
        275                 280                 285

Ala Leu Ala Asp Tyr Ile Ile Gln Arg Asn Lys
        290                 295

<210> SEQ ID NO 3
<211> LENGTH: 80
<212> TYPE: PRT
<213> ORGANISM: Escherichia coli

<400> SEQUENCE: 3

Met Pro Lys Lys Asn Glu Ala Pro Ala Ser Phe Glu Lys Ala Leu Ser
 1               5                  10                  15

Glu Leu Glu Gln Ile Val Thr Arg Leu Glu Ser Gly Asp Leu Pro Leu
            20                  25                  30

Glu Glu Ala Leu Asn Glu Phe Glu Arg Gly Val Gln Leu Ala Arg Gln
        35                  40                  45

Gly Gln Ala Lys Leu Gln Gln Ala Glu Gln Arg Val Gln Ile Leu Leu
    50                  55                  60

Ser Asp Asn Glu Asp Ala Ser Leu Thr Pro Phe Thr Pro Asp Asn Glu
65                  70                  75                  80

<210> SEQ ID NO 4
<211> LENGTH: 348
<212> TYPE: PRT
<213> ORGANISM: Escherichia coli

<400> SEQUENCE: 4

Val Thr Gly Val Asn Glu Cys Ser Arg Ser Thr Cys Asn Leu Lys Tyr
 1               5                  10                  15

Asp Glu Tyr Ser Arg Ser Gly Ser Met Gln Tyr Asn Pro Leu Gly Lys
            20                  25                  30

Thr Asp Leu Arg Val Ser Arg Leu Cys Leu Gly Cys Met Thr Phe Gly
        35                  40                  45

Glu Pro Asp Arg Gly Asn His Ala Trp Thr Leu Pro Glu Glu Ser Ser
    50                  55                  60

Arg Pro Ile Ile Lys Arg Ala Leu Glu Gly Gly Ile Asn Phe Phe Asp
65                  70                  75                  80

Thr Ala Asn Ser Tyr Ser Asp Gly Ser Ser Glu Glu Ile Val Gly Arg
                85                  90                  95

Ala Leu Arg Asp Phe Ala Arg Arg Glu Asp Val Val Ala Thr Lys
            100                 105                 110

Val Phe His Arg Val Gly Asp Leu Pro Glu Gly Leu Ser Arg Ala Gln
        115                 120                 125

Ile Leu Arg Ser Ile Asp Asp Ser Leu Arg Arg Leu Gly Met Asp Tyr
    130                 135                 140

Val Asp Ile Leu Gln Ile His Arg Trp Asp Tyr Asn Thr Pro Ile Glu
145                 150                 155                 160

Glu Thr Leu Glu Ala Leu Asn Asp Val Val Lys Ala Gly Lys Ala Arg
                165                 170                 175

Tyr Ile Gly Ala Ser Ser Met His Ala Ser Gln Phe Ala Gln Ala Leu
            180                 185                 190
```

-continued

```
Glu Leu Gln Lys Gln His Gly Trp Ala Gln Phe Val Ser Met Gln Asp
            195                 200                 205

His Tyr Asn Leu Ile Tyr Arg Glu Glu Arg Glu Met Leu Pro Leu
    210                 215                 220

Cys Tyr Gln Glu Gly Val Ala Val Ile Pro Trp Ser Pro Leu Ala Arg
225                 230                 235                 240

Gly Arg Leu Thr Arg Pro Trp Gly Glu Thr Thr Ala Arg Leu Val Ser
                245                 250                 255

Asp Glu Val Gly Lys Asn Leu Tyr Lys Glu Ser Asp Glu Asn Asp Ala
            260                 265                 270

Gln Ile Ala Glu Arg Leu Thr Gly Val Ser Glu Glu Leu Gly Ala Thr
        275                 280                 285

Arg Ala Gln Val Ala Leu Ala Trp Leu Leu Ser Lys Pro Gly Ile Ala
    290                 295                 300

Ala Pro Ile Ile Gly Thr Ser Arg Glu Glu Gln Leu Asp Glu Leu Leu
305                 310                 315                 320

Asn Ala Val Asp Ile Thr Leu Lys Pro Glu Gln Ile Ala Glu Leu Glu
                325                 330                 335

Thr Pro Tyr Lys Pro His Pro Val Gly Phe Lys
                340                 345

<210> SEQ ID NO 5
<211> LENGTH: 398
<212> TYPE: PRT
<213> ORGANISM: Escherichia coli

<400> SEQUENCE: 5

Met Lys Gln Leu Thr Ile Leu Gly Ser Thr Gly Ser Ile Gly Cys Ser
1               5                   10                  15

Thr Leu Asp Val Val Arg His Asn Pro Glu His Phe Arg Val Val Ala
                20                  25                  30

Leu Val Ala Gly Lys Asn Val Thr Arg Met Val Glu Gln Cys Leu Glu
            35                  40                  45

Phe Ser Pro Arg Tyr Ala Val Met Asp Asp Glu Ala Ser Ala Lys Leu
        50                  55                  60

Leu Lys Thr Met Leu Gln Gln Gln Gly Ser Arg Thr Glu Val Leu Ser
65                  70                  75                  80

Gly Gln Gln Ala Ala Cys Asp Met Ala Ala Leu Glu Asp Val Asp Gln
                85                  90                  95

Val Met Ala Ala Ile Val Gly Ala Ala Gly Leu Leu Pro Thr Leu Ala
            100                 105                 110

Ala Ile Arg Ala Gly Lys Thr Ile Leu Leu Ala Asn Lys Glu Ser Leu
        115                 120                 125

Val Thr Cys Gly Arg Leu Phe Met Asp Ala Val Lys Gln Ser Lys Ala
130                 135                 140

Gln Leu Leu Pro Val Asp Ser Glu His Asn Ala Ile Phe Gln Ser Leu
145                 150                 155                 160

Pro Gln Pro Ile Gln His Asn Leu Gly Tyr Ala Asp Leu Glu Gln Asn
                165                 170                 175

Gly Val Val Ser Ile Leu Leu Thr Gly Ser Gly Gly Pro Phe Arg Glu
            180                 185                 190

Thr Pro Leu Arg Asp Leu Ala Thr Met Thr Pro Asp Gln Ala Cys Arg
        195                 200                 205

His Pro Asn Trp Ser Met Gly Arg Lys Ile Ser Val Asp Ser Ala Thr
    210                 215                 220
```

```
Met Met Asn Lys Gly Leu Glu Tyr Ile Glu Ala Arg Trp Leu Phe Asn
225                 230                 235                 240

Ala Ser Ala Ser Gln Met Glu Val Leu Ile His Pro Gln Ser Val Ile
            245                 250                 255

His Ser Met Val Arg Tyr Gln Asp Gly Ser Val Leu Ala Gln Leu Gly
        260                 265                 270

Glu Pro Asp Met Val Arg Gln Leu Pro Thr Pro Trp Ala Trp Pro Asn
    275                 280                 285

Arg Val Asn Ser Gly Val Lys Pro Leu Asp Phe Cys Lys Leu Ser Ala
290                 295                 300

Leu Thr Phe Ala Ala Pro Asp Tyr Asp Arg Tyr Pro Cys Leu Lys Leu
305                 310                 315                 320

Ala Met Glu Ala Phe Glu Gln Gly Gln Ala Ala Thr Thr Ala Leu Asn
                325                 330                 335

Ala Ala Asn Glu Ile Thr Val Ala Ala Phe Leu Ala Gln Gln Ile Arg
            340                 345                 350

Phe Thr Asp Ile Ala Ala Leu Asn Leu Ser Val Leu Glu Lys Met Asp
        355                 360                 365

Met Arg Glu Pro Gln Cys Val Asp Asp Val Leu Ser Val Asp Ala Asn
    370                 375                 380

Ala Arg Glu Val Ala Arg Lys Glu Val Met Arg Leu Ala Ser
385                 390                 395

<210> SEQ ID NO 6
<211> LENGTH: 1860
<212> TYPE: DNA
<213> ORGANISM: Escherichia coli
<220> FEATURE:
<221> NAME/KEY: CDS
<222> LOCATION: (1)..(1860)

<400> SEQUENCE: 6 atg agt ttt gat att gcc aaa tac ccg acc ctg gca ctg gtc gac tcc        48
Met Ser Phe Asp Ile Ala Lys Tyr Pro Thr Leu Ala Leu Val Asp Ser
1               5                   10                  15 acc cag gag tta cga ctg ttg ccg aaa gag agt tta ccg aaa ctc tgc        96
Thr Gln Glu Leu Arg Leu Leu Pro Lys Glu Ser Leu Pro Lys Leu Cys
            20                  25                  30 gac gaa ctg cgc cgc tat tta ctc gac agc gtg agc cgt tcc agc ggg       144
Asp Glu Leu Arg Arg Tyr Leu Leu Asp Ser Val Ser Arg Ser Ser Gly
        35                  40                  45 cac ttc gcc tcc ggg ctg ggc acg gtc gaa ctg acc gtg gcg ctg cac       192
His Phe Ala Ser Gly Leu Gly Thr Val Glu Leu Thr Val Ala Leu His
    50                  55                  60 tat gtc tac aac acc ccg ttt gac caa ttg att tgg gat gtg ggg cat       240
Tyr Val Tyr Asn Thr Pro Phe Asp Gln Leu Ile Trp Asp Val Gly His
65                  70                  75                  80 cag gct tat ccg cat aaa att ttg acc gga cgc cgc gac aaa atc ggc       288
Gln Ala Tyr Pro His Lys Ile Leu Thr Gly Arg Arg Asp Lys Ile Gly
                85                  90                  95 acc atc cgt cag aaa ggc ggt ctg cac ccg ttc ccg tgg cgc ggc gaa       336
Thr Ile Arg Gln Lys Gly Gly Leu His Pro Phe Pro Trp Arg Gly Glu
            100                 105                 110 agc gaa tat gac gta tta agc gtc ggg cat tca tca acc tcc atc agt       384
Ser Glu Tyr Asp Val Leu Ser Val Gly His Ser Ser Thr Ser Ile Ser
        115                 120                 125 gcc gga att ggt att gcg gtt gct gcc gaa aaa gaa ggc aaa aat cgc       432
Ala Gly Ile Gly Ile Ala Val Ala Ala Glu Lys Glu Gly Lys Asn Arg
```

```
            130                 135                 140
cgc acc gtc tgt gtc att ggc gat ggc gcg att acc gca ggc atg gcg        480
Arg Thr Val Cys Val Ile Gly Asp Gly Ala Ile Thr Ala Gly Met Ala
145                 150                 155                 160 ttt gaa gcg atg aat cac gcg ggc gat atc cgt cct gat atg ctg gtg        528
Phe Glu Ala Met Asn His Ala Gly Asp Ile Arg Pro Asp Met Leu Val
                165                 170                 175 att ctc aac gac aat gaa atg tcg att tcc gaa aat gtc ggc gcg ctc        576
Ile Leu Asn Asp Asn Glu Met Ser Ile Ser Glu Asn Val Gly Ala Leu
            180                 185                 190 aac aac cat ctg gca cag ctg ctt tcc ggt aag ctt tac tct tca ctg        624
Asn Asn His Leu Ala Gln Leu Leu Ser Gly Lys Leu Tyr Ser Ser Leu
        195                 200                 205 cgc gaa ggc ggg aaa aaa gtt ttc tct ggc gtg ccg cca att aaa gag        672
Arg Glu Gly Gly Lys Lys Val Phe Ser Gly Val Pro Pro Ile Lys Glu
    210                 215                 220 ctg ctc aaa cgc acc gaa gaa cat att aaa ggc atg gta gtg cct ggc        720
Leu Leu Lys Arg Thr Glu Glu His Ile Lys Gly Met Val Val Pro Gly
225                 230                 235                 240 acg ttg ttt gaa gag ctg ggc ttt aac tac atc ggc ccg gtg gac ggt        768
Thr Leu Phe Glu Glu Leu Gly Phe Asn Tyr Ile Gly Pro Val Asp Gly
                245                 250                 255 cac gat gtg ctg ggg ctt atc acc acg cta aag aac atg cgc gac ctg        816
His Asp Val Leu Gly Leu Ile Thr Thr Leu Lys Asn Met Arg Asp Leu
            260                 265                 270 aaa ggc ccg cag ttc ctg cat atc atg acc aaa aaa ggt cgt ggt tat        864
Lys Gly Pro Gln Phe Leu His Ile Met Thr Lys Lys Gly Arg Gly Tyr
        275                 280                 285 gaa ccg gca gaa aaa gac ccg atc act ttc cac gcc gtg cct aaa ttt        912
Glu Pro Ala Glu Lys Asp Pro Ile Thr Phe His Ala Val Pro Lys Phe
    290                 295                 300 gat ccc tcc agc ggt tgt ttg ccg aaa agt agc ggc ggt ttg ccg agc        960
Asp Pro Ser Ser Gly Cys Leu Pro Lys Ser Ser Gly Gly Leu Pro Ser
305                 310                 315                 320 tat tca aaa atc ttt ggc gac tgg ttg tgc gaa acg gca gcg aaa gac       1008
Tyr Ser Lys Ile Phe Gly Asp Trp Leu Cys Glu Thr Ala Ala Lys Asp
                325                 330                 335 aac aag ctg atg gcg att act ccg gcg atg cgt gaa ggt tcc ggc atg       1056
Asn Lys Leu Met Ala Ile Thr Pro Ala Met Arg Glu Gly Ser Gly Met
            340                 345                 350 gtc gag ttt tca cgt aaa ttc ccg gat cgc tac ttc gac gtg gca att       1104
Val Glu Phe Ser Arg Lys Phe Pro Asp Arg Tyr Phe Asp Val Ala Ile
        355                 360                 365 gcc gag caa cac gcg gtg acc ttt gct gcg ggt ctg gcg att ggt ggg       1152
Ala Glu Gln His Ala Val Thr Phe Ala Ala Gly Leu Ala Ile Gly Gly
    370                 375                 380 tac aaa ccc att gtc gcg att tac tcc act ttc ctg caa cgc gcc tat       1200
Tyr Lys Pro Ile Val Ala Ile Tyr Ser Thr Phe Leu Gln Arg Ala Tyr
385                 390                 395                 400 gat cag gtg ctg cat gac gtg gcg att caa aag ctt ccg gtc ctg ttc       1248
Asp Gln Val Leu His Asp Val Ala Ile Gln Lys Leu Pro Val Leu Phe
                405                 410                 415 gcc atc gac cgc gcg ggc att gtt ggt gct gac ggt caa acc cat cag       1296
Ala Ile Asp Arg Ala Gly Ile Val Gly Ala Asp Gly Gln Thr His Gln
            420                 425                 430 ggt gct ttt gat ctc tct tac ctg cgc tgc ata ccg gaa atg gtc att       1344
Gly Ala Phe Asp Leu Ser Tyr Leu Arg Cys Ile Pro Glu Met Val Ile
        435                 440                 445 atg acc ccg agc gat gaa aac gaa tgt cgc cag atg ctc tat acc ggc       1392
Met Thr Pro Ser Asp Glu Asn Glu Cys Arg Gln Met Leu Tyr Thr Gly
```

-continued

```
Met Thr Pro Ser Asp Glu Asn Glu Cys Arg Gln Met Leu Tyr Thr Gly
        450                 455                 460 tat cac tat aac gat ggc ccg tca gcg gtg cgc tac ccg cgt ggc aac     1440
Tyr His Tyr Asn Asp Gly Pro Ser Ala Val Arg Tyr Pro Arg Gly Asn
465                 470                 475                 480 gcg gtc ggc gtg gaa ctg acg ccg ctg gaa aaa cta cca att ggc aaa     1488
Ala Val Gly Val Glu Leu Thr Pro Leu Glu Lys Leu Pro Ile Gly Lys
                485                 490                 495 ggc att gtg aag cgt cgt ggc gag aaa ctg gcg atc ctt aac ttt ggt     1536
Gly Ile Val Lys Arg Arg Gly Glu Lys Leu Ala Ile Leu Asn Phe Gly
            500                 505                 510 acg ctg atg cca gaa gcg gcg aaa gtc gcc gaa tcg ctg aac gcc acg     1584
Thr Leu Met Pro Glu Ala Ala Lys Val Ala Glu Ser Leu Asn Ala Thr
        515                 520                 525 ctg gtc gat atg cgt ttt gtg aaa ccg ctt gat gaa gcg tta att ctg     1632
Leu Val Asp Met Arg Phe Val Lys Pro Leu Asp Glu Ala Leu Ile Leu
    530                 535                 540 gaa atg gcc gcc agc cat gaa gcg ctg gtc acc gta gaa gaa aac gcc     1680
Glu Met Ala Ala Ser His Glu Ala Leu Val Thr Val Glu Glu Asn Ala
545                 550                 555                 560 att atg ggc ggc gca ggc agc ggc gtg aac gaa gtg ctg atg gcc cat     1728
Ile Met Gly Gly Ala Gly Ser Gly Val Asn Glu Val Leu Met Ala His
                565                 570                 575 cgt aaa cca gta ccc gtg ctg aac att ggc ctg ccg gac ttc ttt att     1776
Arg Lys Pro Val Pro Val Leu Asn Ile Gly Leu Pro Asp Phe Phe Ile
            580                 585                 590 ccg caa gga act cag gaa gaa atg cgc gcc gaa ctc ggc ctc gat gcc     1824
Pro Gln Gly Thr Gln Glu Glu Met Arg Ala Glu Leu Gly Leu Asp Ala
        595                 600                 605 gct ggt atg gaa gcc aaa atc aag gcc tgg ctg gca                     1860
Ala Gly Met Glu Ala Lys Ile Lys Ala Trp Leu Ala
    610                 615                 620

<210> SEQ ID NO 7
<211> LENGTH: 897
<212> TYPE: DNA
<213> ORGANISM: Escherichia coli
<220> FEATURE:
<221> NAME/KEY: CDS
<222> LOCATION: (1)..(897)

<400> SEQUENCE: 7 atg gac ttt ccg cag caa ctc gaa gcc tgc gtt aag cag gcc aac cag     48
Met Asp Phe Pro Gln Gln Leu Glu Ala Cys Val Lys Gln Ala Asn Gln
1               5                   10                  15 gcg ctg agc cgt ttt atc gcc cca ctg ccc ttt cag aac act ccc gtg     96
Ala Leu Ser Arg Phe Ile Ala Pro Leu Pro Phe Gln Asn Thr Pro Val
            20                  25                  30 gtc gaa acc atg cag tat ggc gca tta tta ggt ggt aag cgc ctg cga     144
Val Glu Thr Met Gln Tyr Gly Ala Leu Leu Gly Gly Lys Arg Leu Arg
        35                  40                  45 cct ttc ctg gtt tat gcc acc ggt cat atg ttc ggc gtt agc aca aac     192
Pro Phe Leu Val Tyr Ala Thr Gly His Met Phe Gly Val Ser Thr Asn
    50                  55                  60 acg ctg gac gca ccc gct gcc gcc gtt gag tgt atc cac gct tac tca     240
Thr Leu Asp Ala Pro Ala Ala Ala Val Glu Cys Ile His Ala Tyr Ser
65                  70                  75                  80 tta att cat gat gat tta ccg gca atg gat gat gac gat ctg cgt cgc     288
Leu Ile His Asp Asp Leu Pro Ala Met Asp Asp Asp Asp Leu Arg Arg
                85                  90                  95 ggt ttg cca acc tgc cat gtg aag ttt ggc gaa gca aac gcg att ctc     336
```

-continued

```
Gly Leu Pro Thr Cys His Val Lys Phe Gly Glu Ala Asn Ala Ile Leu
            100                 105                 110 gct ggc gac gct tta caa acg ctg gcg ttc tcg att tta agc gat gcc    384
Ala Gly Asp Ala Leu Gln Thr Leu Ala Phe Ser Ile Leu Ser Asp Ala
        115                 120                 125 gat atg ccg gaa gtg tcg gac cgc gac aga att tcg atg att tct gaa    432
Asp Met Pro Glu Val Ser Asp Arg Asp Arg Ile Ser Met Ile Ser Glu
    130                 135                 140 ctg gcg agc gcc agt ggt att gcc gga atg tgc ggt ggt cag gca tta    480
Leu Ala Ser Ala Ser Gly Ile Ala Gly Met Cys Gly Gly Gln Ala Leu
145                 150                 155                 160 gat tta gac gcg gaa ggc aaa cac gta cct ctg gac gcg ctt gag cgt    528
Asp Leu Asp Ala Glu Gly Lys His Val Pro Leu Asp Ala Leu Glu Arg
                165                 170                 175 att cat cgt cat aaa acc ggc gca ttg att cgc gcc gcc gtt cgc ctt    576
Ile His Arg His Lys Thr Gly Ala Leu Ile Arg Ala Ala Val Arg Leu
            180                 185                 190 ggt gca tta agc gcc gga gat aaa gga cgt cgt gct ctg ccg gta ctc    624
Gly Ala Leu Ser Ala Gly Asp Lys Gly Arg Arg Ala Leu Pro Val Leu
        195                 200                 205 gac aag tat gca gag agc atc ggc ctt gcc ttc cag gtt cag gat gac    672
Asp Lys Tyr Ala Glu Ser Ile Gly Leu Ala Phe Gln Val Gln Asp Asp
    210                 215                 220 atc ctg gat gtg gtg gga gat act gca acg ttg gga aaa cgc cag ggt    720
Ile Leu Asp Val Val Gly Asp Thr Ala Thr Leu Gly Lys Arg Gln Gly
225                 230                 235                 240 gcc gac cag caa ctt ggt aaa agt acc tac cct gca ctt ctg ggt ctt    768
Ala Asp Gln Gln Leu Gly Lys Ser Thr Tyr Pro Ala Leu Leu Gly Leu
                245                 250                 255 gag caa gcc cgg aag aaa gcc cgg gat ctg atc gac gat gcc cgt cag    816
Glu Gln Ala Arg Lys Lys Ala Arg Asp Leu Ile Asp Asp Ala Arg Gln
            260                 265                 270 tcg ctg aaa caa ctg gct gaa cag tca ctc gat acc tcg gca ctg gaa    864
Ser Leu Lys Gln Leu Ala Glu Gln Ser Leu Asp Thr Ser Ala Leu Glu
        275                 280                 285 gcg cta gcg gac tac atc atc cag cgt aat aaa                        897
Ala Leu Ala Asp Tyr Ile Ile Gln Arg Asn Lys
    290                 295

<210> SEQ ID NO 8
<211> LENGTH: 240
<212> TYPE: DNA
<213> ORGANISM: Escherichia coli
<220> FEATURE:
<221> NAME/KEY: CDS
<222> LOCATION: (1)..(240)

<400> SEQUENCE: 8 atg ccg aag aaa aat gag gcg ccc gcc agc ttt gaa aag gcg ctg agc     48
Met Pro Lys Lys Asn Glu Ala Pro Ala Ser Phe Glu Lys Ala Leu Ser
1               5                   10                  15 gag ctg gaa cag att gta acc cgt ctg gaa agt ggc gac ctg ccg ctg     96
Glu Leu Glu Gln Ile Val Thr Arg Leu Glu Ser Gly Asp Leu Pro Leu
            20                  25                  30 gaa gag gcg ctg aac gag ttc gaa cgc ggc gtg cag ctg gca cgt cag    144
Glu Glu Ala Leu Asn Glu Phe Glu Arg Gly Val Gln Leu Ala Arg Gln
        35                  40                  45 ggg cag gcc aaa tta caa caa gcc gaa cag cgc gta caa att ctg ctg    192
Gly Gln Ala Lys Leu Gln Gln Ala Glu Gln Arg Val Gln Ile Leu Leu
    50                  55                  60 tct gac aat gaa gac gcc tct cta acc cct ttt aca ccg gac aat gag    240
Ser Asp Asn Glu Asp Ala Ser Leu Thr Pro Phe Thr Pro Asp Asn Glu
```

```
Ser Asp Asn Glu Asp Ala Ser Leu Thr Pro Phe Thr Pro Asp Asn Glu
 65                  70                  75                  80
```

<210> SEQ ID NO 9
<211> LENGTH: 1044
<212> TYPE: DNA
<213> ORGANISM: Escherichia coli
<220> FEATURE:
<221> NAME/KEY: CDS
<222> LOCATION: (1)..(1044)

<400> SEQUENCE: 9

```
gtg act ggg gtg aac gaa tgc agc cgc agc aca tgc aac ttg aag tat      48
Val Thr Gly Val Asn Glu Cys Ser Arg Ser Thr Cys Asn Leu Lys Tyr
 1               5                  10                  15 gac gag tat agc agg agt ggc agc atg caa tac aac ccc tta gga aaa      96
Asp Glu Tyr Ser Arg Ser Gly Ser Met Gln Tyr Asn Pro Leu Gly Lys
             20                  25                  30 acc gac ctt cgc gtt tcc cga ctt tgc ctc ggc tgt atg acc ttt ggc     144
Thr Asp Leu Arg Val Ser Arg Leu Cys Leu Gly Cys Met Thr Phe Gly
         35                  40                  45 gag cca gat cgc ggt aat cac gca tgg aca ctg ccg gaa gaa agc agc     192
Glu Pro Asp Arg Gly Asn His Ala Trp Thr Leu Pro Glu Glu Ser Ser
     50                  55                  60 cgt ccc ata att aaa cgt gca ctg gaa ggc ggc ata aat ttc ttt gat     240
Arg Pro Ile Ile Lys Arg Ala Leu Glu Gly Gly Ile Asn Phe Phe Asp
 65                  70                  75                  80 acc gcc aac agt tat tct gac ggc agc agc gaa gag atc gtc ggt cgc     288
Thr Ala Asn Ser Tyr Ser Asp Gly Ser Ser Glu Glu Ile Val Gly Arg
             85                  90                  95 gca ctg cgg gat ttc gcc cgt cgt gaa gac gtg gtc gtt gcg acc aaa     336
Ala Leu Arg Asp Phe Ala Arg Arg Glu Asp Val Val Val Ala Thr Lys
            100                 105                 110 gtg ttc cat cgc gtt ggt gat tta ccg gaa gga tta tcc cgt gcg caa     384
Val Phe His Arg Val Gly Asp Leu Pro Glu Gly Leu Ser Arg Ala Gln
        115                 120                 125 att ttg cgc tct atc gac gac agc ctg cga cgt ctc ggc atg gat tat     432
Ile Leu Arg Ser Ile Asp Asp Ser Leu Arg Arg Leu Gly Met Asp Tyr
    130                 135                 140 gtc gat atc ctg caa att cat cgc tgg gat tac aac acg ccg atc gaa     480
Val Asp Ile Leu Gln Ile His Arg Trp Asp Tyr Asn Thr Pro Ile Glu
145                 150                 155                 160 gag acg ctg gaa gcc ctc aac gac gtg gta aaa gcc ggg aaa gcg cgt     528
Glu Thr Leu Glu Ala Leu Asn Asp Val Val Lys Ala Gly Lys Ala Arg
                165                 170                 175 tat atc ggc gcg tca tca atg cac gct tcg cag ttt gct cag gca ctg     576
Tyr Ile Gly Ala Ser Ser Met His Ala Ser Gln Phe Ala Gln Ala Leu
            180                 185                 190 gaa ctc caa aaa cag cac ggc tgg gcg cag ttt gtc agt atg cag gat     624
Glu Leu Gln Lys Gln His Gly Trp Ala Gln Phe Val Ser Met Gln Asp
        195                 200                 205 cac tac aat ctg att tat cgt gaa gaa gag cgc gag atg cta cca ctg     672
His Tyr Asn Leu Ile Tyr Arg Glu Glu Glu Arg Glu Met Leu Pro Leu
    210                 215                 220 tgt tat cag gag ggc gtg gcg gta att cca tgg agc ccg ctg gca agg     720
Cys Tyr Gln Glu Gly Val Ala Val Ile Pro Trp Ser Pro Leu Ala Arg
225                 230                 235                 240 ggc cgt ctg acg cgt ccg tgg gga gaa act acc gca cga ctg gtg tct     768
Gly Arg Leu Thr Arg Pro Trp Gly Glu Thr Thr Ala Arg Leu Val Ser
                245                 250                 255 gat gag gtg ggg aaa aat ctc tat aaa gaa agc gat gaa aat gac gcg     816
```

```
Asp Glu Val Gly Lys Asn Leu Tyr Lys Glu Ser Asp Glu Asn Asp Ala
            260                 265                 270 cag atc gca gag cgg tta aca ggc gtc agt gaa gaa ctg ggg gcg aca      864
Gln Ile Ala Glu Arg Leu Thr Gly Val Ser Glu Glu Leu Gly Ala Thr
        275                 280                 285 cga gca caa gtt gcg ctg gcc tgg ttg ttg agt aaa ccg ggc att gcc      912
Arg Ala Gln Val Ala Leu Ala Trp Leu Leu Ser Lys Pro Gly Ile Ala
    290                 295                 300 gca ccg att atc gga act tcg cgc gaa gaa cag ctt gat gag cta ttg      960
Ala Pro Ile Ile Gly Thr Ser Arg Glu Glu Gln Leu Asp Glu Leu Leu
305                 310                 315                 320 aac gcg gtg gat atc act ttg aag ccg gaa cag att gcc gaa ctg gaa     1008
Asn Ala Val Asp Ile Thr Leu Lys Pro Glu Gln Ile Ala Glu Leu Glu
                325                 330                 335 acg ccg tat aaa ccg cat cct gtc gta gga ttt aaa                     1044
Thr Pro Tyr Lys Pro His Pro Val Val Gly Phe Lys
            340                 345

<210> SEQ ID NO 10
<211> LENGTH: 1194
<212> TYPE: DNA
<213> ORGANISM: Escherichia coli
<220> FEATURE:
<221> NAME/KEY: CDS
<222> LOCATION: (1)..(1194)

<400> SEQUENCE: 10 atg aag caa ctc acc att ctg ggc tcg acc ggc tcg att ggt tgc agc       48
Met Lys Gln Leu Thr Ile Leu Gly Ser Thr Gly Ser Ile Gly Cys Ser
1               5                   10                  15 acg ctg gac gtg gtg cgc cat aat ccc gaa cac ttc cgc gta gtt gcg       96
Thr Leu Asp Val Val Arg His Asn Pro Glu His Phe Arg Val Val Ala
            20                  25                  30 ctg gtg gca ggc aaa aat gtc act cgc atg gta gaa cag tgc ctg gaa      144
Leu Val Ala Gly Lys Asn Val Thr Arg Met Val Glu Gln Cys Leu Glu
        35                  40                  45 ttc tct ccc cgc tat gcc gta atg gac gat gaa gcg agt gcg aaa ctt      192
Phe Ser Pro Arg Tyr Ala Val Met Asp Asp Glu Ala Ser Ala Lys Leu
    50                  55                  60 ctt aaa acg atg cta cag caa cag ggt agc cgc acc gaa gtc tta agt      240
Leu Lys Thr Met Leu Gln Gln Gln Gly Ser Arg Thr Glu Val Leu Ser
65                  70                  75                  80 ggg caa caa gcc gct tgc gat atg gca gcg ctt gag gat gtt gat cag      288
Gly Gln Gln Ala Ala Cys Asp Met Ala Ala Leu Glu Asp Val Asp Gln
                85                  90                  95 gtg atg gca gcc att gtt ggc gct gct ggg ctg tta cct acg ctt gct      336
Val Met Ala Ala Ile Val Gly Ala Ala Gly Leu Leu Pro Thr Leu Ala
            100                 105                 110 gcg atc cgc gcg ggt aaa acc att ttg ctg gcc aat aaa gaa tca ctg      384
Ala Ile Arg Ala Gly Lys Thr Ile Leu Leu Ala Asn Lys Glu Ser Leu
        115                 120                 125 gtt acc tgc gga cgt ctg ttt atg gac gcc gta aag cag agc aaa gcg      432
Val Thr Cys Gly Arg Leu Phe Met Asp Ala Val Lys Gln Ser Lys Ala
    130                 135                 140 caa ttg tta ccg gtc gat agc gaa cat aac gcc att ttt cag agt tta      480
Gln Leu Leu Pro Val Asp Ser Glu His Asn Ala Ile Phe Gln Ser Leu
145                 150                 155                 160 ccg caa cct atc cag cat aat ctg gga tac gct gac ctt gag caa aat      528
Pro Gln Pro Ile Gln His Asn Leu Gly Tyr Ala Asp Leu Glu Gln Asn
                165                 170                 175 ggc gtg gtg tcc att tta ctt acc ggg tct ggt ggc cct ttc cgt gag      576
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| Gly | Val | Val | Ser | Ile | Leu | Leu | Thr | Gly | Ser | Gly | Gly | Pro | Phe | Arg | Glu |      |
|     |     |     |     | 180 |     |     |     |     | 185 |     |     |     |     | 190 |     |      |

```
acg cca ttg cgc gat ttg gca aca atg acg ccg gat caa gcc tgc cgt    624
Thr Pro Leu Arg Asp Leu Ala Thr Met Thr Pro Asp Gln Ala Cys Arg
        195                 200                 205 cat ccg aac tgg tcg atg ggg cgt aaa att tct gtc gat tcg gct acc    672
His Pro Asn Trp Ser Met Gly Arg Lys Ile Ser Val Asp Ser Ala Thr
    210                 215                 220 atg atg aac aaa ggt ctg gaa tac att gaa gcg cgt tgg ctg ttt aac    720
Met Met Asn Lys Gly Leu Glu Tyr Ile Glu Ala Arg Trp Leu Phe Asn
225                 230                 235                 240 gcc agc gcc agc cag atg gaa gtg ctg att cac ccg cag tca gtg att    768
Ala Ser Ala Ser Gln Met Glu Val Leu Ile His Pro Gln Ser Val Ile
                245                 250                 255 cac tca atg gtg cgc tat cag gac ggc agt gtt ctg gcg cag ctg ggg    816
His Ser Met Val Arg Tyr Gln Asp Gly Ser Val Leu Ala Gln Leu Gly
            260                 265                 270 gaa ccg gat atg gta cgc caa ttg ccc aca cca tgg gca tgg ccg aat    864
Glu Pro Asp Met Val Arg Gln Leu Pro Thr Pro Trp Ala Trp Pro Asn
        275                 280                 285 cgc gtg aac tct ggc gtg aag ccg ctc gat ttt tgc aaa cta agt gcg    912
Arg Val Asn Ser Gly Val Lys Pro Leu Asp Phe Cys Lys Leu Ser Ala
    290                 295                 300 ttg aca ttt gcc gca ccg gat tat gat cgt tat cca tgc ctg aaa ctg    960
Leu Thr Phe Ala Ala Pro Asp Tyr Asp Arg Tyr Pro Cys Leu Lys Leu
305                 310                 315                 320 gcg atg gag gcg ttc gaa caa ggc cag gca gcg acg aca gca ttg aat   1008
Ala Met Glu Ala Phe Glu Gln Gly Gln Ala Ala Thr Thr Ala Leu Asn
                325                 330                 335 gcc gca aac gaa atc acc gtt gct gct ttt ctt gcg caa caa atc cgc   1056
Ala Ala Asn Glu Ile Thr Val Ala Ala Phe Leu Ala Gln Gln Ile Arg
            340                 345                 350 ttt acg gat atc gct gcg ttg aat tta tcc gta ctg gaa aaa atg gat   1104
Phe Thr Asp Ile Ala Ala Leu Asn Leu Ser Val Leu Glu Lys Met Asp
        355                 360                 365 atg cgc gaa cca caa tgt gtg gac gat gtg tta tct gtt gat gcg aac   1152
Met Arg Glu Pro Gln Cys Val Asp Asp Val Leu Ser Val Asp Ala Asn
    370                 375                 380 gcg cgt gaa gtc gcc aga aaa gag gtg atg cgt ctc gca agc             1194
Ala Arg Glu Val Ala Arg Lys Glu Val Met Arg Leu Ala Ser
385                 390                 395

<210> SEQ ID NO 11
<211> LENGTH: 4390
<212> TYPE: DNA
<213> ORGANISM: Escherichia coli
<220> FEATURE:
<221> NAME/KEY: CDS
<222> LOCATION: (208)..(447)
<220> FEATURE:
<221> NAME/KEY: CDS
<222> LOCATION: (450)..(1346)
<220> FEATURE:
<221> NAME/KEY: CDS
<222> LOCATION: (1374)..(3233)
<220> FEATURE:
<221> NAME/KEY: CDS
<222> LOCATION: (3344)..(4390)

<400> SEQUENCE: 11
atggcggcaa tggttcgttg gcaagcctta agcgacttgt ataggaaaaa atacagcagc     60
ccacacctgc ggctgcatcc aggcgcggaa gtataccact aacatcgctt tgctgtgcac    120
```

-continued

```
atcaccttac cattgcgcgt tatttgctat ttgccctgag tccgttacca tgacggggcg         180
aaaaatattg agagtcagac attcatt atg ccg aag aaa aat gag gcg ccc gcc         234
                              Met Pro Lys Lys Asn Glu Ala Pro Ala
                                1               5 agc ttt gaa aag gcg ctg agc gag ctg gaa cag att gta acc cgt ctg           282
Ser Phe Glu Lys Ala Leu Ser Glu Leu Glu Gln Ile Val Thr Arg Leu
 10              15                  20                  25 gaa agt ggc gac ctg ccg ctg gaa gag gcg ctg aac gag ttc gaa cgc           330
Glu Ser Gly Asp Leu Pro Leu Glu Glu Ala Leu Asn Glu Phe Glu Arg
                 30                  35                  40 ggc gtg cag ctg gca cgt cag ggg cag gcc aaa tta caa caa gcc gaa           378
Gly Val Gln Leu Ala Arg Gln Gly Gln Ala Lys Leu Gln Gln Ala Glu
                 45                  50                  55 cag cgc gta caa att ctg ctg tct gac aat gaa gac gcc tct cta acc           426
Gln Arg Val Gln Ile Leu Leu Ser Asp Asn Glu Asp Ala Ser Leu Thr
         60                  65                  70 cct ttt aca ccg gac aat gag ta atg gac ttt ccg cag caa ctc gaa            473
Pro Phe Thr Pro Asp Asn Glu    Met Asp Phe Pro Gln Gln Leu Glu
 75                  80         1               5 gcc tgc gtt aag cag gcc aac cag gcg ctg agc cgt ttt atc gcc cca           521
Ala Cys Val Lys Gln Ala Asn Gln Ala Leu Ser Arg Phe Ile Ala Pro
 10                  15                  20 ctg ccc ttt cag aac act ccc gtg gtc gaa acc atg cag tat ggc gca           569
Leu Pro Phe Gln Asn Thr Pro Val Val Glu Thr Met Gln Tyr Gly Ala
 25                  30                  35                  40 tta tta ggt ggt aag cgc ctg cga cct ttc ctg gtt tat gcc acc ggt           617
Leu Leu Gly Gly Lys Arg Leu Arg Pro Phe Leu Val Tyr Ala Thr Gly
                 45                  50                  55 cat atg ttc ggc gtt agc aca aac acg ctg gac gca ccc gct gcc gcc           665
His Met Phe Gly Val Ser Thr Asn Thr Leu Asp Ala Pro Ala Ala Ala
         60                  65                  70 gtt gag tgt atc cac gct tac tca tta att cat gat gat tta ccg gca           713
Val Glu Cys Ile His Ala Tyr Ser Leu Ile His Asp Asp Leu Pro Ala
         75                  80                  85 atg gat gat gac gat ctg cgt cgc ggt ttg cca acc tgc cat gtg aag           761
Met Asp Asp Asp Asp Leu Arg Arg Gly Leu Pro Thr Cys His Val Lys
 90                  95                 100 ttt ggc gaa gca aac gcg att ctc gct ggc gac gct tta caa acg ctg           809
Phe Gly Glu Ala Asn Ala Ile Leu Ala Gly Asp Ala Leu Gln Thr Leu
105                 110                 115                 120 gcg ttc tcg att tta agc gat gcc gat atg ccg gaa gtg tcg gac cgc           857
Ala Phe Ser Ile Leu Ser Asp Ala Asp Met Pro Glu Val Ser Asp Arg
                125                 130                 135 gac aga att tcg atg att tct gaa ctg gcg agc gcc agt ggt att gcc           905
Asp Arg Ile Ser Met Ile Ser Glu Leu Ala Ser Ala Ser Gly Ile Ala
                140                 145                 150 gga atg tgc ggt ggt cag gca tta gat tta gac gcg gaa ggc aaa cac           953
Gly Met Cys Gly Gly Gln Ala Leu Asp Leu Asp Ala Glu Gly Lys His
                155                 160                 165 gta cct ctg gac gcg ctt gag cgt att cat cgt cat aaa acc ggc gca          1001
Val Pro Leu Asp Ala Leu Glu Arg Ile His Arg His Lys Thr Gly Ala
170                 175                 180 ttg att cgc gcc gcc gtt cgc ctt ggt gca tta agc gcc gga gat aaa          1049
Leu Ile Arg Ala Ala Val Arg Leu Gly Ala Leu Ser Ala Gly Asp Lys
185                 190                 195                 200 gga cgt cgt gct ctg ccg gta ctc gac aag tat gca gag agc atc ggc          1097
Gly Arg Arg Ala Leu Pro Val Leu Asp Lys Tyr Ala Glu Ser Ile Gly
                205                 210                 215 ctt gcc ttc cag gtt cag gat gac atc ctg gat gtg gtg gga gat act          1145
```

-continued

| | | | | | | | | | | | | |
|---|---|---|---|---|---|---|---|---|---|---|---|---|
| Leu | Ala | Phe | Gln | Val | Gln | Asp | Asp | Ile | Leu | Asp | Val | Val | Gly | Asp | Thr |
| | | 220 | | | | | 225 | | | | | 230 | | | |

```
gca acg ttg gga aaa cgc cag ggt gcc gac cag caa ctt ggt aaa agt      1193
Ala Thr Leu Gly Lys Arg Gln Gly Ala Asp Gln Gln Leu Gly Lys Ser
        235                 240                 245 acc tac cct gca ctt ctg ggt ctt gag caa gcc cgg aag aaa gcc cgg      1241
Thr Tyr Pro Ala Leu Leu Gly Leu Glu Gln Ala Arg Lys Lys Ala Arg
        250                 255                 260 gat ctg atc gac gat gcc cgt cag tcg ctg aaa caa ctg gct gaa cag      1289
Asp Leu Ile Asp Asp Ala Arg Gln Ser Leu Lys Gln Leu Ala Glu Gln
265                 270                 275                 280 tca ctc gat acc tcg gca ctg gaa gcg cta gcg gac tac atc atc cag      1337
Ser Leu Asp Thr Ser Ala Leu Glu Ala Leu Ala Asp Tyr Ile Ile Gln
                285                 290                 295 cgt aat aaa taaacaataa gtattaatag gcccctg atg agt ttt gat att gcc    1391
Arg Asn Lys                                 Met Ser Phe Asp Ile Ala
                                              1               5 aaa tac ccg acc ctg gca ctg gtc gac tcc acc cag gag tta cga ctg      1439
Lys Tyr Pro Thr Leu Ala Leu Val Asp Ser Thr Gln Glu Leu Arg Leu
         10                  15                  20 ttg ccg aaa gag agt tta ccg aaa ctc tgc gac gaa ctg cgc cgc tat      1487
Leu Pro Lys Glu Ser Leu Pro Lys Leu Cys Asp Glu Leu Arg Arg Tyr
     25                  30                  35 tta ctc gac agc gtg agc cgt tcc agc ggg cac ttc gcc tcc ggg ctg      1535
Leu Leu Asp Ser Val Ser Arg Ser Ser Gly His Phe Ala Ser Gly Leu
 40                  45                  50 ggc acg gtc gaa ctg acc gtg gcg ctg cac tat gtc tac aac acc ccg      1583
Gly Thr Val Glu Leu Thr Val Ala Leu His Tyr Val Tyr Asn Thr Pro
 55                  60                  65                  70 ttt gac caa ttg att tgg gat gtg ggg cat cag gct tat ccg cat aaa      1631
Phe Asp Gln Leu Ile Trp Asp Val Gly His Gln Ala Tyr Pro His Lys
                 75                  80                  85 att ttg acc gga cgc cgc gac aaa atc ggc acc atc cgt cag aaa ggc      1679
Ile Leu Thr Gly Arg Arg Asp Lys Ile Gly Thr Ile Arg Gln Lys Gly
             90                  95                 100 ggt ctg cac ccg ttc ccg tgg cgc ggc gaa agc gaa tat gac gta tta      1727
Gly Leu His Pro Phe Pro Trp Arg Gly Glu Ser Glu Tyr Asp Val Leu
        105                 110                 115 agc gtc ggg cat tca tca acc tcc atc agt gcc gga att ggt att gcg      1775
Ser Val Gly His Ser Ser Thr Ser Ile Ser Ala Gly Ile Gly Ile Ala
120                 125                 130 gtt gct gcc gaa aaa gaa ggc aaa aat cgc cgc acc gtc tgt gtc att      1823
Val Ala Ala Glu Lys Glu Gly Lys Asn Arg Arg Thr Val Cys Val Ile
135                 140                 145                 150 ggc gat ggc gcg att acc gca ggc atg gcg ttt gaa gcg atg aat cac      1871
Gly Asp Gly Ala Ile Thr Ala Gly Met Ala Phe Glu Ala Met Asn His
                155                 160                 165 gcg ggc gat atc cgt cct gat atg ctg gtg att ctc aac gac aat gaa      1919
Ala Gly Asp Ile Arg Pro Asp Met Leu Val Ile Leu Asn Asp Asn Glu
            170                 175                 180 atg tcg att tcc gaa aat gtc ggc gcg ctc aac aac cat ctg gca cag      1967
Met Ser Ile Ser Glu Asn Val Gly Ala Leu Asn Asn His Leu Ala Gln
        185                 190                 195 ctg ctt tcc ggt aag ctt tac tct tca ctg cgc gaa ggc ggg aaa aaa      2015
Leu Leu Ser Gly Lys Leu Tyr Ser Ser Leu Arg Glu Gly Gly Lys Lys
200                 205                 210 gtt ttc tct ggc gtg ccg cca att aaa gag ctg ctc aaa cgc acc gaa      2063
Val Phe Ser Gly Val Pro Pro Ile Lys Glu Leu Leu Lys Arg Thr Glu
215                 220                 225                 230
```

-continued

| | | |
|---|---|---|
| gaa cat att aaa ggc atg gta gtg cct ggc acg ttg ttt gaa gag ctg<br>Glu His Ile Lys Gly Met Val Val Pro Gly Thr Leu Phe Glu Glu Leu<br>235 240 245 | | 2111 |
| ggc ttt aac tac atc ggc ccg gtg gac ggt cac gat gtg ctg ggg ctt<br>Gly Phe Asn Tyr Ile Gly Pro Val Asp Gly His Asp Val Leu Gly Leu<br>250 255 260 | | 2159 |
| atc acc acg cta aag aac atg cgc gac ctg aaa ggc ccg cag ttc ctg<br>Ile Thr Thr Leu Lys Asn Met Arg Asp Leu Lys Gly Pro Gln Phe Leu<br>265 270 275 | | 2207 |
| cat atc atg acc aaa aaa ggt cgt ggt tat gaa ccg gca gaa aaa gac<br>His Ile Met Thr Lys Lys Gly Arg Gly Tyr Glu Pro Ala Glu Lys Asp<br>280 285 290 | | 2255 |
| ccg atc act ttc cac gcc gtg cct aaa ttt gat ccc tcc agc ggt tgt<br>Pro Ile Thr Phe His Ala Val Pro Lys Phe Asp Pro Ser Ser Gly Cys<br>295 300 305 310 | | 2303 |
| ttg ccg aaa agt agc ggc ggt ttg ccg agc tat tca aaa atc ttt ggc<br>Leu Pro Lys Ser Ser Gly Gly Leu Pro Ser Tyr Ser Lys Ile Phe Gly<br>315 320 325 | | 2351 |
| gac tgg ttg tgc gaa acg gca gcg aaa gac aac aag ctg atg gcg att<br>Asp Trp Leu Cys Glu Thr Ala Ala Lys Asp Asn Lys Leu Met Ala Ile<br>330 335 340 | | 2399 |
| act ccg gcg atg cgt gaa ggt tcc ggc atg gtc gag ttt tca cgt aaa<br>Thr Pro Ala Met Arg Glu Gly Ser Gly Met Val Glu Phe Ser Arg Lys<br>345 350 355 | | 2447 |
| ttc ccg gat cgc tac ttc gac gtg gca att gcc gag caa cac gcg gtg<br>Phe Pro Asp Arg Tyr Phe Asp Val Ala Ile Ala Glu Gln His Ala Val<br>360 365 370 | | 2495 |
| acc ttt gct gcg ggt ctg gcg att ggt ggg tac aaa ccc att gtc gcg<br>Thr Phe Ala Ala Gly Leu Ala Ile Gly Gly Tyr Lys Pro Ile Val Ala<br>375 380 385 390 | | 2543 |
| att tac tcc act ttc ctg caa cgc gcc tat gat cag gtg ctg cat gac<br>Ile Tyr Ser Thr Phe Leu Gln Arg Ala Tyr Asp Gln Val Leu His Asp<br>395 400 405 | | 2591 |
| gtg gcg att caa aag ctt ccg gtc ctg ttc gcc atc gac cgc gcg ggc<br>Val Ala Ile Gln Lys Leu Pro Val Leu Phe Ala Ile Asp Arg Ala Gly<br>410 415 420 | | 2639 |
| att gtt ggt gct gac ggt caa acc cat cag ggt gct ttt gat ctc tct<br>Ile Val Gly Ala Asp Gly Gln Thr His Gln Gly Ala Phe Asp Leu Ser<br>425 430 435 | | 2687 |
| tac ctg cgc tgc ata ccg gaa atg gtc att atg acc ccg agc gat gaa<br>Tyr Leu Arg Cys Ile Pro Glu Met Val Ile Met Thr Pro Ser Asp Glu<br>440 445 450 | | 2735 |
| aac gaa tgt cgc cag atg ctc tat acc ggc tat cac tat aac gat ggc<br>Asn Glu Cys Arg Gln Met Leu Tyr Thr Gly Tyr His Tyr Asn Asp Gly<br>455 460 465 470 | | 2783 |
| ccg tca gcg gtg cgc tac ccg cgt ggc aac gcg gtc ggc gtg gaa ctg<br>Pro Ser Ala Val Arg Tyr Pro Arg Gly Asn Ala Val Gly Val Glu Leu<br>475 480 485 | | 2831 |
| acg ccg ctg gaa aaa cta cca att ggc aaa ggc att gtg aag cgt cgt<br>Thr Pro Leu Glu Lys Leu Pro Ile Gly Lys Gly Ile Val Lys Arg Arg<br>490 495 500 | | 2879 |
| ggc gag aaa ctg gcg atc ctt aac ttt ggt acg ctg atg cca gaa gcg<br>Gly Glu Lys Leu Ala Ile Leu Asn Phe Gly Thr Leu Met Pro Glu Ala<br>505 510 515 | | 2927 |
| gcg aaa gtc gcc gaa tcg ctg aac gcc acg ctg gtc gat atg cgt ttt<br>Ala Lys Val Ala Glu Ser Leu Asn Ala Thr Leu Val Asp Met Arg Phe<br>520 525 530 | | 2975 |
| gtg aaa ccg ctt gat gaa gcg tta att ctg gaa atg gcc gcc agc cat<br>Val Lys Pro Leu Asp Glu Ala Leu Ile Leu Glu Met Ala Ala Ser His<br>535 540 545 550 | | 3023 |

```
gaa gcg ctg gtc acc gta gaa gaa aac gcc att atg ggc ggc gca ggc      3071
Glu Ala Leu Val Thr Val Glu Glu Asn Ala Ile Met Gly Gly Ala Gly
            555                 560                 565 agc ggc gtg aac gaa gtg ctg atg gcc cat cgt aaa cca gta ccc gtg      3119
Ser Gly Val Asn Glu Val Leu Met Ala His Arg Lys Pro Val Pro Val
        570                 575                 580 ctg aac att ggc ctg ccg gac ttc ttt att ccg caa gga act cag gaa      3167
Leu Asn Ile Gly Leu Pro Asp Phe Phe Ile Pro Gln Gly Thr Gln Glu
    585                 590                 595 gaa atg cgc gcc gaa ctc ggc ctc gat gcc gct ggt atg gaa gcc aaa      3215
Glu Met Arg Ala Glu Leu Gly Leu Asp Ala Ala Gly Met Glu Ala Lys
600                 605                 610 atc aag gcc tgg ctg gca taatccctac tccactcctg ctatgcttaa             3263
Ile Lys Ala Trp Leu Ala
615             620 gaaattattc atagactcta ataattcga gttgcaggaa gcggcaaac gagtgaagcc      3323 ccaggagctt acataagtaa gtg act ggg gtg aac gaa tgc agc cgc agc aca   3376
                      Val Thr Gly Val Asn Glu Cys Ser Arg Ser Thr
                        1               5                  10 tgc aac ttg aag tat gac gag tat agc agg agt ggc agc atg caa tac      3424
Cys Asn Leu Lys Tyr Asp Glu Tyr Ser Arg Ser Gly Ser Met Gln Tyr
            15                  20                  25 aac ccc tta gga aaa acc gac ctt cgc gtt tcc cga ctt tgc ctc ggc      3472
Asn Pro Leu Gly Lys Thr Asp Leu Arg Val Ser Arg Leu Cys Leu Gly
        30                  35                  40 tgt atg acc ttt ggc gag cca gat cgc ggt aat cac gca tgg aca ctg      3520
Cys Met Thr Phe Gly Glu Pro Asp Arg Gly Asn His Ala Trp Thr Leu
    45                  50                  55 ccg gaa gaa agc agc cgt ccc ata att aaa cgt gca ctg gaa ggc ggc      3568
Pro Glu Glu Ser Ser Arg Pro Ile Ile Lys Arg Ala Leu Glu Gly Gly
60                  65                  70                  75 ata aat ttc ttt gat acc gcc aac agt tat tct gac ggc agc agc gaa      3616
Ile Asn Phe Phe Asp Thr Ala Asn Ser Tyr Ser Asp Gly Ser Ser Glu
            80                  85                  90 gag atc gtc ggt cgc gca ctg cgg gat ttc gcc cgt cgt gaa gac gtg      3664
Glu Ile Val Gly Arg Ala Leu Arg Asp Phe Ala Arg Arg Glu Asp Val
        95                  100                 105 gtc gtt gcg acc aaa gtg ttc cat cgc gtt ggt gat tta ccg gaa gga      3712
Val Val Ala Thr Lys Val Phe His Arg Val Gly Asp Leu Pro Glu Gly
    110                 115                 120 tta tcc cgt gcg caa att ttg cgc tct atc gac gac agc ctg cga cgt      3760
Leu Ser Arg Ala Gln Ile Leu Arg Ser Ile Asp Asp Ser Leu Arg Arg
125                 130                 135 ctc ggc atg gat tat gtc gat atc ctg caa att cat cgc tgg gat tac      3808
Leu Gly Met Asp Tyr Val Asp Ile Leu Gln Ile His Arg Trp Asp Tyr
140                 145                 150                 155 aac acg ccg atc gaa gag acg ctg gaa gcc ctc aac gac gtg gta aaa      3856
Asn Thr Pro Ile Glu Glu Thr Leu Glu Ala Leu Asn Asp Val Val Lys
            160                 165                 170 gcc ggg aaa gcg cgt tat atc ggc gcg tca tca atg cac gct tcg cag      3904
Ala Gly Lys Ala Arg Tyr Ile Gly Ala Ser Ser Met His Ala Ser Gln
        175                 180                 185 ttt gct cag gca ctg gaa ctc caa aaa cag cac ggc tgg gcg cag ttt      3952
Phe Ala Gln Ala Leu Glu Leu Gln Lys Gln His Gly Trp Ala Gln Phe
    190                 195                 200 gtc agt atg cag gat cac tac aat ctg att tat cgt gaa gaa gag cgc      4000
Val Ser Met Gln Asp His Tyr Asn Leu Ile Tyr Arg Glu Glu Glu Arg
205                 210                 215
```

```
gag atg cta cca ctg tgt tat cag gag ggc gtg gcg gta att cca tgg    4048
Glu Met Leu Pro Leu Cys Tyr Gln Glu Gly Val Ala Val Ile Pro Trp
220                 225                 230                 235 agc ccg ctg gca agg ggc cgt ctg acg cgt ccg tgg gga gaa act acc    4096
Ser Pro Leu Ala Arg Gly Arg Leu Thr Arg Pro Trp Gly Glu Thr Thr
            240                 245                 250 gca cga ctg gtg tct gat gag gtg ggg aaa aat ctc tat aaa gaa agc    4144
Ala Arg Leu Val Ser Asp Glu Val Gly Lys Asn Leu Tyr Lys Glu Ser
        255                 260                 265 gat gaa aat gac gcg cag atc gca gag cgg tta aca ggc gtc agt gaa    4192
Asp Glu Asn Asp Ala Gln Ile Ala Glu Arg Leu Thr Gly Val Ser Glu
    270                 275                 280 gaa ctg ggg gcg aca cga gca caa gtt gcg ctg gcc tgg ttg ttg agt    4240
Glu Leu Gly Ala Thr Arg Ala Gln Val Ala Leu Ala Trp Leu Leu Ser
285                 290                 295 aaa ccg ggc att gcc gca ccg att atc gga act tcg cgc gaa gaa cag    4288
Lys Pro Gly Ile Ala Ala Pro Ile Ile Gly Thr Ser Arg Glu Glu Gln
300                 305                 310                 315 ctt gat gag cta ttg aac gcg gtg gat atc act ttg aag ccg gaa cag    4336
Leu Asp Glu Leu Leu Asn Ala Val Asp Ile Thr Leu Lys Pro Glu Gln
            320                 325                 330 att gcc gaa ctg gaa acg ccg tat aaa ccg cat cct gtc gta gga ttt    4384
Ile Ala Glu Leu Glu Thr Pro Tyr Lys Pro His Pro Val Val Gly Phe
        335                 340                 345 aaa taa                                                             4390
Lys

<210> SEQ ID NO 12
<211> LENGTH: 33
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 12
ccggatccat ggcggcaatg gttcgttggc aag                                33

<210> SEQ ID NO 13
<211> LENGTH: 34
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 13
ccgaattctt atttaaatcc tacgacagga tgcg                               34

<210> SEQ ID NO 14
<211> LENGTH: 33
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 14
ccggatccat gagttttgat attgccaaat acc                                33

<210> SEQ ID NO 15
<211> LENGTH: 33
<212> TYPE: DNA
<213> ORGANISM: Artificial Sequence
```

```
<220> FEATURE:
<223> OTHER INFORMATION: Description of Artificial Sequence:Synthetic
      DNA

<400> SEQUENCE: 15
ccgaattctt atgccagcca ggccttgatt ttg                           33

<210> SEQ ID NO 16
<211> LENGTH: 33
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 16
ccgaattctt actcattgtc cggtgtaaaa ggg                           33

<210> SEQ ID NO 17
<211> LENGTH: 33
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 17
ccggatccat ggactttccg cagcaactcg aag                           33

<210> SEQ ID NO 18
<211> LENGTH: 33
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 18
ccgaattctt atttattacg ctggatgatg tag                           33

<210> SEQ ID NO 19
<211> LENGTH: 33
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 19
ccggatccta atccctactc cactcctgct atg                           33

<210> SEQ ID NO 20
<211> LENGTH: 30
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 20
gggggatcca agcaactcac cattctgggc                               30

<210> SEQ ID NO 21
<211> LENGTH: 30
<212> TYPE: DNA
<213> ORGANISM: Artificial Sequence
<220> FEATURE:
```

```
<223> OTHER INFORMATION: Description of Artificial Sequence:Synthetic
      DNA

<400> SEQUENCE: 21
gggggatccg cttgcgagac gcatcacctc                                           30

<210> SEQ ID NO 22
<211> LENGTH: 32
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 22
gggggatcca gttttgatat tgccaaatac cc                                        32

<210> SEQ ID NO 23
<211> LENGTH: 32
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 23
gggggatcct gccagccagg ccttgatttt gg                                        32

<210> SEQ ID NO 24
<211> LENGTH: 30
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 24
gggggatccg agcaactcac cattctgggc                                           30

<210> SEQ ID NO 25
<211> LENGTH: 30
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 25
gggggatccg cttgcgagac gcatcacctc                                           30

<210> SEQ ID NO 26
<211> LENGTH: 637
<212> TYPE: PRT
<213> ORGANISM: Rhodobacter sphaeroides

<400> SEQUENCE: 26

Met Thr Asp Arg Pro Cys Thr Pro Thr Leu Asp Arg Val Thr Leu Pro
  1               5                  10                  15

Val Asp Met Lys Gly Leu Thr Asp Arg Glu Leu Arg Ser Leu Ala Asp
                 20                  25                  30

Glu Leu Arg Ala Glu Thr Ile Ser Ala Val Ser Val Thr Gly Gly His
             35                  40                  45

Leu Gly Ala Gly Leu Gly Val Val Glu Leu Thr Val Ala Leu His Ala
         50                  55                  60
```

-continued

```
Val Phe Asp Ala Pro Arg Asp Lys Ile Ile Trp Asp Val Gly His Gln
 65                  70                  75                  80

Cys Tyr Pro His Lys Ile Leu Thr Gly Arg Asp Arg Ile Arg Thr
                 85                  90                  95

Leu Arg Gln Gly Gly Leu Ser Gly Phe Thr Lys Arg Ser Glu Ser
            100                 105                 110

Pro Tyr Asp Cys Phe Gly Ala Gly His Ser Ser Thr Ser Ile Ser Ala
            115                 120                 125

Ala Val Gly Phe Ala Ala Arg Glu Met Gly Gly Asp Thr Gly Asp
130                 135                 140

Ala Val Ala Val Ile Gly Asp Gly Ser Met Ser Ala Gly Met Ala Phe
145                 150                 155                 160

Glu Ala Leu Asn His Gly Gly His Leu Lys Asn Arg Val Ile Val Ile
                165                 170                 175

Leu Asn Asp Asn Glu Met Ser Ile Ala Pro Pro Val Gly Ala Leu Ser
            180                 185                 190

Ser Tyr Leu Ser Arg Leu Tyr Ala Gly Ala Pro Phe Gln Asp Phe Lys
            195                 200                 205

Ala Ala Ala Lys Gly Ala Leu Gly Leu Leu Pro Glu Pro Phe Gln Glu
210                 215                 220

Gly Ala Arg Arg Ala Lys Glu Met Leu Lys Ser Val Thr Val Gly Gly
225                 230                 235                 240

Thr Leu Phe Glu Glu Leu Gly Phe Ser Tyr Val Gly Pro Ile Asp Gly
                245                 250                 255

His Asp Leu Asp Gln Leu Leu Pro Val Leu Arg Thr Val Lys Gln Arg
            260                 265                 270

Ala His Ala Pro Val Leu Ile His Val Ile Thr Lys Lys Gly Arg Gly
            275                 280                 285

Tyr Ala Pro Ala Glu Ala Ala Arg Asp Arg Gly His Ala Thr Asn Lys
290                 295                 300

Phe Asn Val Leu Thr Gly Ala Gln Val Lys Pro Val Ser Asn Ala Pro
305                 310                 315                 320

Ser Tyr Thr Lys Val Phe Ala Gln Ser Leu Ile Lys Glu Ala Glu Val
                325                 330                 335

Asp Glu Arg Ile Cys Ala Val Thr Ala Ala Met Pro Asp Gly Thr Gly
            340                 345                 350

Leu Asn Leu Phe Gly Glu Arg Phe Pro Lys Arg Thr Phe Asp Val Gly
            355                 360                 365

Ile Ala Glu Gln His Ala Val Thr Phe Ser Ala Ala Leu Ala Ala Gly
370                 375                 380

Gly Met Arg Pro Phe Cys Ala Ile Tyr Ser Thr Phe Leu Gln Arg Gly
385                 390                 395                 400

Tyr Asp Gln Ile Val His Asp Val Ala Ile Gln Arg Leu Pro Val Arg
                405                 410                 415

Phe Ala Ile Asp Arg Ala Gly Leu Val Gly Ala Asp Gly Ala Thr His
            420                 425                 430

Ala Gly Ser Phe Asp Val Ala Phe Leu Ser Asn Leu Pro Gly Ile Val
            435                 440                 445

Val Met Ala Ala Ala Asp Glu Ala Glu Leu Val His Met Val Ala Thr
450                 455                 460

Ala Ala Ala His Asp Glu Gly Pro Ile Ala Phe Arg Tyr Pro Arg Gly
465                 470                 475                 480

Asp Gly Val Gly Val Glu Met Pro Val Lys Gly Val Pro Leu Gln Ile
```

```
                    485                 490                 495
Gly Arg Gly Arg Val Val Arg Glu Gly Thr Arg Ile Ala Leu Leu Ser
                500                 505                 510

Phe Gly Thr Arg Leu Ala Glu Val Gln Val Ala Ala Glu Ala Leu Arg
            515                 520                 525

Ala Arg Gly Ile Ser Pro Thr Val Ala Asp Ala Arg Phe Ala Lys Pro
        530                 535                 540

Leu Asp Arg Asp Leu Ile Leu Gln Leu Ala Ala His His Glu Ala Leu
545                 550                 555                 560

Ile Thr Ile Glu Glu Gly Ala Ile Gly Gly Phe Gly Ser His Val Ala
                565                 570                 575

Gln Leu Leu Ala Glu Ala Gly Val Phe Asp Arg Gly Phe Arg Tyr Arg
            580                 585                 590

Ser Met Val Leu Pro Asp Thr Phe Ile Asp His Asn Ser Ala Glu Val
        595                 600                 605

Met Tyr Ala Thr Ala Gly Leu Asn Ala Ala Asp Ile Glu Arg Lys Ala
    610                 615                 620

Leu Glu Thr Leu Gly Val Glu Val Leu Ala Arg Arg Ala
625                 630                 635

<210> SEQ ID NO 27
<211> LENGTH: 1911
<212> TYPE: DNA
<213> ORGANISM: Rhodobacter sphaeroides
<220> FEATURE:
<221> NAME/KEY: CDS
<222> LOCATION: (1)..(1911)

<400> SEQUENCE: 27 atg acc gac aga ccc tgc acg ccg acg ctc gac cgg gtg acg ctc ccg        48
Met Thr Asp Arg Pro Cys Thr Pro Thr Leu Asp Arg Val Thr Leu Pro
 1               5                  10                  15 gtg gac atg aag ggc ctc acg gac cgt gag ctg cgc tcg ctg gcc gac        96
Val Asp Met Lys Gly Leu Thr Asp Arg Glu Leu Arg Ser Leu Ala Asp
             20                  25                  30 gag ctg cgg gcc gaa acg atc tcg gcc gtg tcg gtg acg ggc ggg cat       144
Glu Leu Arg Ala Glu Thr Ile Ser Ala Val Ser Val Thr Gly Gly His
         35                  40                  45 ctg ggc gca ggc ctc ggc gtg gtg gag ttg acg gtt gcg ctg cat gcg       192
Leu Gly Ala Gly Leu Gly Val Val Glu Leu Thr Val Ala Leu His Ala
     50                  55                  60 gtc ttc gat gcg ccg cgc gac aag atc atc tgg gac gtg ggc cac cag       240
Val Phe Asp Ala Pro Arg Asp Lys Ile Ile Trp Asp Val Gly His Gln
 65                  70                  75                  80 tgc tac ccc cac aag atc ctg acc ggg cgg cgc gac cgc atc cgc aca       288
Cys Tyr Pro His Lys Ile Leu Thr Gly Arg Arg Asp Arg Ile Arg Thr
                 85                  90                  95 ctg cgg cag ggc ggg ggt ctc tcg ggc ttc acc aag cgc tcc gag agc       336
Leu Arg Gln Gly Gly Gly Leu Ser Gly Phe Thr Lys Arg Ser Glu Ser
            100                 105                 110 ccc tac gac tgt ttc ggc gcg ggc cat tcc tcg acc tcg atc tcg gcc       384
Pro Tyr Asp Cys Phe Gly Ala Gly His Ser Ser Thr Ser Ile Ser Ala
        115                 120                 125 gcg gtg ggc ttt gcc gcg gcg cgc gag atg ggc ggc gac acg ggc gac       432
Ala Val Gly Phe Ala Ala Ala Arg Glu Met Gly Gly Asp Thr Gly Asp
    130                 135                 140 gcg gtg gcg gtg atc ggc gat ggc tcg atg tcg gcc ggc atg gcc ttc       480
Ala Val Ala Val Ile Gly Asp Gly Ser Met Ser Ala Gly Met Ala Phe
145                 150                 155                 160
```

```
gag gcg ctg aac cac ggc ggg cac ctg aag aac cgg gtg atc gtg atc      528
Glu Ala Leu Asn His Gly Gly His Leu Lys Asn Arg Val Ile Val Ile
                165                 170                 175 ctg aac gac aat gag atg agc atc gcg ccg ccg gtg ggg gcg ctg tcg      576
Leu Asn Asp Asn Glu Met Ser Ile Ala Pro Pro Val Gly Ala Leu Ser
            180                 185                 190 tcc tat ctc tcg cgg ctc tat gcg ggc gcg ccg ttc cag gac ttc aag      624
Ser Tyr Leu Ser Arg Leu Tyr Ala Gly Ala Pro Phe Gln Asp Phe Lys
        195                 200                 205 gcg gcc gcc aag gga gcg ctc ggg ctt ctg ccc gaa ccg ttc cag gag      672
Ala Ala Ala Lys Gly Ala Leu Gly Leu Leu Pro Glu Pro Phe Gln Glu
    210                 215                 220 ggc gcg cgc cgc gcc aag gag atg ctg aag agc gtc acc gtc ggc ggc      720
Gly Ala Arg Arg Ala Lys Glu Met Leu Lys Ser Val Thr Val Gly Gly
225                 230                 235                 240 acg ctc ttc gag gag ctg ggt ttc tcc tat gtc ggc ccg atc gac ggg      768
Thr Leu Phe Glu Glu Leu Gly Phe Ser Tyr Val Gly Pro Ile Asp Gly
                245                 250                 255 cac gat ctc gac cag ctt ctg ccg gtg ctg cgg acc gtc aag cag cgg      816
His Asp Leu Asp Gln Leu Leu Pro Val Leu Arg Thr Val Lys Gln Arg
            260                 265                 270 gcg cat gcg ccg gtg ctg atc cat gtc atc acc aag aag ggc agg ggc      864
Ala His Ala Pro Val Leu Ile His Val Ile Thr Lys Lys Gly Arg Gly
        275                 280                 285 tat gct ccg gcc gag gcc gcg cgc gac cgc ggc cat gcc acg aac aag      912
Tyr Ala Pro Ala Glu Ala Ala Arg Asp Arg Gly His Ala Thr Asn Lys
    290                 295                 300 ttc aac gtc ctg acc ggc gcg cag gtg aag ccg gtc tcg aac gcc ccc      960
Phe Asn Val Leu Thr Gly Ala Gln Val Lys Pro Val Ser Asn Ala Pro
305                 310                 315                 320 tcc tac acc aag gtc ttc gcc cag agc ctc atc aag gag gcc gag gtc     1008
Ser Tyr Thr Lys Val Phe Ala Gln Ser Leu Ile Lys Glu Ala Glu Val
                325                 330                 335 gac gag cgg atc tgc gcg gtg acg gcc gcc atg ccg gac ggg acg ggg     1056
Asp Glu Arg Ile Cys Ala Val Thr Ala Ala Met Pro Asp Gly Thr Gly
            340                 345                 350 ctc aac ctc ttc ggc gag cgg ttt ccg aag cgc acc ttc gac gtg ggc     1104
Leu Asn Leu Phe Gly Glu Arg Phe Pro Lys Arg Thr Phe Asp Val Gly
        355                 360                 365 atc gcg gaa cag cat gcg gtg acc ttc tcg gcg gcg ctt gcg gca ggc     1152
Ile Ala Glu Gln His Ala Val Thr Phe Ser Ala Ala Leu Ala Ala Gly
    370                 375                 380 ggc atg cgg ccc ttc tgc gcg atc tat tcc acc ttc ctc cag cgc ggc     1200
Gly Met Arg Pro Phe Cys Ala Ile Tyr Ser Thr Phe Leu Gln Arg Gly
385                 390                 395                 400 tac gac cag atc gtg cat gac gtg gcg atc cag cgc ctg ccg gtg cgc     1248
Tyr Asp Gln Ile Val His Asp Val Ala Ile Gln Arg Leu Pro Val Arg
                405                 410                 415 ttc gcc atc gat cgc gcg ggc ctc gtg ggg gcg gac ggc gcc acc cat     1296
Phe Ala Ile Asp Arg Ala Gly Leu Val Gly Ala Asp Gly Ala Thr His
            420                 425                 430 gcg ggc tcg ttc gac gtg gcc ttc ctg tcg aac ctg ccc ggc atc gtg     1344
Ala Gly Ser Phe Asp Val Ala Phe Leu Ser Asn Leu Pro Gly Ile Val
        435                 440                 445 gtg atg gcc gcc gcc gac gag gcc gag ctc gtc cat atg gtg gcc acc     1392
Val Met Ala Ala Ala Asp Glu Ala Glu Leu Val His Met Val Ala Thr
    450                 455                 460 gcc gcc gcc cat gac gaa ggg ccc atc gcc ttc cgc tac ccg cgc ggc     1440
Ala Ala Ala His Asp Glu Gly Pro Ile Ala Phe Arg Tyr Pro Arg Gly
```

```
                        465                 470                 475                 480
gac ggc gtg ggg gtc gag atg ccg gtg aag ggc gtg ccg ctc cag atc       1488
Asp Gly Val Gly Val Glu Met Pro Val Lys Gly Val Pro Leu Gln Ile
                        485                 490                 495 ggc cgc ggc cgt gtg gtg cgc gag ggc acg cga atc gcg ctt ttg tcc       1536
Gly Arg Gly Arg Val Val Arg Glu Gly Thr Arg Ile Ala Leu Leu Ser
                500                 505                 510 ttc ggc acc cgt ctg gcc gag gtg cag gtg gcc gcc gag gcg ctg cgt       1584
Phe Gly Thr Arg Leu Ala Glu Val Gln Val Ala Ala Glu Ala Leu Arg
            515                 520                 525 gcg cgc ggg atc tct ccc acg gtt gcg gat gcg cgc ttt gca aag ccg       1632
Ala Arg Gly Ile Ser Pro Thr Val Ala Asp Ala Arg Phe Ala Lys Pro
        530                 535                 540 ctc gac cgg gat ctg atc ctg cag ctc gcg gcc cat cac gag gcg ctt       1680
Leu Asp Arg Asp Leu Ile Leu Gln Leu Ala Ala His His Glu Ala Leu
545                 550                 555                 560 atc acc atc gag gag ggc gcc atc ggc ggt ttc ggc agc cat gtg gcg       1728
Ile Thr Ile Glu Glu Gly Ala Ile Gly Gly Phe Gly Ser His Val Ala
                565                 570                 575 cag ctt ctg gcc gag gcc ggg gtc ttc gac cgc ggc ttc cgg tat cgc       1776
Gln Leu Leu Ala Glu Ala Gly Val Phe Asp Arg Gly Phe Arg Tyr Arg
            580                 585                 590 tcg atg gtg ctg ccc gac acg ttc atc gac cac aac agc gcg gag gtg       1824
Ser Met Val Leu Pro Asp Thr Phe Ile Asp His Asn Ser Ala Glu Val
        595                 600                 605 atg tat gcc acc gcc ggg ctg aat gcg gcc gac ata gag cgg aag gcg       1872
Met Tyr Ala Thr Ala Gly Leu Asn Ala Ala Asp Ile Glu Arg Lys Ala
    610                 615                 620 ctg gag acg ctg ggg gtg gag gtc ctc gcc cgc cgc gcc                   1911
Leu Glu Thr Leu Gly Val Glu Val Leu Ala Arg Arg Ala
625                 630                 635

<210> SEQ ID NO 28
<211> LENGTH: 648
<212> TYPE: PRT
<213> ORGANISM: Rhodobacter sphaeroides

<400> SEQUENCE: 28

Met Thr Asn Pro Thr Pro Arg Pro Glu Thr Pro Leu Leu Asp Arg Val
 1               5                  10                  15

Cys Cys Pro Ala Asp Met Lys Ala Leu Ser Asp Ala Glu Leu Glu Arg
            20                  25                  30

Leu Ala Asp Glu Val Arg Ser Glu Val Ile Ser Val Val Ala Glu Thr
        35                  40                  45

Gly Gly His Leu Gly Ser Ser Leu Gly Val Val Glu Leu Thr Val Ala
    50                  55                  60

Leu His Ala Val Phe Asn Thr Pro Thr Asp Lys Leu Val Trp Asp Val
65                  70                  75                  80

Gly His Gln Cys Tyr Pro His Lys Ile Leu Thr Gly Arg Arg Glu Gln
                85                  90                  95

Met Arg Thr Leu Arg Gln Lys Gly Gly Leu Ser Gly Phe Thr Lys Arg
            100                 105                 110

Ser Glu Ser Ala Tyr Asp Pro Phe Gly Ala His Ser Ser Thr Ser
        115                 120                 125

Ile Ser Ala Ala Leu Gly Phe Ala Met Gly Arg Glu Leu Gly Gln Pro
    130                 135                 140

Val Gly Asp Thr Ile Ala Val Ile Gly Asp Gly Ser Ile Thr Ala Gly
145                 150                 155                 160
```

```
Met Ala Tyr Glu Ala Leu Asn His Ala Gly His Leu Asn Lys Arg Leu
                165                 170                 175

Phe Val Ile Leu Asn Asp Asn Asp Met Ser Ile Ala Pro Pro Val Gly
            180                 185                 190

Ala Leu Ala Arg Tyr Leu Val Asn Leu Ser Ser Lys Ala Pro Phe Ala
        195                 200                 205

Thr Leu Arg Ala Ala Asp Gly Leu Glu Ala Ser Leu Pro Gly Pro
    210                 215                 220

Leu Arg Asp Gly Ala Arg Arg Ala Arg Gln Leu Val Thr Gly Met Pro
225                 230                 235                 240

Gly Gly Gly Thr Leu Phe Glu Glu Leu Gly Phe Thr Tyr Val Gly Pro
                245                 250                 255

Ile Asp Gly His Asp Met Glu Ala Leu Leu Gln Thr Leu Arg Ala Ala
            260                 265                 270

Arg Ala Arg Thr Thr Gly Pro Val Leu Ile His Val Val Thr Lys Lys
        275                 280                 285

Gly Lys Gly Tyr Ala Pro Ala Glu Asn Ala Pro Asp Lys Tyr His Gly
290                 295                 300

Val Asn Lys Phe Asp Pro Val Thr Gly Glu Gln Lys Lys Ser Val Ala
305                 310                 315                 320

Asn Ala Pro Asn Tyr Thr Lys Val Phe Gly Ser Thr Leu Thr Glu Glu
                325                 330                 335

Ala Ala Arg Asp Pro Arg Ile Val Ala Ile Thr Ala Ala Met Pro Ser
            340                 345                 350

Gly Thr Gly Val Asp Ile Met Gln Lys Arg Phe Pro Asn Arg Val Phe
        355                 360                 365

Asp Val Gly Ile Ala Glu Gln His Ala Val Thr Phe Ala Ala Gly Leu
    370                 375                 380

Ala Gly Ala Gly Met Lys Pro Phe Cys Ala Ile Tyr Ser Ser Phe Leu
385                 390                 395                 400

Gln Arg Gly Tyr Asp Gln Ile Ala His Asp Val Ala Leu Gln Asn Leu
                405                 410                 415

Pro Val Arg Phe Val Ile Asp Arg Ala Gly Leu Val Gly Ala Asp Gly
            420                 425                 430

Ala Thr His Ala Gly Ala Phe Asp Val Gly Phe Leu Thr Ser Leu Pro
        435                 440                 445

Asn Met Thr Val Met Ala Ala Asp Glu Ala Glu Leu Ile His Met
450                 455                 460

Ile Ala Thr Ala Val Ala Phe Asp Glu Gly Pro Ile Ala Phe Arg Phe
465                 470                 475                 480

Pro Arg Gly Glu Gly Val Gly Val Glu Met Pro Glu Arg Gly Thr Val
                485                 490                 495

Leu Glu Pro Gly Arg Gly Arg Val Val Arg Glu Gly Thr Asp Val Ala
            500                 505                 510

Ile Leu Ser Phe Gly Ala His Leu His Glu Ala Leu Gln Ala Ala Lys
        515                 520                 525

Leu Leu Glu Ala Glu Gly Val Ser Val Thr Val Ala Asp Ala Arg Phe
    530                 535                 540

Ser Arg Pro Leu Asp Thr Gly Leu Ile Asp Gln Leu Val Arg His His
545                 550                 555                 560

Ala Ala Leu Val Thr Val Glu Gln Gly Ala Met Gly Gly Phe Gly Ala
                565                 570                 575
```

```
His Val Met His Tyr Leu Ala Asn Ser Gly Gly Phe Asp Gly Gly Leu
            580                 585                 590

Ala Leu Arg Val Met Thr Leu Pro Asp Arg Phe Ile Glu Gln Ala Ser
        595                 600                 605

Pro Glu Asp Met Tyr Ala Asp Ala Gly Leu Arg Ala Glu Asp Ile Ala
    610                 615                 620

Ala Thr Ala Arg Gly Ala Leu Ala Arg Gly Arg Val Met Pro Leu Arg
625                 630                 635                 640

Gln Thr Ala Lys Pro Arg Ala Val
                645
```

<210> SEQ ID NO 29
<211> LENGTH: 1944
<212> TYPE: DNA
<213> ORGANISM: Rhodobacter sphaeroides
<220> FEATURE:
<221> NAME/KEY: CDS
<222> LOCATION: (1)..(1944)

<400> SEQUENCE: 29

```
atg acc aat ccc acc ccg cga ccc gaa acc ccg ctt ttg gat cgc gtc      48
Met Thr Asn Pro Thr Pro Arg Pro Glu Thr Pro Leu Leu Asp Arg Val
 1               5                  10                  15 tgc tgc ccg gcc gac atg aag gcg ctg agt gac gcc gaa ctg gag cgg      96
Cys Cys Pro Ala Asp Met Lys Ala Leu Ser Asp Ala Glu Leu Glu Arg
                20                  25                  30 ctg gcc gac gaa gtg cgt tcc gag gtg att tcg gtc gtt gcc gag acg     144
Leu Ala Asp Glu Val Arg Ser Glu Val Ile Ser Val Val Ala Glu Thr
            35                  40                  45 gga gga cat ctg ggg tcc tcg ctg ggg gtg gtc gag ctg acc gtc gcg     192
Gly Gly His Leu Gly Ser Ser Leu Gly Val Val Glu Leu Thr Val Ala
        50                  55                  60 ctg cat gca gtc ttc aac acg ccc acc gac aag ctc gtc tgg gac gtg     240
Leu His Ala Val Phe Asn Thr Pro Thr Asp Lys Leu Val Trp Asp Val
 65                  70                  75                  80 ggc cac cag tgc tac ccc cac aag atc ctc acc ggc cgg cgc gag cag     288
Gly His Gln Cys Tyr Pro His Lys Ile Leu Thr Gly Arg Arg Glu Gln
                85                  90                  95 atg cgc acc ctg cgc cag aag ggc ggc ctc tcg ggc ttc acc aag cgc     336
Met Arg Thr Leu Arg Gln Lys Gly Gly Leu Ser Gly Phe Thr Lys Arg
                100                 105                 110 tcg gaa tcc gcc tac gac ccg ttc ggc gcg gcc cat tcc tcg acc tcg     384
Ser Glu Ser Ala Tyr Asp Pro Phe Gly Ala Ala His Ser Ser Thr Ser
            115                 120                 125 atc tcg gcc gcg ctc ggc ttt gcc atg ggc cgc gag ctg ggc caa ccc     432
Ile Ser Ala Ala Leu Gly Phe Ala Met Gly Arg Glu Leu Gly Gln Pro
        130                 135                 140 gtg ggc gac acg atc gcc gtg atc ggc gac ggc tcg atc acc gcg ggc     480
Val Gly Asp Thr Ile Ala Val Ile Gly Asp Gly Ser Ile Thr Ala Gly
145                 150                 155                 160 atg gcc tac gag gcg ctg aac cac gcg ggc cat ctg aac aag cgc ctg     528
Met Ala Tyr Glu Ala Leu Asn His Ala Gly His Leu Asn Lys Arg Leu
                165                 170                 175 ttc gtg atc ctg aac gac aat gac atg agc atc gcg ccg ccc gtg ggg     576
Phe Val Ile Leu Asn Asp Asn Asp Met Ser Ile Ala Pro Pro Val Gly
                180                 185                 190 gct ctg gcg cgc tat ctc gtg aat ctc tcg tcg aag gcg ccc ttc gcc     624
Ala Leu Ala Arg Tyr Leu Val Asn Leu Ser Ser Lys Ala Pro Phe Ala
            195                 200                 205 acg ctg cgc gcg gcc gcc gac ggg ctc gag gcc tcg ctg ccg ggg ccg     672
```

```
                    -continued

Thr Leu Arg Ala Ala Ala Asp Gly Leu Glu Ala Ser Leu Pro Gly Pro
         210                 215                 220 ctc cgc gac ggg gcg cgc cgg gcg cgc cag ctc gtg acc ggg atg ccg      720
Leu Arg Asp Gly Ala Arg Arg Ala Arg Gln Leu Val Thr Gly Met Pro
225                 230                 235                 240 ggc ggg ggc acg ctc ttc gag gag ctg ggc ttc acc tat gtg ggt ccc      768
Gly Gly Gly Thr Leu Phe Glu Glu Leu Gly Phe Thr Tyr Val Gly Pro
                245                 250                 255 atc gac ggc cac gac atg gag gcg ctg ctc cag acg ctg cgc gcg gcg      816
Ile Asp Gly His Asp Met Glu Ala Leu Leu Gln Thr Leu Arg Ala Ala
            260                 265                 270 cgg gcc cgg acc acg ggg ccg gtg ctc atc cat gtg gtc acg aag aag      864
Arg Ala Arg Thr Thr Gly Pro Val Leu Ile His Val Val Thr Lys Lys
        275                 280                 285 ggc aag ggc tac gcc cct gcc gag aat gcc ccc gac aag tat cac ggg      912
Gly Lys Gly Tyr Ala Pro Ala Glu Asn Ala Pro Asp Lys Tyr His Gly
    290                 295                 300 gtg aac aag ttc gac ccc gtc acg ggc gag cag aag aag tcg gtc gcc      960
Val Asn Lys Phe Asp Pro Val Thr Gly Glu Gln Lys Lys Ser Val Ala
305                 310                 315                 320 aac gcg ccg aac tac acc aag gtc ttc ggc tcc acc ctg acc gag gag     1008
Asn Ala Pro Asn Tyr Thr Lys Val Phe Gly Ser Thr Leu Thr Glu Glu
                325                 330                 335 gcc gcg cgc gat ccg cgc atc gtg gcc atc acc gcg gcc atg ccc tcg     1056
Ala Ala Arg Asp Pro Arg Ile Val Ala Ile Thr Ala Ala Met Pro Ser
            340                 345                 350 ggc acc ggc gtc gac atc atg cag aag cgt ttc ccg aac cgc gtc ttc     1104
Gly Thr Gly Val Asp Ile Met Gln Lys Arg Phe Pro Asn Arg Val Phe
        355                 360                 365 gac gtg ggc atc gcc gag cag cat gcc gtg acc ttc gcg gcg ggc ctt     1152
Asp Val Gly Ile Ala Glu Gln His Ala Val Thr Phe Ala Ala Gly Leu
    370                 375                 380 gcc ggg gcc ggg atg aag ccc ttc tgc gcg atc tat tcc tcg ttc ctg     1200
Ala Gly Ala Gly Met Lys Pro Phe Cys Ala Ile Tyr Ser Ser Phe Leu
385                 390                 395                 400 caa cgg ggc tac gac cag atc gcc cat gac gtg gcg ctg cag aac ctt     1248
Gln Arg Gly Tyr Asp Gln Ile Ala His Asp Val Ala Leu Gln Asn Leu
                405                 410                 415 ccc gtc cgc ttc gtg atc gac cgg gcg ggg ctc gtg ggg gcc gac ggt     1296
Pro Val Arg Phe Val Ile Asp Arg Ala Gly Leu Val Gly Ala Asp Gly
            420                 425                 430 gcg acc cat gcg ggg gcc ttc gat gtg ggc ttc ctc acg tcg ctg ccc     1344
Ala Thr His Ala Gly Ala Phe Asp Val Gly Phe Leu Thr Ser Leu Pro
        435                 440                 445 aat atg acc gtg atg gcc gcg gcc gac gag gcc gag ctc atc cac atg     1392
Asn Met Thr Val Met Ala Ala Ala Asp Glu Ala Glu Leu Ile His Met
    450                 455                 460 atc gcc acc gcc gtg gcc ttc gac gag ggc ccc att gcc ttc cgc ttc     1440
Ile Ala Thr Ala Val Ala Phe Asp Glu Gly Pro Ile Ala Phe Arg Phe
465                 470                 475                 480 ccg cgg ggc gag ggg gtg ggc gtc gag atg ccc gag cgc ggg acc gtg     1488
Pro Arg Gly Glu Gly Val Gly Val Glu Met Pro Glu Arg Gly Thr Val
                485                 490                 495 ctg gaa ccc ggc cgg ggc cgc gtg gtg cgc gag ggg acg gat gtg gcg     1536
Leu Glu Pro Gly Arg Gly Arg Val Val Arg Glu Gly Thr Asp Val Ala
            500                 505                 510 atc ctt tcc ttc ggc gcg cat ctg cac gag gcc ttg cag gcg gcg aaa     1584
Ile Leu Ser Phe Gly Ala His Leu His Glu Ala Leu Gln Ala Ala Lys
        515                 520                 525
```

| | | | | | | | | | | | | | | | |
|---|---|---|---|---|---|---|---|---|---|---|---|---|---|---|---|
| ctc | ctc | gag | gcc | gag | ggg | gtg | agc | gtg | acc | gtg | gcc | gac | gcc | cgc | ttc | 1632 |
| Leu | Leu | Glu | Ala | Glu | Gly | Val | Ser | Val | Thr | Val | Ala | Asp | Ala | Arg | Phe |
| | 530 | | | | 535 | | | | | 540 | | | | | | ctc ctc gag gcc gag ggg gtg agc gtg acc gtg gcc gac gcc cgc ttc  1632
Leu Leu Glu Ala Glu Gly Val Ser Val Thr Val Ala Asp Ala Arg Phe
    530                 535                     540 tcg cgc ccg ctc gac acg ggg ctc att gac cag ctc gtg cgc cat cac  1680
Ser Arg Pro Leu Asp Thr Gly Leu Ile Asp Gln Leu Val Arg His His
545                 550                 555                 560 gcc gcg ctg gtg acg gtg gag cag ggg gcc atg ggc ggc ttc ggc gct  1728
Ala Ala Leu Val Thr Val Glu Gln Gly Ala Met Gly Gly Phe Gly Ala
                565                 570                 575 cat gtc atg cac tat ctc gcc aat tcc ggc ggc ttc gac ggg ggc ctc  1776
His Val Met His Tyr Leu Ala Asn Ser Gly Gly Phe Asp Gly Gly Leu
            580                 585                 590 gcg ctc cgg gtc atg acg ctg ccc gac cgc ttc atc gag cag gcg agc  1824
Ala Leu Arg Val Met Thr Leu Pro Asp Arg Phe Ile Glu Gln Ala Ser
        595                 600                 605 ccc gag gac atg tat gcc gat gcg ggg ctg cgg gcc gag gat atc gcg  1872
Pro Glu Asp Met Tyr Ala Asp Ala Gly Leu Arg Ala Glu Asp Ile Ala
    610                 615                 620 gcc acc gcg cgg ggc gcg ctc gcc cgg ggg cgc gtg atg ccg ctc cgg  1920
Ala Thr Ala Arg Gly Ala Leu Ala Arg Gly Arg Val Met Pro Leu Arg
625                 630                 635                 640 cag acg gca aag ccg cgg gcg gtc  1944
Gln Thr Ala Lys Pro Arg Ala Val
                645

<210> SEQ ID NO 30
<211> LENGTH: 394
<212> TYPE: PRT
<213> ORGANISM: Rhodobacter sphaeroides

<400> SEQUENCE: 30

Met Arg Ser Leu Ser Ile Phe Gly Ala Thr Gly Ser Ile Gly Glu Ser
1               5                   10                  15

Thr Phe Asp Leu Val Met Arg Lys Gly Gly Pro Glu Ala Phe Arg Thr
            20                  25                  30

Val Ala Leu Thr Gly Gly Arg Asn Ile Arg Arg Leu Ala Glu Met Ala
        35                  40                  45

Arg Ala Leu Lys Ala Glu Leu Ala Val Thr Ala His Glu Asp Cys Leu
    50                  55                  60

Pro Ala Leu Arg Glu Ala Leu Ala Gly Thr Gly Thr Glu Val Ala Gly
65                  70                  75                  80

Gly Ala Gln Ala Ile Ala Glu Ala Ala Asp Arg Pro Ala Asp Trp Thr
                85                  90                  95

Met Ser Ala Ile Val Gly Ala Ala Gly Leu Val Pro Gly Met Arg Ala
            100                 105                 110

Leu Lys His Gly Arg Thr Leu Ala Leu Ala Asn Lys Glu Ser Leu Val
        115                 120                 125

Thr Ala Gly Gln Leu Leu Met Arg Thr Ala Gln Glu Asn Gly Ala Thr
    130                 135                 140

Ile Leu Pro Val Asp Ser Glu His Ser Ala Val Phe Gln Ala Leu Ala
145                 150                 155                 160

Gly Glu Asp Thr Ala Cys Val Glu Arg Val Ile Ile Thr Ala Ser Gly
                165                 170                 175

Gly Pro Phe Arg Asp Trp Ser Leu Glu Arg Ile Arg Ala Cys Thr Val
            180                 185                 190

Ala Glu Ala Gln Ala His Pro Asn Trp Ser Met Gly Gln Arg Ile Ser
        195                 200                 205

```
Ile Asp Ser Ala Ser Met Phe Asn Lys Ala Leu Glu Leu Ile Glu Thr
210                 215                 220

Arg Glu Phe Phe Gly Phe Glu Pro Asp Arg Ile Glu Ala Val Val His
225                 230                 235                 240

Pro Gln Ser Ile Val His Ala Met Val Gly Phe Cys Asp Gly Gly Leu
                245                 250                 255

Met Ala His Leu Gly Pro Ala Asp Met Arg His Ala Ile Gly Phe Ala
            260                 265                 270

Leu Asn Trp Pro Gly Arg Gly Glu Val Pro Val Ala Arg Ile Asp Leu
        275                 280                 285

Ala Gln Ile Ala Ser Leu Thr Phe Gln Lys Pro Asp Glu Glu Arg Phe
290                 295                 300

Pro Ala Leu Arg Leu Ala Arg Asp Val Met Ala Ala Arg Gly Leu Ser
305                 310                 315                 320

Gly Ala Ala Phe Asn Ala Ala Lys Glu Ile Ala Leu Asp His Phe Ile
                325                 330                 335

Ala Gly Arg Ile Gly Phe Leu Asp Met Ala Ala Val Val Glu Glu Thr
            340                 345                 350

Leu Ala Gly Val Ser Thr Asp Pro Leu Phe Gly Lys Val Pro Asp Ala
        355                 360                 365

Leu Glu Glu Val Leu Ala Met Asp His Leu Ala Arg Arg Ala Ala Glu
370                 375                 380

Glu Ala Ala Gly Leu Arg Gln Gln Lys Arg
385                 390

<210> SEQ ID NO 31
<211> LENGTH: 1182
<212> TYPE: DNA
<213> ORGANISM: Rhodobacter sphaeroides
<220> FEATURE:
<221> NAME/KEY: CDS
<222> LOCATION: (1)..(1182)

<400> SEQUENCE: 31 atg cgc agc ctg tcg atc ttt ggg gcc acc ggc tcc atc ggc gaa tcc      48
Met Arg Ser Leu Ser Ile Phe Gly Ala Thr Gly Ser Ile Gly Glu Ser
1               5                   10                  15 acc ttc gac ctc gtc atg cgg aag ggc ggg ccc gag gcg ttc cgc acc      96
Thr Phe Asp Leu Val Met Arg Lys Gly Gly Pro Glu Ala Phe Arg Thr
                20                  25                  30 gtc gct ctg acc ggc ggg cgc aac atc cgg cga ctg gcc gaa atg gcg     144
Val Ala Leu Thr Gly Gly Arg Asn Ile Arg Arg Leu Ala Glu Met Ala
            35                  40                  45 cgt gcg ctg aag gcg gag ctt gcc gtc acc gcg cat gag gac tgc ctg     192
Arg Ala Leu Lys Ala Glu Leu Ala Val Thr Ala His Glu Asp Cys Leu
        50                  55                  60 ccc gcg ctg cgc gag gcg ctg gcc ggg acg ggc acc gag gtc gcg ggc     240
Pro Ala Leu Arg Glu Ala Leu Ala Gly Thr Gly Thr Glu Val Ala Gly
65                  70                  75                  80 ggg gcg cag gcc atc gcc gag gcc gcc gac cgg ccg gcc gac tgg acc     288
Gly Ala Gln Ala Ile Ala Glu Ala Ala Asp Arg Pro Ala Asp Trp Thr
                85                  90                  95 atg tcg gcc atc gtg ggc gcc gcg ggc ctc gtg ccc gga atg cgg gcg     336
Met Ser Ala Ile Val Gly Ala Ala Gly Leu Val Pro Gly Met Arg Ala
                100                 105                 110 ctg aag cac ggc cgc acg ctg gcg ctc gcc aac aag gaa agc ctc gtg     384
Leu Lys His Gly Arg Thr Leu Ala Leu Ala Asn Lys Glu Ser Leu Val
            115                 120                 125
```

```
acg gca ggg caa ctc ctg atg cgg acg gcc cag gag aac ggc gcc acg    432
Thr Ala Gly Gln Leu Leu Met Arg Thr Ala Gln Glu Asn Gly Ala Thr
    130             135                 140 atc ctg ccg gtg gac agc gag cac tcc gcg gtc ttt cag gcg ctg gcg    480
Ile Leu Pro Val Asp Ser Glu His Ser Ala Val Phe Gln Ala Leu Ala
145                 150                 155                 160 ggc gag gac acg gcc tgc gtc gag cgc gtc atc atc acg gcg tcc ggc    528
Gly Glu Asp Thr Ala Cys Val Glu Arg Val Ile Ile Thr Ala Ser Gly
                165                 170                 175 ggg ccg ttc cgc gac tgg agc ctc gag cgc atc cgc gcc tgc acc gtg    576
Gly Pro Phe Arg Asp Trp Ser Leu Glu Arg Ile Arg Ala Cys Thr Val
            180                 185                 190 gcc gag gcg cag gcc cat ccc aac tgg tcc atg ggc cag cgg atc tcc    624
Ala Glu Ala Gln Ala His Pro Asn Trp Ser Met Gly Gln Arg Ile Ser
        195                 200                 205 atc gac agc gcc tcg atg ttc aac aag gcg ctc gag ctg atc gag acg    672
Ile Asp Ser Ala Ser Met Phe Asn Lys Ala Leu Glu Leu Ile Glu Thr
    210                 215                 220 cgc gaa ttc ttc ggc ttc gag ccg gac cgg atc gag gcg gtc gtc cat    720
Arg Glu Phe Phe Gly Phe Glu Pro Asp Arg Ile Glu Ala Val Val His
225                 230                 235                 240 ccg caa tcc atc gtc cat gcg atg gtg ggc ttc tgc gac ggg ggc ctg    768
Pro Gln Ser Ile Val His Ala Met Val Gly Phe Cys Asp Gly Gly Leu
                245                 250                 255 atg gcc cat ctc ggc ccc gcc gac atg cgc cac gcc atc gga ttc gcg    816
Met Ala His Leu Gly Pro Ala Asp Met Arg His Ala Ile Gly Phe Ala
            260                 265                 270 ctg aac tgg ccg ggt cgc ggc gag gtg ccc gtc gcc cgg atc gac ctc    864
Leu Asn Trp Pro Gly Arg Gly Glu Val Pro Val Ala Arg Ile Asp Leu
        275                 280                 285 gca cag att gcg agc ctc acc ttc cag aag cct gac gag gaa cgc ttt    912
Ala Gln Ile Ala Ser Leu Thr Phe Gln Lys Pro Asp Glu Glu Arg Phe
    290                 295                 300 ccg gcc ctg agg ctt gcg cga gac gtc atg gcg gcg cgc ggc ctg tcg    960
Pro Ala Leu Arg Leu Ala Arg Asp Val Met Ala Ala Arg Gly Leu Ser
305                 310                 315                 320 ggc gcc gcc ttc aac gcg gcc aag gag atc gcg ctc gat cat ttc atc   1008
Gly Ala Ala Phe Asn Ala Ala Lys Glu Ile Ala Leu Asp His Phe Ile
                325                 330                 335 gcc gga cgc atc ggg ttt ctg gac atg gcg gcg gtg gtc gag gag acg   1056
Ala Gly Arg Ile Gly Phe Leu Asp Met Ala Ala Val Val Glu Glu Thr
            340                 345                 350 ctc gcg ggc gtt tcg acc gac ccc ctg ttc gga aaa gtg ccc gac gcc   1104
Leu Ala Gly Val Ser Thr Asp Pro Leu Phe Gly Lys Val Pro Asp Ala
        355                 360                 365 ctt gag gaa gtg ctg gcc atg gac cat ctc gct cgg aga gcg gca gag   1152
Leu Glu Glu Val Leu Ala Met Asp His Leu Ala Arg Arg Ala Ala Glu
    370                 375                 380 gaa gcc gcc ggt ctc cgc cag cag aaa agg                           1182
Glu Ala Ala Gly Leu Arg Gln Gln Lys Arg
385                 390
```

<210> SEQ ID NO 32
<211> LENGTH: 23
<212> TYPE: DNA
<213> ORGANISM: Artificial Sequence
<220> FEATURE:
<223> OTHER INFORMATION: Synthetic DNA

<400> SEQUENCE: 32
aagctgatct gggacgtggg gca                                          23

```
<210> SEQ ID NO 33
<211> LENGTH: 23
<212> TYPE: DNA
<213> ORGANISM: Artificial Sequence
<220> FEATURE:
<223> OTHER INFORMATION: Synthetic DNA

<400> SEQUENCE: 33
tgctatccgc acaagatcct gac                                          23

<210> SEQ ID NO 34
<211> LENGTH: 23
<212> TYPE: DNA
<213> ORGANISM: Artificial Sequence
<220> FEATURE:
<223> OTHER INFORMATION: Synthetic DNA

<400> SEQUENCE: 34
gcatgctgtt ccgcgatgcc gac                                          23
```

US 7,132,268 B2

PROCESS FOR PRODUCING ISOPRENOID COMPOUNDS BY MICROORGANISMS AND A METHOD FOR SCREENING COMPOUNDS WITH ANTIBIOTIC OR WEEDING ACTIVITY

This application is a Divisional of application Ser. No. 09/673,198 filed Oct. 12, 2000, now U.S. Pat. No. 6,806,076.

TECHNICAL FIELD

The present invention relates to a method for producing isoprenoid compounds using a transformant derived from a prokaryote; and a method for screening substances having antibiotic or weeding activity involved in a non-mevalonate pathway.

BACKGROUND ART

Isoprenoid is a general term for compounds having isoprene unit consisting of 5 carbon atoms as a backbone structure. Isoprenoid is biosynthesized by polymerization of isopentenyl pyrophosphate (IPP). Various kinds of isoprenoid compounds are present in nature and many of them are useful for humans.

For example, ubiquinone plays an important role in vivo as an essential component of the electron transport system. The demand for ubiquinone is increasing not only as a pharmaceutical effective against cardiac diseases, but also as a health food in Western countries.

Vitamin K, an important vitamin involved in the blood coagulation system, is utilized as a hemostatic agent. Recently it has been suggested that vitamin K is involved in osteo-metabolism, and is expected to be applied to the treatment of osteoporosis. Phylloquinone and menaquinone have been approved as pharmaceuticals.

In addition, ubiquinone and vitamin K are effective in inhibiting barnacles from clinging to objects, and so would make an excellent additive to paint products to prevent barnacles from clinging.

Further, compounds called carotenoids having an isoprene backbone consisting of 40 carbon atoms have antioxidant effect. Carotenoids such as β-carotene, astaxanthin, and cryptoxanthin are expected to possess cancer preventing and immunopotentiating activity.

As described above, isoprenoid compounds include many effective substances. Establishment of an economical process for producing these substances will be a huge benefit to the medical world and society.

The process for producing isoprenoid compounds through fermentation has already been examined, and examination of culture conditions, strain breeding by mutagenesis, and improvement of yield by genetic engineering tehniques have been tested. However, the practical results are limited to individual types of compounds, and there is no known method effective for the isoprenoid compounds in general.

Isopentenyl pyrophosphate (IPP), a backbone unit of isoprenoid compounds, has been proved to be biosynthesized from acetyl-CoA via mevalonic acid (mevalonate pathway) in eukaryotes, such as an animal and yeast.

3-Hydroxy-3-methylglutaryl-CoA (HMG-COA) reductase is considered to be a rate-limiting enzyme in the mevalonate pathway [Mol. Biol. Cell, 5, 655 (1994)]. A test in yeast to improve the yield of carotenoids by overexpression of HMG-CoA reductase has been conducted [Misawa, et al., Summaries of Lectures on Carotenoids, 1997].

There is no knowledge which proves the presence of the mevalonate pathway in prokaryotes. In many prokaryotes, another pathway, the non-mevalonate pathway, has been found in which IPP is biosynthesized via 1-deoxy-D-xylulose 5-phosphate produced by condensation of pyruvic acid and glyceraldehyde 3-phosphate [Biochem. J., 295, 517 (1993)]. It is suggested that 1-deoxy-D-xylulose5-phosphate is converted to IPP via 2-C-methyl-D-erythritol 4-phosphate in an experiment using $^{13}$C-labelled substrate [Tetrahedron Lett 38, 4769 (1997)].

In *Escherichia coli*, a gene encoding an enzyme, 1-deoxy-D-xylulose 5-phosphate synthase (DXS) which allows biosynthesis of 1-deoxy-D-xylulose 5-phosphate by condensation of pyruvic acid and glyceraldehyde 3-phosphate, is identified [Proc. Natl. Acad. Sci. USA, 94, 12857 (1997)]. Said gene is contained in an operon consisting of four ORFs that include ispA encoding farnesyl pyrophosphate synthase.

Further in *Escherichia coli*, the presence of the activity to convert 1-deoxy-D-xylulose 5-phosphate to 2-C-methyl-D-erythritol 4-phosphate is known [Tetrahedron Lett 39, 4509 (1998)].

At present there are no known description nor suggestion to improve yield of an isoprenoid compound by genetically engineering these genes contained in the operon.

Although knowledge about the non-mevalonate pathway in prokaryotes has gradually increased, most enzymes involved therein and genes encoding these enzymes still remain unknown.

In photosynthetic bacteria, there is a known process for effectively producing ubiquinone-10 by introducing a gene for an enzyme ubiC (uviC gene), which converts chorismate into 4-hydroxybenzoate, and a gene for p-hydroxybenzoate transferase (ubiA) (Japanese Unexamined Patent Application 107789/96). However, there is no example which improved the productivity of isoprenoid compounds by genetically engineering genes for enzymes involved in the non-mevalonate pathway.

Moreover, there is no knowledge about how prokaryotes will be influenced when the reaction on the non-mevalonate pathway is inhibited by mutagenesis or treating with drugs.

DISCLOSURE OF THE INVENTION

The object of this invention is to provide a process for producing isoprenoid compounds comprising integrating DNA into a vector wherein the DNA contains one or more DNA involved in biosynthesis of isoprenoid compounds useful in pharmaceuticals for cardiac diseases, osteoporosis, homeostasis, prevention of cancer, and immunopotentiation, health food and anti-fouling paint products against barnacles, introducing the resultant recombinant DNA into a host cell derived from prokaryotes, culturing the obtained transformant in a medium, allowing the transformant to produce and accumulate isoprenoid compounds in the culture, and recovering the isoprenoid compounds from said culture; a process for producing proteins comprising integrating DNA into a vector wherein the DNA contains one or more DNA encoding a protein having activity to improve efficiency in the biosynthesis of isoprenoid compounds, introducing the resultant recombinant DNA into a host cell, culturing the obtained transformant in a medium, allowing the transformant to produce and accumulate said protein in the culture, and recovering said protein from the culture; the protein, and DNA encoding the protein. A further object of this invention is to provide a method of screening a substance having antibiotic and/or weeding activities, which comprises screening the substance inhibiting enzymatic reaction on the non-mevalonic acid pathway.

The inventors have completed the invention by finding that the productivity of isoprenoid can be improved by screening DNA capable of improving the productivity for isoprenoid in prokaryotes, and introducing the obtained DNA into prokaryotes.

That is, the first invention of the present application is a process for producing isoprenoid compounds comprising integrating DNA into a vector wherein the DNA contains one or more DNA selected from the following (a), (b), (c), (d), (e) and (f):

(a) a DNA encoding a protein having activity to catalyze a reaction to produce 1-deoxy-D-xylulose 5-phosphate from pyruvic acid and glyceraldehyde 3-phosphate,
(b) a DNA encoding farnesyl pyrophosphate synthase,
(c) a DNA encoding a protein that has an amino acid sequence of SEQ ID NO:3, or a protein that has an amino acid sequence wherein one to several amino acid residues are deleted, substituted or added in the amino acid sequence of SEQ ID NO: 3 and has activity to improve efficiency in the biosynthesis of isoprenoid compounds,
(d) a DNA encoding a protein that has an amino acid sequence of SEQ ID NO:4, or a protein that has an amino acid sequence wherein one to several amino acid residues are deleted, substituted or added in the amino acid sequence of SEQ ID NO: 4 and has activity to improve efficiency in the biosynthesis of isoprenoid compounds,
(e) a DNA encoding a protein having activity to catalyze a reaction to produce 2-C-methyl-D-erythritol 4-phosphate from 1-deoxy-D-xylulose 5-phosphate, and
(f) a DNA encoding a protein that can hybridize under stringent conditions with DNA selected from (a), (b), (c), (d) and (e), and has activity substantially identical with that of the protein encoded by the selected DNA;

introducing the resultant recombinant DNA into a host cell derived from prokaryotes, culturing the obtained transformant in a medium; allowing the transformant to produce and accumulate isoprenoid compounds in the culture; and recovering the isoprenoid compounds from the culture.

Deletions, substitutions or additions of amino acid residues in this specification can be carried out by site-directed mutagenesis, which is a technique well-known prior to the filing of this application. Further, the phrase "one to several amino acid residues" means the number of amino acid residues, which can be deleted, substituted, or added by site-directed mutagenesis, for example, 1 to 5 amino acid residues.

The protein consisting of an amino acid sequence, which has deletion, substitution or addition of one to several amino acid residues, can be prepared according to the methods described in Molecular Cloning: A Laboratory Manual, Second Edition, ed. Sambrook, Fritsch, and Maniatis, Cold Spring Harbor Laboratory Press, 1989 (hereinafter referred to as Molecular Cloning, Second Edition), Current Protocols in Molecular Biology, John Wiley & Sons (1987–1997), Nucleic Acids Research, 10, 6487 (1982), Proc. Natl. Acad. Sci., USA, 79, 6409 (1982), Gene, M, 315 (1985), Nucleic Acids Research, 13, 4431 (1985), and Proc. Natl. Acad. Sci USA, 82, 488 (1985), etc.

The above-mentioned DNA encoding a protein, which catalyzes a reaction to produce 1-deoxy-D-xylulose 5-phosphate from pyruvic acid and glyceraldehyde 3-phosphate, is for example, a DNA encoding a protein, which has an amino acid sequence of SEQ ID NO:1, 26 or 28, or a DNA encoding a protein which has an amino acid sequence wherein one to several amino acid residues are deleted, substituted or added in the amino acid sequence of SEQ ID NO: 1, 26, or 28 and has activity to catalyze a reaction to produce 1-deoxy-D-xylulose 5-phosphate from pyruvic acid and glyceraldehyde 3-phosphate.

Examples of such a DNA include a DNA having an nucleotide sequence of SEQ ID NO:6 or a DNA having a nucleotide sequence of SEQ ID NO:27 or 29.

Examples of a DNA encoding farnesyl pyrophosphate synthase include a DNA encoding a protein having an amino acid sequence of SEQ ID NO:2 or a DNA encoding a protein, which has an amino acid sequence wherein one to several amino acid residues are deleted, substituted or added in the amino acid sequence of SEQ ID NO: 2 and has enzymatic activity to produce farnesyl pyrophosphate. A specific example is a DNA having a nucleotide sequence of SEQ ID NO:7.

A specific example of the DNA encoding a protein having an amino acid sequence of SEQ ID NO:3 is a DNA having a nucleotide sequence of SEQ ID NO:8.

Further a specific example of the DNA encoding a protein having an amino acid sequence of SEQ ID NO:4 is a DNA having a nucleotide sequence of SEQ ID NO:9.

Examples of the DNA encoding a protein having activity to catalyze a reaction to produce 2-C-methyl-D-erythritol 4-phosphate from 1-deoxy-D-xylulose 5-phosphate include a DNA encoding a protein, which has an amino acid sequence of SEQ ID NO:5 or 30, or a DNA encoding a protein, which has an amino acid sequence wherein one to several amino acid residues are deleted, substituted or added in the amino acid sequence of SEQ ID NO: 5 or 30 and has activity to catalyze the reaction to produce 2-C-methyl-D-erythritol 4-phosphate from 1-deoxy-D-xylulose 5-phosphate.

Specifically, such a DNA is one having a nucleotide sequence of SEQ ID NO:10 or 31.

The above phrase "DNA . . . that can hybridize under stringent conditions" means a DNA that can be obtained by colony hybridization, plaque hybridization, Southern Blotting or the like using the above DNA or fragments of the DNA as a probe. Such a DNA can be identified by performing hybridization using a filter with colony- or plaque-derived DNA, or fragments of the DNA immobilized thereon, in the presence of 0.7 to 1.0 mol/l NaCl at 65° C., followed by washing the filter using about 0.1 to 2-fold SSC solution (the composition of SSC solution at 1-fold concentration is consisted of 150 mol/l sodium chloride, 15 mol/l sodium citrate) at 65° C.

Hybridization can be carried out according to the methods described in Molecular Cloning, Second Edition. Examples of DNA capable of hybridizing include a DNA that shares at least 70% or more homology, preferably, 90% or more homology with a nucleotide sequence selected from SEQ ID NOS:1, 2, 3, 4, and 5.

Examples of isoprenoid compounds include ubiquinone, vitamin $K_2$, and carotenoids.

The second invention of this application is a protein having activity to improve efficiency in the biosynthesis of isoprenoid compounds and selected from the following (a), (b) and (c):

(a) a protein having an amino acid sequence of SEQ ID NO:3, or a protein having an amino acid sequence wherein one to several amino acid residues are deleted, substituted or added in the amino acid sequence of SEQ ID NO: 3
(b) a protein having an amino acid sequence of SEQ ID NO:4, or a protein having an amino acid sequence wherein one to several amino acid residues are deleted, substituted or added in the amino acid sequence of SEQ ID NO: 4, and
(c) a protein having an amino acid sequence of SEQ ID NO:5, or a protein having an amino acid sequence wherein one to several amino acid residues are deleted, substituted or added in the amino acid sequence of SEQ ID NO: 5.

The third invention of this application is a process for producing a protein having activity to improve efficiency in the biosynthesis of isoprenoid compounds comprising integrating DNA encoding the protein described in the second invention above into a vector, introducing the resultant recombinant DNA into a host cell culturing the obtained transformant in a medium, allowing the transformant to produce and accumulate the protein in the culture, and recovering the protein from the culture.

The transformants above include microorganisms belonging to the genus Eschenchia, Rhodobacter or Erwinia.

The fourth invention of this application is a DNA encoding a protein having activity to improve efficiency in the biosynthesis of isoprenoid compounds selected from the following (a), (b), (c), (d), (e), (f) and (g):
(a) a DNA encoding a protein having an amino acid sequence of SEQ ID NO:3,
(b) a DNA encoding a protein having an amino acid sequence of SEQ ID NO:4,
(c) a DNA encoding a protein having an amino acid sequence of SEQ ID NO:5,
(d) a DNA having a nucleotide sequence of SEQ ID NO:8,
(e) a DNA having a nucleotide sequence of SEQ ID NO:9,
(f) a DNA having a nucleotide sequence of SEQ ID NO:10, and
(g) a DNA that can hybridize with any one of DNA described in (a) to (f) under stringent conditions.

The fifth invention of this application is a method for screening a substance having antibiotic activity comprising screening a substance that inhibits the reaction of a protein having activity of an enzyme selected from those present on the non-mevalonate pathway in which 1-deoxy-D-xylulose 5-phosphate biosynthesized from pyruvic acid and glyceraldehyde 3-phosphate is converted to 2-C-methyl-D-erythritol 4-phosphate from which isopentenyl pyrophosphate is biosynthesized.

The sixth invention of this application is a method for screening a substance having weeding activity comprising screening a substance that inhibits the reaction of a protein having activity of an enzyme selected from those present on the non-mevalonate pathway in which 1-deoxy-D-xylulose 5-phosphate biosynthesized from pyruvic acid and glyceraldehyde 3-phosphate is converted to 2-C-methyl-D-erythritol 4-phosphate from which isopentenyl pyrophosphate is biosynthesized.

Examples of the proteins in the fifth and sixth inventions above include a protein of the following (a) or (b):
(a) a protein having activity to catalyze a reaction to produce 1-deoxy-D-xylulose 5-phosphate from pyruvic acid and glyceraldehyde 3-phosphate, or
(b) a protein having activity to catalyze a reaction to produce 2-C-methyl-D-erythritol 4-phosphate from 1-deoxy-D-xylulose 5-phosphate.

Examples of the proteins catalyzing the reaction to produce 1-deoxy-D-xylulose 5-phosphate from pyruvic acid and glyceraldehyde 3-phosphate include a protein having an amino acid sequence of SEQ ID NO:1, or a protein having an amino acid sequence wherein one to several amino acid residues are deleted, substituted or added in the amino acid sequence of SEQ ID NO: 1, and having activity to catalyze 1-deoxy-D-xylulose 5-phosphate from pyruvic acid and glyceraldehyde 3-phosphate.

Examples of the proteins having activity to catalyze the reaction to produce 2-C-methyl-D-erythritol 4-phosphate from 1-deoxy-D-xylulose 5-phosphate include a protein having an amino acid sequence of SEQ ID NO:5, or a protein having an amino acid sequence wherein one to several amino acid residues are deleted, substituted or added in the amino acid sequence of SEQ ID NO: 5, and having activity to catalyze the reaction to produce 2-C-methyl-D-erythritol 4-phosphate from 1-deoxy-D-xylulose 5-phosphate.

The seventh invention of this invention is a substance, which has antibiotic activity and is obtained by the screening method in the fifth invention above. Known substances obtained by the above screening method are not included in this invention.

The inventors have focused on structural similarity of fosmidomycin [3-(N-formyl-N-hydroxyamino) propylphosphonic acid] to 2-C-methyl-D-erythritol 4-phosphate, a reaction product from 1-deoxy-D-xylulose 5-phosphate reductoisomerase reaction, or a reaction intermediate assumed to be produced in this enzymatic reaction. Based on the assumption that fosmidomycin has activity to inhibit 1-deoxy-D-xylulose 5-phosphate reductoisomerase and antibiotic activity, the inventors have conducted experiments on the screening method of the fifth invention and also described in the following Example 10. As a result, the inventors found that fosmidomycin is a substance having the activity to inhibit 1-deoxy-D-xylulose 5-phosphate reductoisomerase and antibiotic activity, and in addition, verified the adequacy of the screening method of the fifth invention above. However, known compound fosmidomycin is excluded from this invention.

The eighth invention of this invention is a substance, which has weeding activity and obtained through the screening method of the sixth invention above. As described above, any substance that is obtained from the screening method and already known is excluded from this invention.

Hereinafter a more detailed explanation of this invention will be given.

I. Cloning of DNA Encoding a Protein Involved in Biosynthesis of Isoprenoid Compounds (1) Cloning of DNA Encoding a Protein Involved in Biosynthesis of Isoprenoid Compounds Using a Nucleotide Sequence of DNA (DXS Gene) Encoding DXS Using information on previously-determined nucleotide sequences of E.coli chromosome and DXS gene [Proc. Natl. Acad. Sci. USA., 94, 12857 (1997)], a DNA region containing DXS gene or genes neighboring DXS gene is obtained by cloning with PCR method from E.coli [Science, 230, 1350 (1985)].

An example of information on a nucleotide sequence containing DXS gene is the nucleotide sequence of SEQ ID NO:11.

A concrete example of methods for cloning the DNA region containing DXS gene is as follows.

Escherichia coli, such as an E.coli XL1-Blue strain (available from TOYOBO CO., LTD.), is cultured in a suitable medium for Escherichia coli, for example, LB liquid medium [containing 10 g of Bactotrypton (manufactured by Difco Laboratories), 5 g of Yeast extracts (manufactured by Difco Laboratories), 5 g of NaCl per liter of water, and adjusted to pH 7.2] according to standard techniques.

After culturing, cells were recovered from the culture by centrifugation.

Chromosomal DNA is isolated from the obtained cells according to a known method, described in, for example, Molecular Cloning, Second Edition.

Using information on a nucleotide sequence of SEQ ID NO:11, a sense primer and an antisense primer, which contain DXS gene or a nucleotide sequence corresponding to the DNA region of genes neighboring DXS gene, are synthesized with a DNA synthesizer.

To introduce the amplified DNA fragments into a plasmid after amplification with PCR, it is preferable to add recognition sites appropriate for restriction enzymes, e.g., BamHI, and EcoRI to the 5' ends of sense and antisense primers.

Examples of a combination of the sense and antisense primers include a DNA having a combination of nucleotide sequences: SEQ ID NOS: 12 and 13, SEQ ID NOS: 14 and 15, SEQ ID NOS: 12 and 16, SEQ ID NOS: 17 and 18, SEQ ID NOS: 19 and 13, or SEQ ID NOS: 22 and 23.

Using the chromosomal DNA as a template, PCR is carried out with DNA Thermal Cycler (manufactured by Perkin Elmer Instruments, Inc. Japan) using the primers; TaKaRa LA-PCR™ Kit Ver. 2 (manufactured by TAKARA SHUZO CO., LTD.) or Expand™ High-Fidelity PCR System (manufactured by Boehringer Manheim K.K.)

In a reaction condition for PCR, PCR is carried out by 30 cycles, in the case of amplifying a DNA fragment of 2 kb or less, one cycle consisting of reaction at 94° C. for 30 seconds, 55° C. for 30 seconds to 1 minute, and 72° C. for 2 minutes; in the case of amplifying a DNA fragment of more than 2 kb, one cycle consisting of reaction at 98° C. for 20 seconds, and 68° C. for 3 minutes; then followed by the reaction at 72° C. for 7 minutes.

The amplified DNA fragments are cut at sites the same as the restriction enzyme sites added to the above primers, and are fractionated and collected by using agarose gel electrophoresis, sucrose density-gradient centrifugation and the like.

For cloning the amplified DNA obtained above, an appropriate cloning vector is digested with restriction enzymes creating the cohensive ends which are able to ligate with the amplified DNA fragment. Using a recombinant DNA obtained by ligating the above amplified DNA with the cloning vector. *Escherichia coli*, e.g., *E coli* DH5 α (available from TOYOBO CO., LTD.) is transformed.

As a cloning vector for cloning the amplified DNA, any cloning vectors includina phage vectors and plasmic vectors, which can autonomously replicate in *E coli* K12. can be used. Expression vectors for *E.coli* can be used as cloning vectors. Concrete examples of the cloning vectors include ZAP Express [manufactured by Stratagene, Strategies, 5, 58 (1992)], pBluescript II SK(+) [Nucleic Acids Research, 17, 9494 (1989)], Lamdba ZAP II (manufactured by Stratagene, λgt10, λgt11 (DNA Cloning, A Practical Approach, 1, 49 (1985)), λTriplEx (manufactured by Clonetec), λExCell (manufactured by Pharmacia), pT7T318U (manufactured by Pharmacia), pcD2 [H.Okayama and P. Berg; Mol. Cell. Biol., 3 280 (1983)], pMW218 (manufactured by WAKO PURE CHEMICAL INDUSTRIES, LTD), pUC118 (manufactured by TAKARA SHUZO CO., LTD.), pEG400 [J. Bac., 172, 2392 (1990)], and pQE-30 (manufactured by Qiagen, Inc.).

A plasmid DNA containing a DNA of interest can be obtained from the resultant transformant according to standard techniques, such as those described in Molecular Cloning, Second Edition, Current Protocols in Molecular Biology, Supplement 1 to 38, John Wiley & Sons (1987–1997), DNA Cloning 1: Core Techniques, A Practical Approach, Second Edition, Oxford University Press (1995).

A plasmid DNA containing a DNA encoding a protein having activity to catalyze the reaction to produce 1-deoxy-D-xylulose 5-phosphate from pyruvic acid and glyceraldehyde 3-phosphate, a DNA encoding farnesyl pyrophosphate synthase, a DNA encoding a protein having an amino acid sequence of SEQ ID NO:3, a DNA encoding a protein having an amino acid sequence of SEQ ID NO:4 or the like; and a plasinid DNA containing one or more DNAs above, can be obtained by the above methods.

Such plasmids include plasmid pADO-1 that contains all of the DNA above, plasmid pDXS-1 or PQEDXS-1 that contains a DNA having a nucleotide sequence of SEQ ID NO:6, plasmid pISP-1 that contains a DNA having a nucleotide sequence of SEQ ID NO:7, plasmid pXSE-1 that contains a DNA having a nucleotide sequence of SEQ ID NO:8, and plasmid pTFE-1 that contains a DNA having a nucleotide sequence of SEQ ID NO:9.

Using the nucleotide sequences of DNA fragments derived from *E.coli*, which have been inserted into these plasmids, homologues of the DNA can be obtained from other prokaryotes, such as microorganisms belonging to the genus *Rhodobacter*, in the same manner as described above.

(2) Cloning of DNA Encoding a Protein Having Activity to Complement Methylerythritol-requiring Mutant of *E.coli* (Gene Complementing Methylerythritol-requiring Mutant)

① Construction of *E.coli* Methylerythritol-requiring Mutant

*Escherichia coli*, such as *E.coli* W3110 (ATCC14948), is cultured according to standard techniques.

After culturing, cells are recovered from the obtained culture by centrifugation.

The obtained cells are washed with an appropriate buffer agent, such as 0.05 mol/l Tris-maleate buffer (pH 6.0). Then the cells are suspended in the same buffer such that the cell density is $10^4$ to $10^{10}$ cells/ml.

Mutagenesis is carried out by standard techniques using the suspension. In such a standard technique, for example, NTG is added to the suspension to a final concentration of 600 mg/l, and then the mixture is maintained for 20 minutes at room temperature.

This suspension after mutagenesis is spread on minimal agar medium supplemented with 0.05 to 0.5% methylerythritol and cultured.

An example of minimal agar medium is M9 medium (Molecular Cloning, Second Edition) supplemented with agar.

Methylerythritol that is chemically synthesized according to the method described in Tetrahedron Letters, 38, 35, 6184 (1997) maybe used.

Colonies grown after culturing are replicated on minimal agar media and minimal agar media each containing 0.05 to 0.5% methylerythritol. The mutant of interest, which requires methylerythritol to grow, is selected. That is, a strain capable of growing on minimal agar media containing methylerythritol but not on minimal agar media lacking methylerythritol is selected.

Strain ME 7 is an example of the resultant methylerythritol-requiring mutant obtained by the above manipulations.

② Cloning of the Gene Complementing Methylerythritol-requiring Nature

*Escherichia coli*, such as *E.coli* W3110 (ATCC14948), is inoculated into culture media, e.g., LB liquid medium, then cultured to the logarithmic growth phase by standard techniques.

Cells are collected from the resultant culture by centrifugation.

Chromosomal DNA is isolated and purified from the obtained cells according to standard techniques, such as those described in Molecular Cloning, Second Edition. The chromosomal DNA obtained by the method described in (1) above can be used as isolated and purified chromosomal DNA.

An appropriate amount of the chromosomal DNA is partially digested with an appropriate restriction enzyme, such as Sau 3 A I. The digested DNA fragments are fractionated by according to standard techniques, such as sucrose density-gradient centrifugation (26,000 rpm, 20° C., 20 hr).

The DNA fragments obtained by the above fractionation, 4 to 6 kb each, are ligated to a vector, e.g., pMW118 (Nippon Gene), which has been digested with an appropriate restriction enzyme to construct a chromosomal DNA library The methyleryhritol-requiring mutant isolated in ① above, such as the strain ME 7, is transformed using the ligated DNA according to standard techniques, e.g., those described in Molecular Cloning, Second Edition.

The resulting transformants are spread on minimal agar media supplemented with a drug corresponding to a drug-resistant gene carried by the vector, such as M9 agar medium containing 100 μg/l of ampicillin, then cultured overnight at 37° C.

Thus, transformants that have recovered their methylerythritol requirement can be selected by the method above.

Plasmids are extracted from the resultant transformants by standard techniques. Examples of a plasmid that can allow the transformants to recover their methylerythritol requirement are pMEW73 and pQEDXR.

The nucleotide sequence of the DNA integrated into the plasmid is sequenced.

An example of such a nucleotide sequence is a sequence containing a nucleotide sequence for yaeM gene of SEQ ID NO:10. Using the information on the nucleotide sequence for yaeM gene, homologues of yaeM gene can be obtained from other prokaryotes or plants in the same manner as described above.

II Production of Proteins Having Activity to Improve Efficiency in the Biosynthesis of Isoprenoid Compounds.

To express the resulting DNA in a host cell, the DNA fragment of interest is digested with restriction enzymes or deoxyribonucleases into one with a proper length containing the gene. Next the fragment is inserted into a downstream of a promoter region in an expression vector. Then the expression vector is introduced into a host cell appropriate for the expression vector.

Any host cell that can express the gene of interest can be used. Examples of the host cell include bacteria belonging to the genera *Escherichia, Serratia, Corynebacteriun, Brevibacterium, Pseudomonas, Bacillus, Microbacterium* and the like, yeasts belonging to the genera *Kluyveromyces, Saccharomyces, Schizosaccharomyces, Trichosporon, Schwanniomyces*, and the like, annual cells, and insect cells.

Expression vectors used herein can autonomously replicate in the host cell above or be integrated into a chromosomal DNA, and contain a promoter at the position to which the DNA of interest as described above can be transcribed.

When a bacterium is used as a host cell, a preferable expression vector for expression of the DNA above can autonomously replicate in the bacterium and is a recombinant vector comprising a promoter, ribosome binding sequence, the DNA above and a transcription termination sequence. The expression vector may contain a gene to regulate a promoter.

Examples of the expression vector include pBTrp2, pBTac1, pBTac2 (all of them are available from Boehringer Manheim K.K), pKK233-2 (Pharmacia), pSE280 (Invitrogen), pGEMEX-1 (Promega), pQE-8 (Qiagen. Inc), pQE-30 (Qiagen. Inc), pKYP10 (Japanese Patent Laid Open Publication No. 58-110600), pKYP200 (Agricultural Biological Chemistry, 48, 669, 1984), pLSA1 (Agric. Biol. Chem., 53, 277, 1989), pGEL1 (Proc. Natl. Acad. Sci. USA, 82, 4306, 1985), pBluescriptII SK+, pBluescriptII SK (−) (Stratagene), pTrS30 (FERM BP-5407), pTrS32 (FERM BP-5408), pGEX (Pharmacia), pET-3 (Novagen), pTerm2 (U.S. Pat. No. 4,686,191, U.S. Pat. No. 4,939,094, U.S. Pat. No. 5,160,735), psupex, pUB110, pTP5, pC194, pUC18 (gene, 33, 103, 1985), pUC19 (Gene, 33, 103, 1985), pSTV28 (TAKARA SHUZO CO., LTD.), pSTV29 (TAKARA SHUZO CO., LTD.), pUC118 (TAKARA SHUZO CO., LTD.), pPA1 (Japanese Patent Laid Open Publication No. 63-233798), pEG400 (J. Bacteriol., 172, 2392, 1990), and pQE-30 (Qiagen. Inc).

Any promoter that can function in a host cell may be used. Examples of such a promoter include promoters derived from *Eschenchia coli* or phages, such as trp promoter (P trp), lac promoter (P lac), $P_L$ promoter, $P_R$ promoter, $P_{SE}$ promoter, SP01 promoter, SP02 promoter, and penP promoter. Furthermore, P trp×2 promoter that is formed by joining two P trp in series, and tac promoter, letI promoter, and lacT7 promoter, those artificially designed and modified, can be used.

Any ribosome binding sequence that can function in a host cell can be used. A preferable plasmid has a distance between Shine-Dalgarno sequence and a starting codon appropriately adjusted, of for example 6 to 18 bases long.

A transcription termination sequence is not always required for expression of the DNA of interest. Preferably, a transcription termination sequence is arranged immediately followed by a structural gene.

Examples of the host cell used herein include microorganisms belonging to the genera *Escherichia, Corynebacteriun, Brevibacterium, Bacillus, Microbacterium, Serratia, Pseudomnas, Agrobacterium, Alicyclobacillus, Anabaena, Anacystis, Arthrobacter, Azobacter, Chromatium, Erwinia, Methylobacterium, Phormidium, Rhodobacter, Rhodopseudomonas, Rhodospirillum, Scenedesmun, Streptomyces, Synnecoccus,* and *Zymomonas.* Preferable host cells include microorganisms belonging to the genera *Escherichia, Corynebacterium, Brevibacterium, Bacillus, Pseudomonas, Agrobacterium, Alicyclobacillus, Anabaena, Anacystis, Arthrobacter, Azobacter, Chromatium, Erwinia, Methylobacterium, Phormidium, Rhodobacter, Rhodopseudomonas, Rhodospirillum, Scenedesmun, Streptomyces, synnecoccus* and *Zymomonas.*

More specific examples of the host cell include *Escherichia coli* XL1-Blue, *Escherichia coli* XL2-Blue, *Escherichia coli* DH1, *Escherichia coli* DH5 α, *Escherichia coli* MC1000, *Escherichia coli* KY3276, *Escherichia coli* W1485, *Escherichia coli* JM109, *Escherichia coli* HB101, *Escherichia coli* No. 49, *Escherichia coli* W3110, *Escherichia coli* NY49, *Escherichia coli* MP347, *Escherichia coli* NM522, *Bacillus subtilis, Bacihus amyloliquefacines, Brevibacterium ammoniagenes, Brevibacterium immariophilum* ATCC14068, *Brevibacterium saccharolyticum* ATCC14066, *Brevibacterium flavum* ATCC14067, *Brevibacterium lactofermentum* ATCC13869, *Corynebacterium glutamicum* ATCC13032, *Corynebacterium glutamicum* ATCC14297, Corynebacterium acetoacidophilum ATCC13870, *Microbacterium ammoniaphilum* ATCC15354, *Serratia ficaria*, *Serratia fonticola*, *Serratia liquefaciens*, *Serratia marcescens*, *Pseudomnas* sp. D-0110, *Agrobacterium radiobacter*, *Agrobacterium rhizogenes*, *Agrobacterium rubi*, *Anabaena cylindrica*, *Anabaena doliolum*, *Anbaena flos-aquae*, *Arthrobacter aurescens*, *Arthrobacter citreus*, *Arthrobacter globformis*, *Arthrobacter hydrocarboglutamicus*, *Arthrobacter mysorens*, *Arthrobacter nicotianae*, *Arthrobacter paraffineus*, *Arthrobacter protophomiae*, *Arthrobacter roseoparaffinus*, *Arthrobacter sulfureus*, *Arthrobacter ureafaciens*, *Chromatium buderi*, *Chromatium tepidum Chromauium vinosum*, *Chromatium warningii*, *Chromatium fluviatile*, *Erwinia uredovora*, *Erwinia carotovora*, *Erwnia ananas*, *Erwinia herbicola*, *Erwinia punctata*, *Erwinia tereus*, *Mehylobacterium rhodesianum*, *Methylobacterium extorquens*, *Phomidium* sp. ATCC29409, *Rhodobacter capsulatus*, *Rhodobacter sphaeroides*, *Rhodopseudomonas blastica*, *Rhodopseudomonas marina*, *Rhodopseudomonas palustris*, *Rhodospirillum rubrum*, *Rhodospirillum salexigens*, *Rhodospirillum salinarum Streptomyces ambofaciens*, *Streptomyces aureofaciens*, *Streptomyces aureus*, *Streptomyces fungicidicus*, *Streptomyces griseochromogenes*, *Streptomyces griseus*, *Streptomyces lividans*, *Streptomyces olivogriseus*, *Streptomyces rameus*, *Streptomyces tanashiensis*, *Streptomyces vinaceus*, and *Zymomonas mobilis*.

Any method to introduce a recombinant vector into the host cell as described above may be used. Examples of such a method include a method using calcium ions (Proc. Natl. Acad. Sci. USA, 69, 2110, 1972), protoplast method (Japanese Patent Laid Open Publication No. 63-2483942), or methods described in Gene, 17, 107 (1982) or Molecular & General Genetics, 168, 111 (1979).

When yeast is used as a host cell, expression vectors are, for example, YEp13 (ATCC37115), YEp24 (ATCC37051), YCp50(ATCC37419), pHS19, and pHS15.

Any promoter that can function in yeast can be used. Examples of such a promoter include PH05 promoter, PGK promoter, GAP promoter, ADH promoter, gal 1 promoter, gal 10 promoter, heat shock protein promoter, MF α1 promoter, and CUP1 promoter.

Host cells used herein include *Saccharomyces cerevisae*, *Schizosaccharomyces pombe*, *Kluyveromyces lactis*, *Trichosporon pullulans*, and *Schwanniomyces alluvius*.

Any method to introduce a recombinant vector, that is, to introduce DNA into yeast may be used. Examples of such methods include Electroporation (Methods. Enzymol., 194, 182, 1990), Spheroplast method (Proc. Natl. Acad. Sci. USA, 75, 1929 (1978)), lithium acetate method (J. Bacteriol., 153, 163 (1983)), and methods described in Proc. Natl. Acad. Sci. USA, 75, 1929 (1978).

When an animal cell is used as a host cell, expression vectors are, for example, pcDNAI, pcDM8 (Funakoshi Co., Ltd), pAGE107 [Japanese Patent Laid Open Publication No. 3-22979; Cytotechnology, 3, 133 (1990)], pAS3-3 [Japanese Patent Laid Open Publication No. 2-227075, pCDM8 (Nature, 329, 840 (1987)), pcDNAI/Amp (Invitrogen), pREP4 (Invitrogen), pAGE103 [J. Biochem., 101, 1307 (1987)], and pAGE210.

Any promoter that can function in an animal cell may be used. Examples of such promoters include a promoter for IE (immediate early) gene of cytomegalovirus (human CMV), SV40 initial promoter, retrovirus promoter, metallothionein promoter, heat shock promoter, and SR α promoter. Moreover, an enhancer of human CMV IE gene may be used together with a promoter.

Host cells used herein are, for example, Namalwa cells, HBT5637 (Japanese Patent Laid Open Publication No. 63-299), COS1 cells, COS7 cells, and CHO cells.

Any method to introduce a recombinant vector into an animal cell, that is, to introduce DNA into an animal cell may be used. Examples of such methods include Electroporation [Cytotechnology, 3, 133 (1990)], calcium phosphate method (Japanese Patent Laid Open Publication No. 2-227075), lipofection [Prc. Natl. Acad. Sci., USA, 84, 7413 (1987)], and methods described in Virology, 52, 456 (1973). Recovery and culture of the transformant can be carried out according to methods described in Japanese Patent Laid Open Publication No. 2-227075 and Japanese Patent Lid Open Publication No. 2-257891.

When an insect cell is used as a host cell, proteins can be expressed according to methods described in, such as Baculovirus Expression Vectors, A Laboratory Manual, Current Protocols in Molecular Biology Supplement 1–38 (1987–1997), and Bio/Technology, 6, 47 (1988).

That is, a vector for introducing a recombinant gene and Baculovirus are co-transduced into an insect cell to obtain a recombinant virus in the culture supernatant of the insect cell. Then an insect cell is infected with the recombinant virus, resulting in expression of the protein of interest.

Examples of the vectors to transfer genes include pVL1392, pVL1393, pBlueBacIII (all of which are manufactured by Invitrogen).

Baculoviruses used herein are, for example, *Autographa californica* nuclear polyhedrosis virus that infects Barathra insects.

Examples of the insect cells include ovarian cells of *Spodoptera frugiperda*, Sf9, and Sf21 (Baculovirus Expression Vectors, A Laboratory Manual (W. H. Freeman and Company, New York, 1992), and of *Trichoplusia ni*, High 5 (Invitrogen).

Methods of cotransduction of the vector for transferring the recombinant gene and the Baculovirus into an insect cell to prepare a recombinant virus include calcium phosphate transfection (Japanese Patent Laid Open Publication No. 2-227075) and, lipofection [Proc. Natl. Acad. Sci. USA, A8, 7413 (1987)].

Methods for expressing genes include secretory production, and fusion protein expression according to the techniques shown in Molecular Coning, Second Edition, in addition to direct expression.

When the gene is expressed in yeasts, animal cells, or insect cells, a protein to which sugar or a sugar chain is added, can be obtained.

Proteins having activity to improve efficiency in the biosynthesis of isoprenoid compounds can be produced by culturing a transformant containing a recombinant DNA to which the above DNA has been introduced in a medium, allowing the transformant to produce and accumulate proteins having activity to improve efficiency in the biosynthesis of isoprenoid compounds in the culture, then collecting the proteins from the culture.

The transformants for producing proteins with activity to improve efficiency in the biosynthesis of isoprenoid compounds of the present invention, can be cultured by standard techniques to culture a host cell.

When the transformant of this invention is prokaryote such as *Escherichia coli* or eukaryote such as yeast, a medium for culturing such transformants contains a carbon source, a nitrogen source, and inorganic salts, which the microorganisms can assimilate, and allows the transformant to grow efficiently. Either natural media or synthetic media can be used if they satisfy the above conditions.

Any carbon source assimilable by the microorganisms may be used. Such carbon sources include glucose, fructose, sucrose, and molasses containing them, carbohydrates e.g., starch or hydrolysates of starch, organic acids e.g., acetic acid and propionic acid, and alcohols e.g., ethanol and propanol.

Examples of nitrogen sources include ammonia, salts of inorganic acids or organic acids, e.g., ammonium chloride, ammonium sulfate, ammonium acetate, and ammonium phosphate, other nitrogen-containing compounds, peptone, meat extract, yeast extract, corn steep liquor, casein hydrolysates, soybean meal and soybean meal hydrolysate, various fermentation microorganic cells or their digests.

Examples of inorganic salts include potassium primary phosphate, potassium secondary phosphate, magnesium phosphate, magnesium sulfate, sodium chloride, ferrous sulfate, manganese sulfate, copper sulfate, and calcium carbonate.

Culturing is carried out by shaking culture or submerged aeration-agitation culture are carried out under aerobic conditions. The preferable culture temperature ranges from 15 to 40° C. The preferable culture period ranges from 16 hours to 7 days. The pH is kept within a range from 3.0 to 9.0 while culturing. The pH is adjusted using inorganic or organic acid, alkaline solutions, urea, calcium carbonate, ammonia or the like.

If necessary, an antibiotics e.g., ampicillin or tetracycline may be added to the media while culturing.

When microorganisms transformed with the expression vectors using inducible promoters are cultured, inducers may be added to the media if necessary For example, isopropyl-β-D-thiogalactopyranoside (IPTG) or the like may be added to the media when microorganisms transformed with the expression vectors containing lac promoter are cultured; indoleacrylic acid (IAA) or the like may be added when microorganisms transformed with the expression vectors containing trp promoter are cultured.

The media for culturing a transformant obtained by using an animal cell as a host cell include a generally used RPMI1640 medium [The Journal of the American Medical Association, 119, 519 (1967)], Eagle's MEM medium [Science, 122, 501 (1952)], DMEM medium [Virology, 8, 396 (1959)], 199 medium [Proceeding of the Society for the Biological Medicine, 73, 1 (1950)] or those to which fetal calf serum or the like is added.

Normally, the transformant is cultured in the presence of 5% $CO_2$ for 1 to 7 days at pH 6 to 8 and 30 to 40° C.

If necessary, antibiotics e.g., kanamycin and penicillin may be added to the medium while culturing.

Examples of media to culture a transformant obtained by using an insect cell as a host cell include a generally used TNM-FH medium (Pharmingen), Sf-900 II SFM medium (GIBCO BRL), ExCell400, ExCell405 (both manufactured by JRH Biosciences), Grace's Insect Medium (Grace, T.C.C., Nature, 195, 788 (1962)).

The transformant is generally cultured for 1 to 5 days atpH 6 to 7 and at 25° C. to 30° C.

If necessary antibiotics e.g., gentamycin may be added to the medium while culturing.

Proteins having activity to improve efficiency in the biosynthesis of isoprenoid compounds of this invention can be isolated and purified from the culture of the transformant of this invention by standard isolation and purification techniques for a enzyme.

For example, when the protein of this invention is expressed in a soluble form within the cell, after the culture is completed the cells are recovered by centrifugation, suspended in aqueous buffer, then disrupted using an ultrasonicator, french press, Manton Gaulin homogenizer, Dyno-Mill, or the like, thereby obtaining cell-free extracts. The cell-free extract is separated by centrifugation to obtain the supernatant The purified sample can be obtained from the supernatant by one of or a combination of standard techniques for isolating and purifying enzymes. Such techniques include a solvent extracting technique, salting out technique using ammonium sulfate, desalting technique, precipitation technique using organic solvents, anion exchange chromatography using resins such as diethylaminoethyl (DEAE)-Sepharose, and DIAION HPA-75 (Mitsubishi Chemical Corp.), cation exchange chromatography using resins e.g., S-Sepharose FF (Pharmacia), hydrophobic chromatography using resins e.g., butylsepharose, phenylsepharose, gel filtration using molecular sieve, affinity chromatography, chromatofocusing, and electrophoresis such as isoelectric focusing.

When the proteins that form inclusion bodies are expressed in the cells, the cells are recovered, disrupted, and separated by centrifugation, thereby obtaining precipitated fractions. From the resulting precipitated fractions, the protein is recovered by standard techniques, and then the insoluble protein is solubilized using a protein denaturing agent. The solubilized solution is diluted or dialyzed to an extent that the solution contains no protein denaturing agent or that the concentration of protein denaturing agent does not denature protein, thereby allowing the protein to form a normal three-dimensional structure. Then the purified sample can be obtained by the same techniques for isolation and purification as described above.

When the protein of this invention or its derivative, such as a sugar-modified protein, is secreted outside the cell, the protein or its derivative, such as a sugar chain adduct, can be recovered from the culture supernatant. That is, the culture is treated by centrifugation and the like as described above so as to obtain soluble fractions. From the soluble fractions, the purified sample can be obtained using the techniques for isolation and purification as described above.

The resulting protein as described above is, for example a protein having an amino acid sequence selected from amino acid sequences of SEQ ID NOS: 1 to 5.

Moreover, the protein expressed by the method above can be chemically synthesized by techniques including Fmoc method (fluorenylmethyloxycarbonyl method), tboc method (t-butyloxycarbonyl method). Further, the protein can be synthesized by using a peptide synthesizer of Souwa Boeki K.K. (Advanced ChemTech, U.S.A.), Perkin-Elmer Japan (Perkin-Elmer, U.S.A), Pharmacia BioTech (Pharmacia BioTech, Sweden), ALOKA CO., LTD. (Protein Technology Instrument), KURABO INDUSTRIES LTD. (Synthecell-Vega, U.S.A), PerSeptive Limited., Japan (PerSeptive, U.S.A), or SHIMADZU CORP.

III. Production of Isoprenoid Compound

Isoprenoid compounds can be produced by culturing the tansformants obtained as described in II above according to the method of II above, allowing the transformants to produce and accumulate isoprenoid compounds in the culture, then recovering the isoprenoid compounds from the culture.

The above culture can yield isoprenoid compounds, such as ubiquinone, vitamin $K_2$, and carotenoids. Specific examples of isoprenoid compounds include ubiquinone-8 and menaquinone-8 produced using microorganisms belonging to the genus *Eschenchia* as a transformant, ubiquinone-10 produced using those belonging to the genus

*Rhodobacter*, vitamin K$_2$ produced using those belonging to the genus *Arthrobacter* as a transformant, astaxanthin produced using those belonging to the genus *Agrobacterium* as a transformant, and lycopene, β-carotene, and zeaxanthin produced using those belonging to the genus *Erwinia* as a transformant After the culture is completed, in order to isolate and purify isoprenoid compounds, isoprenoid compounds are extracted by adding an appropriate solvent to the culture, the precipitate is removed by e.g., centrifugation, and then the product is subjected to various chromatography.

IV. Screening a Substance Inhibiting Enzymatic Activity on Non-Mevalonate Pathway (1) Deflation of Enzymatic Activity on Non-Mevalonate Pathway The enzymatic activity on non-mevalonate pathway can be determined according to normal methods for determining enzymatic activity.

The pH of the buffer used as a reaction solution to determine activity should be within a range that does not inhibit the enzymatic activity of interest A preferable pH range includes the optimal pH.

For example, a buffer at pH 5 to 10, preferably 6 to 9 is used for 1-deoxy-D-xylulose 5-phosphate reductoisomerase.

Any buffer can be used herein so far as it does not inhibit the enzymatic activity and can be adjusted to the pH above. Examples of such a buffer include Tris-hydrochloric acid buffer, phosphate buffer, borate buffer, HEPES buffer, MOPS buffer, and bicarbonate buffer. For example, Tris-hydrochloric acid buffer can preferably be used for 1-deoxy-D-xylulose 5-phosphate reductoisomerase.

A buffer of any concentration may be employed so far as it does not inhibit the enzymatic activity The preferable concentration ranges from 1 mol/l to 1 mol/l.

When the enzyme of interest requires a coenzyme, a coenzyme is added to the reaction solution. For example, NADPH, NADH or other electron donors can be used as a coenzyme for 1-deoxy-D-xylulose 5-phosphate reductoisomerase. A preferable coenzyme is NADPH.

Any concentration of the coenzyme to be added can be employed so far as it does not inhibit reaction. Such a concentration preferably ranges from 0.01 mol/l to 100 mol/l, more preferably, 0.1 mol/l to 10 mol/l.

Metal ions may be added to a reaction solution if necessary. Any metal ion can be added so far as it does not inhibit reaction. Preferable metal ions include Co$^{2+}$, Me$^{2+}$, and Mn$^{2+}$.

Metal ions may be added as metallic salts. For example, a chloride, a sulfate, a carbonate, and a phosphate can be added.

Any concentration of the metal ion to be added can be employed so far as it does not inhibit reaction. A preferable concentration ranges from 0 mol/l to 100 mol/l, more preferably, 0.1 mol/l to 10 mol/l.

The substrate of the enzyme of interest is added to the reaction solution. For example, 1-deoxy-D-xylulose 5-phosphate is added for 1-deoxy-D-xylulose 5-phosphate reductoisomerase.

Any concentration of the substrate may be employed so far as it does not inhibit reaction. The preferable concentration ranges from 0.01 mol/l to 0.2 mol/l in the reaction solution.

The enzyme concentration used in reaction is not specifically limited. Normally, the concentration ranges from 0.01 mg/ml to 100 mg/ml.

An enzyme used herein is not necessarily purified into a single substance. It may contain contaminative proteins. In the search as described in (2) below, cellular extracts containing 1-deoxy-D-xylulose 5-phosphate reductoisomerase activity or cells having the same activity can be used.

Any reaction temperature may be employed so far as it does not inhibit enzymatic activity A preferable temperature range includes the optimal temperature. That is, the reaction temperature ranges from 10° C. to 60° C., more preferably, 30° C. to 40° C.

Activity can be detected by a method for measuring a decrease in substrates accompanying the reaction or an increase in reaction products as the reaction proceeds.

Such a method is a method wherein the substance of interest is separated and quantitatively determined by e.g, high performance liquid chromatography (HPLC) if necessary. When NADH or NADPH increases or decreases as the reaction proceeds, activity can directly be determined by measuring the absorbance at 340 nm of the reaction solution. For example, the activity of 1-deoxy-D-xylulose 5-phosphate reductoisomerase can be detected by measuring a decrease in the absorbance at 340 nm using a spectrophotometer to determine NADPH quantity that decreases as the reaction proceeds.

(2) Screening a Substance Inhibiting Enzymatic Activity on the Non-Mevalonate Pathway A substance inhibiting enzymatic activity on the non-mevalonate pathway can be screened for by adding the substance to be screened for to the enzymatic activity measurement system as described in (1) above, allowing the mixture to react similarly, and then screening a substance that suppresses the amount of the substrates decreased in comparison to a case when no such substance is added; or a substance that suppresses the yield of the reaction product Screening methods include a method wherein the decrease in the amount of substrates or the increase in the amount of reaction products is traced with time; or a method where after the reaction has proceeded for a certain period the decrease in the amount of substrates or the increase in the amount of reaction products is measured.

In the method wherein the decrease in the amount of substrates or the increase in the amount of reaction products is traced with time, the amount is measured preferably at 15 seconds to 20 minutes intervals, more preferably at 1 to 3 minutes intervals during reaction.

To measure the decrease in the amount of substrates or the increase in the amount of reaction products after reaction has proceeded for a certain period, the reaction period is preferably 10 minutes to 1 day, more preferably, 30 minutes to 2 hours.

A substance inhibiting the enzymatic activity on the non-mevalonate pathway inhibits the growth of microorganisms and plants that possess the non-mevalonate pathway. The inventors have first found the fact that this substance inhibits the growth of the microorganisms and plants.

The non-mevalonate pathway is present in microorganisms and plants, but absent in animals and humans. Therefore, the substance inhibiting the enzymatic activity on the non-mevalonate pathway but not affecting human and animals can be obtained by the above described screening method.

This substance can be an effective antibiotic or herbicide.

This specification includes part or all of the contents as disclosed in the specification and/or drawings of Japanese Patent Application Nos. 10-103101, 10-221910 and 11-035739, which are priority documents of the present application.

BEST MODE FOR CARRYING OUT THE INVENTION

Figure 1:
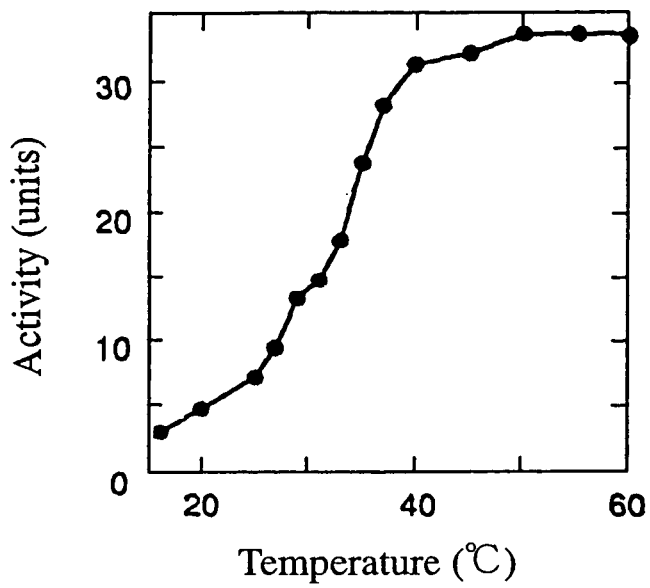
FIG. 1 shows the effect of reaction temperature on 1-deoxy-D-xylulose 5-phosphate reductoisomerase activity.

The invention will now be described by way of examples, but shall not be limited thereto. Unless otherwise specified, gene recombination shown in the examples was carried out according to techniques described in Molecular Cloning, Second Edition (hereinafter referred to as the standard techniques).

EXAMPLE 1

Cloning of DNA Encoding Proteins Involved in the Biosynthesis of Isoprenoid Compounds (1) Cloning of DNA encoding proteins involved in the biosynthesis of isoprenoid compounds using the nucleotide sequence of E.coli DXS gene One platinum loop of E.coli XL1-Blue (purchased from TOYOBO) was inoculated into 10 ml of LB liquid medium, then cultured overnight at 37° C.

After culturing, cells were collected by centrifugation from the resultant culture.

Chromosomal DNA was isolated and purified from the cells according to the standard techniques.

Sense and antisense primers, each having BamH I and EcoR I restriction enzyme sites at their 5'-ends and consisting of nucleotide sequence pairs of SEQ ID NOS:12 and 13, 14 and 15, 12 and 16, 17 and 18, and 19 and 13; and sense and antisense primers, each having BamH I restriction enzyme site at their 5'-ends and consisting of a nucleotide sequence pair of SEQ ID NO:22 and 23; were synthesized using a DNA synthesizer.

PCR was carried out with a DNA Thermal Cycler (Perkin Elmer Instruments, Inc. Japan) using these primers, chromosomal DNA as a template, and a TaKaRa La-PCR™ Kit Ver. 2 (TAKARA SHUZO CO., LTD.), Expand™ High-Fidelity PCR System (Boehringer Manheim K.K.) or a Taq DNA polymerase (Boehringer).

PCR was carried out for 30 cycles. In the case of amplifying a DNA fragment of 2 kb or less, one cycle consisting of reaction at 94° C. for 30 seconds, 55° C. for 30 seconds to 1 minute, and 72° C. for 2 minutes; in the case of amplifying a DNA fragment of more than 2 kb, one cycle consisting of reaction at 98° C. for 20 seconds, and 68° C. for 3 minutes; then followed by the reaction at 72° C., for 7 minutes.

Among the DNA fragments amplified by PCR, DNA fragments amplified using sense and antisense primers, each having BamH I and EcoR I; restriction enzyme sites at their 5'-ends, were digested with restriction enzymes BamH I and EcoR I; DNA fragments amplified using sense and antisense primers, each having BamH I restriction enzyme site at their 5'-ends, were digested with restriction enzyme BamH I.

After the digestion, these DNA fragments treated with the restriction enzymes were subjected to agarose gel electrophoresis and recovered BamH I and EcoR I-treated DNA fragments and BamH I-treated DNA fragments.

A broad host range vector pEG 400 containing lac promoter [J. Bac., 172, 2392 (1990)] was digested with restriction enzymes BamH I and EcoR I, subjected to agarose gel electrophoresis and recovered BamH I and EcoR I-treated pEG 400 fragments.

pUC118 (TAKARA SHUZO CO., LTD.) was digested with a restriction enzyme BamH I, then subjected to agarose gel electrophoresis and recovered BamH I-treated pUC 118 fragments.

Each of the resultant BamH I and EcoR I-treated DNA fragments was mixed with BamH I and EcoR I-treated pEG 400 fragments, then the mixture was allowed to precipitate with ethanol. The obtained DNA precipitate was dissolved in 5 µl of distilled water for ligation reaction to occur, thereby obtaining each recombinant DNA.

Using the resultant recombinant DNA, E.coli (purchased from TOYOBO) DH5 α was transformed according to the standard techniques. Then the transformant was spread on LB agar medium containing 100 µg/ml of spectinomycin, then cultured overnight at 37° C.

Some colonies of the transformant resistant to spectinomycin were cultured in 10 ml of LB liquid medium containing 100 µg/ml of spectinomycin with shaking for 16 hours at 37° C.

The resulting culture was centrifuged, so that cells were collected.

Plasmids were isolated from the cells according to the standard tehniques.

To confirm that the isolated plasmids contained the DNA fragment of interest, the plasmids were cleaved with various restriction enzymes to examine their structures and their nucleotide sequences were sequenced.

A plasmid containing a DNA with a nucleotide sequence of SEQ ID NO:6, DNA with a nucleotide sequence of SEQ ID NO:7, DNA with a nucleotide sequence of SEQ ID NO: 8, and DNA with a nucleotide sequence of SEQ ID NO: 9 was named pADO-1. A plasmid containing a DNA with a nucleotide sequence of SEQ ID NO: 6 was named pDXS-1. A plasmid containing a DNA with a nucleotide sequence of SEQ ID NO: 7 was named pISP-1. A plasmid containing a DNA with a nucleotide sequence of SEQ ID NO: 9 was named pTFE-1.

The above BamH I-treated DNA fragments and BamH I-treated pUC118 fragments were mixed, then the mixture was allowed to precipitate with ethanol. The resulting DNA precipitate was dissolved in 5 µl of distilled water for ligation reaction to occur to obtain recombinant DNA. Escherichia coli was transformed using the recombinant DNA in the same manner as described above, then plasmids were isolated from the transformants.

To confirm the isolated plasmids contain the DNA fragments of interest, the plasmids were cleaved with various restriction enzymes to examine their structure and their nucleotide sequences were sequenced in the same manner as described above.

These plasmids were digested with BamH I. The DNA fragments of interest were recovered in the same manner as described above, then sub-cloned into an expression vector pQE30 (Qiagen. Inc).

The plasmid obtained by the sub-cloning above and having a nucleotide sequence of SEQ ID NO:6 was named pQEDXS-1.

(2) Cloning of the Gene Complementing Methylerythritol-requiring Nature

① Selection of Methylerythritol-requiring Mutant of *Escherichia coli*

*E.coli* W3110 (ATCC14948) was inoculated into LB liquid medium and cultured to its logarithmic growth phase.

After culturing, cells were recovered from the resulting culture by centrifugation.

The cells were washed with 0.05 mol/l Tris-maleate buffer (pH 6.0), then suspended in the same buffer to the cell density of $10^9$ cells/ml.

Mutation was induced by adding NTG to the suspension to a final concentration of 600 mg/l, and then the mixture was maintained for 20 minutes at room temperature.

These NTG treated cells were spread on M9 minimal agar medium containing 0.1% methylerythritol (Molecular Cloning, Second Edition) plate and cultured.

Methylerythritol was chemically synthesized according to the method described in Tetrahedron Letters, 38, 35, 6184 (1997).

Colonies grown on M9 minimal agar medium containing 0.1% methylerythritol were replicated on M9 minimal agar medium and on M minimal agar medium containing 0.1% methylerythritol. The mutant of interest, a strain requiring methylerythritol to grow, was selected. That is, a strain capable of growing on a minimal agar medium containing 0.1% methylerythritol but not on the same lacking methylerythritol was selected.

The thus obtained methylerythritol-requiring mutant ME7 was used in the following experiments.

② Cloning of the Gene Complementing Methylerythitol-requiring Nature

*Escherichia coli* W3110 (ATCC14948) was inoculated into LB liquid medium, then cultured to its logarithmic growth phase. Then cells were collected from the resultant culture by centrifugation.

Chromosomal DNA was isolated and purified from the obtained cells according to the standard techniques.

200 μg of the chromosomal DNA was partially digested with a restriction enzyme, Sau 3AI. The resulting DNA fragments were fractionated by sucrose density-gradient centrifugation (26,000 rpm, 20° C., 20 hr).

The DNA fragments obtained by the above fractionation, 4 to 6 kb each, were ligated to pMW118 vector (Nippon Gene), which had been digested with a restriction enzyme BamH I, constructing a genomic DNA library.

Using this genomic DNA library, the strain M isolated in ① above was transformed according to the standard techniques.

The resulting transformants were spread on LB agar medium supplemented with 100 μg/l of ampicillin, then cultured overnight at 37° C.

Plasmids were extracted from each colony that grew on the agar medium and then the nucleotide sequences were determined.

The plasmids determined its nucleotides sequence had contained the nucleotide sequence of SEQ ID NO: 10. These plasmids were named pMEW41 and pMEW 73.

A plasmid extracted from one strain of the clones having the sequence was named pMEW73.

The pMEW 73 was double-digested with Hind III and Sac I. The resultant Hind III and Sac I-treated DNA fragment having a nucleotide sequence of SEQ ID NO:10 was ligated to multi-cloning sites of broad host range vector pEG400 [J. Bac., 172, 2392 (1990)], constructing pEGYM1.

The Hind III—Sac I-treated DNA fragment was ligated to the Hind III—Sac I site of vector pUC19 (Gene, 33, 103 (1985)), constructing pUCYM-1.

According to the information on the nucleotide sequence of chromosomal DNA of *Escherichia coli* based on Genbank data base, the DNA fragment that had been inserted into the vector was confirmed to contain yaeM gene.

A recombinant vector, which can express yaeM gene sufficiently, was constructed by following method with PCR [Science, 230, 1350 (1985)].

A sense primer having a sequence of SEQ ID NO:20 and an antisense primer having a sequence of SEQ ID NO:21 were synthesized using a DNA synthesizer.

A Bam H I restriction enzyme recognition site was added to each 5'-end of the sense and antisense primers. yaeM gene was amplified by PCR with DNA Thermal Cycler (Perkin Elmer Instruments, Inc. Japan) using chromosomal DNA of *E.coli* as a template, these primers and Taq DNA polymerase (Boelinnger).

PCR was carried out by 30 cycles, one cycle consisting of reaction at 94° C. for 30 seconds, reaction at 55° C. for 30 seconds, and reaction at 72° C. for 2 minutes followed by reaction at 72° C. for 7 minutes.

After the amplified DNA fragments and pUC118 (TAKARA SHUZO CO., LTD.) were digested with a restriction enzyme BamH I, each of the DNA fragments were purified by agarose gel electrophoresis.

Both of these fragments were mixed, then the mixture was allowed to precipitate with ethanol. The resultant DNA precipitate was dissolved in 5 μl of distilled water for ligation reaction to occur, thereby obtaining recombinant DNA.

The recombinant DNA was confirmed to be yaeM gene by determining the nucleotide sequences, then sub-cloned to expression vector pQE30 (Qiagen, Inc).

The resulting recombinant DNA was named pQEYM 1.

The strain ME7 was transformed using pQEYM1 by standard techniques. The transformant was spread on LB agar medium containing 100 μg/ml of ampicillin, then cultured overnight at 37° C.

The transformants were confirmed to form colonies at the same growth rate as wild-type strain, suggesting that yaeM gene complemented mutation in the strain ME7.

EXAMPLE 2

Production of Ubiquinone-8 (CoQ8) Using Recombinant *Escherichia coli*

(1) *E.coli* DH5α were transformed using the plasmids pAD0-1, pDXS-1, and pXSE-1, those obtained in Example 1 above, and pEG400 as a control, respectively, then *E.coli* DH5 α/pAD0-1, *E.coli* DH5 α/pDXS-1, *E.coli* DH5 α/pXSE-1 and *E.coli* DH5 α/pEG400 that showed resistance to spectinomycin at a concentration of 100 μg/ml were obtained These transformants were inoculated into a test tube containing 10 ml of LB medium supplemented with thiamine and vitamin $B_6$, 100 mg/l each, 50 mg/l of p-hydroxybenzoic acid, and 100 μg/ml of spectinomycin. Then the transformants were cultured with shaking for 72 hours at 30° C.

After the culture was completed, each culture was concentrated 10-fold.

To each 300 μl of concentrated culture, 300 μl 2-butanol and 300 μl glass beads were added. Isoprenoid compounds were extracted with the solvent while disrupting the cells by Multi Beads Shocker MB-200 (YASUI KIKAI for 5 minutes. Then the 2-butanol layer was collected by centrifugation.

The amount of CoQ8 produced by the transformants was calculated by Quantitative analysis of the CoQ8 in the butanol layer using high performance liquid chromatography (LC-10A, SHIMADZU CORP.).

HPLC was carried out using Develosil ODS-HG-5 (NOMURA CHEMICAL K.K.) as a column, and methanol:n-hexane=8:2 solution as a mobile phase at 1 ml/min of the flow rate and 275 nm of the measuring wavelength.

Table 1 shows the results.

TABLE 1

CoQ8 Production by transformant of *Escherichia coli*

| Transformant | Cell Amount (OD660) | Amount of CoQ8 Produced (mg/L) | Intracellular Content[*1] |
|---|---|---|---|
| E. coli DH5 α/pEG400 | 5.8 | 0.63 | 1.1 |
| E. coli DH5 α/pADO-1 | 5.5 | 0.98 | 1.8 |
| E. coli DH5 α/pDXS-1 | 5.2 | 0.85 | 1.6 |
| E. coli DH5 α/pXSE-1 | 5.6 | 0.67 | 1.2 |

[*1]Intracellular content is shown with a value obtained by dividing a 10-fold CoQ8 production (mg/L) by a cell amount (OD660).

The amount of CoQ8 produced was significantly higher in DH5 α/pADO-1, DH5 α/pDXS-1 and DH5 α/pXSE-1 than in the control strain DH5 α/pEG400. In particular, the highest productivity was shown by DH5 α/pADO-1 to which all DNA obtained in Example 1 were introduced.

(2) *E.coli* DH5 α/pDXS-1 or *E.coli* DH5 α/pEG400, as obtained in (1) above, was inoculated into a test tube containing 10 ml of a M9 medium, and then cultured with shaking for 72 hours at 30° C.

After the culture was completed, the amount of CoQ8 produced by the transformants was calculated in the same manner as in (1) above.

Table 2 shows the results.

TABLE 2

CoQ8 Production by transformant of *Escherichia coli*

| Transformant | Cell amount (OD660) | Amount of CoQ8 Produced (mg/L) | Intracellular Content[*1] |
|---|---|---|---|
| E. coli DH5 α/pEG400 | 3.1 | 0.49 | 1.6 |
| E. coli DH5 α/pDXS-1 | 2.5 | 1.02 | 4.1 |

[*1]Intracellular content is shown with a value obtained by dividing a 10-fold CoQ8 production (mg/L) by a cell amount (OD660).

The amount of CoQ8 produced was significantly higher in DH5 α/pDXS-1 tan in the control strain DH5 α/pEG400.

(3) Production of CoQ8 using Recombinant *Escherichia coli*

The plasmid pEGYM1 obtained in Example 1 or pEG400 as a control was introduced into *E.coli* DH5 α and *E.coli* DH5 α/pEGYM1 and *E.coli* DH5 α/pEG400 that show resistance to spectinomycin at a concentration of 100 μg/ml were obtained.

These transformants were inoculated into a test tube containing 10 ml of LB medium supplemented with 1% glucose, 100 mg/l of vitamin $B_1$, 100 mg/l of vitamin $B_6$, 50 mg/l of p-hydroxybenzoic acid. Then the transformants were cultured with shaking for 72 hours at 30° C.

After the culture was completed, the amount of CoQ8 produced by the transformants was calculated in the same manner as in (1) above.

Table 3 shows the results.

TABLE 3

CoQ8 Production by transformants of *Escherichia coli*

| Transformant | Cell amount (OD660) | Amount of CoQ8 Produced (mg/L) | Intracellular Content[*1] |
|---|---|---|---|
| E. coli DH5 α/pEG400 | 14.44 | 0.83 | 0.57 |
| E. coli DH5 α/pEGYM1 | 13.12 | 0.94 | 0.71 |

[*1]Intracellular content is shown with a value obtained by dividing a 10-fold CoQ8 production (mg/L) by a cell amount (OD660).

The amount of CoQ8 produced was significantly higher in DH5 α/pEGYM1 than in the control strain DH5 α/pEG400.

EXAMPLE 3

Production of Menaquinone-8 (MK-8) by Recombinant *Escherichia coli*

(1) The *E.coli* DH5 α/pADO-1 or *E.coli* DH5 α/pEG400, obtained in Example 2 (1), was inoculated into a test tube containing 10 ml of TB medium supplemented with 100 μg/ml of spectinomycin, and then cultured with shaking for 72 hours at 30° C. The TB medium had been prepared by dissolving 12 g of bactotrypton (Difco), 24 g of yeast extract (Difco), and 5 g of glycerol into 900 ml of water followed by the addition of 100 ml of aqueous solution containing 0.17 mol/l $KH_2PO_4$ and 0.72 mol/l $K_2HP)_4$.

After the culture was completed, MK-8 was quantified in the same quantifying method for CoQ8 as in Example 2 (1), then the amount of MK-8 produced by the transformants was calculated.

Table 4 shows the results.

TABLE 4

MK-8 Production by transformants of *Escherichia coli*

| Transformant | Cell amount (OD660) | Amount of MK-8 Produced (mg/L) | Intracellular Content[*1] |
|---|---|---|---|
| E. coli DH5 α/pEG400 | 23.2 | 1.1 | 0.46 |
| E. coli DH5 α/pADO-1 | 23.5 | 1.8 | 0.75 |

[*1]Intracellular content is shown with a value obtained by dividing a 10-fold CoQ8 production amount (mg/L) by a cell amount (OD660).

The amount of MK-8 produced was significantly higher in DH5 α/pADO-1 than in the control DH5 α/pEG400.

(2) E.coli DH5 α/pDXS-1 or E.coli DH5 α/pEG400, obtained in Example 2 (1), was cultured in the same maimer in (1) above, then the amount of MK-8 produced by the transformants was calculated.

Table 5 shows the results.

TABLE 5

Production of MK-8 by transformants of *Escherichia coli*

| Transformant | Cell amount (OD660) | Amount of MK-8 Produced (mg/L) | Intracellular Content[*1] |
|---|---|---|---|
| E. coli DH5 α/pEG400 | 42.8 | 2.41 | 0.56 |
| E. coli DH5 α/pDXS-1 | 44.0 | 2.96 | 0.67 |

[*1]Intracellular content is shown with a value obtained by dividing a 10-fold CoQ8 production (mg/L) by a cell amount (OD660).

The amount of MK-8 produced was significantly higher in DH5 α/pDXS-1 than in the control strain DH5 α/pEG400.

EXAMPLE 4

Production of CoQ8 by Recombinant *Erwing carotovora*

A plasmid pDXS-1 obtained in Example 1 or pEG400 as a control, was introduced into *Erwinia carotovora* IFO-3380, thereby obtaining transformants IFO-3380/pDXS-1 and IFO-3380/pEG400, both of which were resistant to spectinomycin at a concentration of 100 μg/ml.

These transformants were inoculated into a test tube containing 10 ml of LB medium supplemented with 100 μg/ml of spectinomycin, and then cultured with shaking for 72 hours at 30° C.

After the culture was completed, the amount of CoQ8 produced by the transformants was calculated in the same manner as in Example 2 (1).

TABLE 6

CoQ8 Production by transformants of *Erwinia carotovora*

| Transformant | Cell amount (OD660) | Amount of CoQ8 Produced (mg/L) | Intracellular Content[*1] |
|---|---|---|---|
| IFO-3380/pEG400 | 1.68 | 0.26 | 1.5 |
| IFO-3380/pDXS-1 | 2.48 | 0.45 | 1.8 |

[*1]Intracellular content is shown with a value obtained by dividing a 10-fold CoQ8 production (mg/L) by a cell amount (OD660).

The amount of CoQ8 produced was significantly higher in IFO-3380/pDXS-1 than in the control strain IFO3380/pEG400.

EXAMPLE 5

Production of Ubiquinone and Carotenoids by Recombinant *Erwing uredovora*

The plasmids pUCYM-1, pQEDXS-1, pQEYM-1, obtained in Example 1, or pUC19 and pQE30 as controls were introduced into *Erwinia uredovora* DSM-30080 by electroporation, and then the transformants, E. uredovora DSM-30080/pUCYM-1, E. uredovora DSM-30080/pQEDXS-1, E. uredovora DSM-30080/pQEYM-1, E. uredovora DSM-30080/pUC19 and E. uredovora DSM-30080/pQE30, which showed resistant to ampicilin at a concentration of 100 μg/ml were obtained.

These transformants were inoculated into a test tube containing 10 ml of LB medium supplemented with 100 μg/ml of ampicillin, 1% glucose, vitamin $B_1$ and vitamin $B_6$, 100 mg/l each, and 50 mg/l of p-hydroxybenzoic acid. Then the transformants were cultured by shaking for 72 hours at 30° C.

After the culture was completed, the amount of CoQ8 produced by the transformants was calculated in the same manner as in Example 2 (1).

The produced amount of carotenoid pigments was calculated by detecting the absorbance at 450 nm for the 2-butanol layer using a spectrophotometer in the same manner as in Example 2 (1).

Table 7 shows the results.

TABLE 7

Production of CoQ8 and Carotenoids by transformants of E. uredovora

| Transformants | Cell amount OD660 | CoQ8 Production mg/L | CoQ8 Intracellular content ratio Relative value | Carotenoids Production Relative value | Carotenoids Intracellular content ratio Relative value |
|---|---|---|---|---|---|
| DSM-30080/pUC19 | 2.00 | 1.15 | 1.0 | 1.0 | 1.0 |
| DSM-30080/pUCYM-1 | 1.88 | 1.39 | 1.3 | 1.5 | 1.6 |
| DSM-30080/pQE30 | 2.52 | 1.29 | 1.0 | 1.0 | 1.0 |
| DSM-30080/pQEYM-1 | 1.92 | 1.36 | 1.4 | 1.7 | 2.2 |
| DSM-30080/pQEDXS-1 | 2.12 | 3.21 | 3.0 | 5.6 | 6.7 |

Both CoQ8 production and carotenoid pigment production were significantly higher in DSM-30080/pUCYM-1 than in the control strain DSM-30080/pUC19.

Similarly, both CoQ8 production and carotenoid pigment production were significantly higher in DSM-30080/pQEYM-1 and DSM-30080/pQEDXS-1 than in the control strain DSM-30080/pQE30.

EXAMPLE 6

Cloning of the DNA Encoding Proteins Involved in the Biosynthesis of Isoprenoid Compounds from a Photosynthetic Bacterium *Rhodobacter sphaeroides*

(1) Cloning of DXS Gene from *R. sphaeroides*

The Genbank database was searched for DXS homologue conserved in other species using the DXS nucleotide sequence found in *E.coli*. As a result, DXS homologues were found in *Haemophilus influenzae* (P45205), *Rhodobacter capsulatus* (P26242), *Bacillus subtilis* (P54523), *Synechocystis* sp. PCC6803 (P73067) and *Mycobacterium tuberculosis* (007184) and the like. Highly conserved amino acid sequences were selected by comparison of these sequences. A nucleotide sequence corresponding to such a conserved amino acid sequence was designed in consideration of the codon usuage in *R.sphaeroides*. A DNA fragment having a nucleotide sequence of SEQ ID NO:32 and of SEQ ID NO:33, and a DNA fragment having a nucleotide sequence of SEQ ID NO:34 were synthesized by DNA synthesizer.

PCR was carried out with DNA Thermal Cycler (Perkin Elmer Instruments, Inc. Japan) using chromosomal DNA of *R.sphaeroides* KY4113 (FERM-P4675) as a template, the primers above, and an Expand™ High-Fidelity PCR System (Boehringer Manheim K.K.).

PCR was carried out by 30 cycles, one cycle consisting of reaction at 94° C. for 40 seconds, reaction at 60° C. for 40 seconds, reaction at 72° C. for 1 minute, followed by reaction at 72° C. for 1 minute, thereby obtaining the DNA fragment of interest. The DNA fragments were DIG-labeled using DIG DNA Labeling Kit (Boehringer Manheim K.K.).

To obtain the full length DXS gene of *R.sphaeroides*, a genomic DNA library of a strain KY4113 was constructed. The strain KY4113 was cultured overnight in LB medium, extracting the chromosomal DNA. The chromosomal DNA was partially digested with a restriction enzyme Sau3AI, and then 4 to 6 kb DNA fragments were purified by sucrose density-gradient centrifugation. The DNA fragments were ligated with BamH I-digested vector pUC19 using a Ligation Pack (Nippon Gene), and *E.coli* DH5α was transformed using the ligated DNA. The transformants were spread on LB agar medium containing 100 μg/ml of ampicillin, thus obtaining about 10,000 colonies. As a result of screening by colony hybridization using the DIG-labeled DNA fragment as a probe, which had been obtained by the above method, two types of DNA fragments were detected. As a result of sequencing, ORF sharing high degrees of sequence homology with known DXS gene of other species was found from each DNA fragment. An amino acid sequence of SEQ ID NO:26 was named DXS1 and that of SEQ ID NO:27 was named DXS2.

(2) Confirmation of Complementarity Using *E.coli* DXS Gene-deleted Mutant

① Selection of *E.coli* DXS Gene-deleted Strain

*E.coli* W3110 (ATCC14948) was inoculated into LB liquid medium, and then cultured to its logarithmic growth phase. After culturing, cells were collected from the culture by centrifugation.

The cells were washed with 0.05 mol/l Tris-maleate buffer (pH 6.0) and suspended in the same buffer to a cell density of $10^9$ cells/ml.

NTG was added to the suspension to a final concentration of 600 mg/l, then the mixture was maintained for 20 minutes at room temperature to induce mutation.

The resultant NTG-treated cells were spread on a M9 minimum agar medium (Molecular Cloning, Second Edition) plate containing 0.1% 1-deoxyxylulose, then cultured. 1-Deoxyxylulose had been chemically synthesized according to the method described in J. C. S. Perkin Tans I, 2131–2137 (1982).

Colonies grew on M9 minimum agar medium containing 0.1% 1-deoxyxylulose were replicated on M9 minimal agar medium and on M9 minimal agar medium containing 0.1% 1-deoxyxylulose. The mutant of interest, a strain requiring 1-deoxyxylulose to grow, was selected. That is, a strain capable of growing on minimal agar medium containing 1-deoxyxylulose but not on the same medium lacking 1-deoxyxylulose was selected.

The thus selected and obtained mutant was named ME1. When pDXS-1 was introduced into the strain ME1, deficiency in 1-deoxyxylulose of the strain ME1 was complemented. Therefore the strain ME1 was confirmed to be a strain from which DXS gene was deleted.

(3) Complementation Studies on DXS1 and DXS2

DNA fragment encoding DXS1 of SEQ ID NO:27 or a DNA fragment encoding DXS2 of SEQ ID NO:29, respectively, both derived from the strain KY4113, was ligated to downstream of the lac promoter of a vector pUC19 respectively to construct recombinant plasmids.

When the constructed plasmids were introduced into the strain ME1, both DXS 1 and DXS 2 each complemented the 1-deoxyxylulose-deficiency in the strain ME 1.

Therefore, *R. sphaeroides* was shown to have two genes, DXS1 and DXS2, having activity to catalyze the reaction to produce 1-deoxy-D-xylulose 5-phosphate from pyruvic acid and glyceraldehyde 3-phosphate.

(4) Cloning of Gene Complementing Methylerythritol-requiring Nature Derived from *R. sphaeroides*

The *E.coli* Methylerythritol-requiring mutant ME7 obtained in Example 1 (2) ① was inoculated into LB liquid medium containing 0.1% methylerythritol, cultured to its logarithmic growth phase, then centrifuged to collect cells.

The cells were washed twice with 1 mol/l HEPES aqueous solution containing 10% glycerol so as to remove the medium components as far as possible.

Plasmids were extracted from the genomic library of *R. sphaeroides* KY4113 constructed in Example 6 (1). Then the plasmids were introduced into the washed cells by electroporation according to standard techniques.

Next, the cells were spread on LB agar medium containing 100 μg/l of ampicillin, then cultured overnight at 37° C.

After picking up the colonies grown on the medium, the colonies were inoculated into LB liquid medium to culture, then plasmids were extracted from the cells cultured.

When the plasmids extracted were introduced again into the strain ME 7, the transformants could grow in a medium lacking methylerythritol. Therefore it was confirmed that the plasmid contained a DNA fragment complementing methylerythritol-requiring nature derived from *R. sphaeroides*.

As a result of sequencing of the nucleotide sequence of the DNA fragment, the DNA sequence of SEQ ID NO:31 encoding an amino acid sequence that shares high homology with *E.coli* yaeM was found.

EXAMPLE 7

Production of Ubiquinone-10 (CoQ10) by Recombinant Photosynthetic Bacteria

A glnB promoter derived from the strain KY4113 was ligated upstream of the DNA fragment DXS1 of SEQ ID NO:27 and DXS2 of SEQ ID NO:29, both obtained in Example 6. Then the product was inserted into a broad host range vector pEG400, thus constructing plasmids. These plasmids were named pRSDX-1 and pRSDX-2, respectively. In addition, yaeM and DXS1 were joined in tandem, then the product was ligated downstream of glnB promoter, thereby constructing a plasmid. The plasmid was named pRSYMDX1. These plasmids were introduced into *R. sphaeroides* KY4113, respectively, by electroporation (Bio-Rad Laboratories).

Then the cells were spread on LB agar medium containing spectinomycin at a concentration of 100 μg/ml, then cultured for 3 days at 30° C.

Next, colonies that grew on the medium were inoculated into LB medium containing spectinomycin at a concentration of 100 μg/ml, cultured overnight Then, the cultured cells were collected by centrifugation.

It was confirmed that the cells of each strain contained the introduced plasmid by extracting the plasmids from the cells (Qiagen, Inc). Thus obtained transformants were named KY4113/pRSDX-1, KY4113/pRSDX-2, KY4113/pRSYMDX1 and KY4113/pEG400.

A platinum loop of each transformant was inoculated into a test tube containing 5 ml of seed medium (2% glucose, 1% peptone, 1% yeast extract, 0.5% NaCl, pH 7.2 adjusted with NaOH) and then cultured for 24 hours at 30° C. 0.5 ml of the resultant culture was inoculated into a test tube containing 5 ml of ubiquinone-10 production medium, then cultured by shaking for 5 days at 30° C. The ubiquinone-10 production medium consisted of 4% blackstrap molasses, 2.7% glucose, 4% com steep liquor, 0.8% ammonium sulfate, 0.05% potassium primary phosphate, 0.05% potassium secondary phosphate, 0.025% magnesium sulfate heptahydrate, 3 mg/l of ferrous sulfate heptahydrate, 8 mg/l of thiamine, 8 mg/l of nicotinic acid, and 1 ml/l of trace element, had previously been adjusted to pH 9, supplemented with 1% calcium carbonate, then autoclaved.

Then the amount of CoQ10 produced by the transformants was calculated in the same manner as in quantification of CoQ8 in Example 2 (1). Table 8 shows the results.

TABLE 8

|  | Cell amount [OD660] | Amount of CoQ10 Accumulated [mg/l] |
| --- | --- | --- |
| KY4113/pEG400 | 23.7 | 65.2 |
| KY4113/pRSDX-1 | 23 | 81 |
| KY4113/pRSDX-2 | 24.4 | 81.9 |
| KY4113/pRSYMDX1 | 25.8 | 117.9 |

The amount of COQ10 produced was significantly higher in KY4113/pRSDX-1, KY4113/pRSDX-2 and KY4113/pRSYMDX1 than in the control strain KY4113/pEG400.

EXAMPLE 8

Determination of the Activity of the Enzyme Encoded by yaeM Gene (1) Overexpression of yaeM Gene A recombinant plasmid that can express yaeM gene sufficiently was constructed using PCR [Science, 230, 1350 (1985)], as follows.

A sense primer having a nucleotide sequence of SEQ ID NO:24 and an antisense primer having a nucleotide sequence of SEQ ID NO:25 were synthesized using a DNA synthesizer.

A restriction enzyme BamH I site was added to each of 5'-ends of the sense and antisense primers. yaeM gene was amplified by PCR using chromosomal DNA of *E.coli* as a template, these primers, Taq DNA polymerase (Boehringer), and DNA Thermal cycler (Perkin Elmer Japan).

PCR was carried out by 30 cycles, one cycle consisting of reaction at 94° C. for 30 seconds, reaction at 55° C. for 30 seconds, and reaction at 72° C. for 2 minutes followed by reaction at 72° C. for 7 minutes.

The amplified DNA fragments and pUC118 (TAKARA SHUZO Co., Ltd.) were digested with a restriction enzyme BamH I, then each DNA fragment was purified by agarose gel electrophoresis.

Both purified fragments were mixed together, then treated with ethanol, allowing DNA to precipitate. The resultant DNA precipitate was dissolved in 5 μl of distilled water for ligation reaction to occur, thereby obtaining recombinant DNA.

The recombinant DNA was confirmed to be yaeM gene by determining its DNA sequence.

Plasmids were extracted from the microorganism having the recombinant DNA, digested with a restriction enzyme BamH I, and subjected to agarose gel electrophoresis, thereby obtaining DNA fragments containing BamH I-treated yaeM gene.

pQE30 (Qiagen, Inc) was digested with a restriction enzyme BamH I, then subjected to agarose gel electrophoresis, thereby obtaining BamH I-treated pQE30 fragments.

The resultant DNA fragments containing BamH I-treated yaeM gene were mixed with BamH I-digested pQE30 fragments, and treated with ethanol for DNA to precipitate. The DNA precipitate was dissolved in 5 μl of distilled water for ligation reaction to occur, thereby obtaining recombinant DNA.

*E. coli* JM109 was transformed using the recombinant DNA by standard techniques. Then the transformants were spread on LB agar medium containing 100 μg/ml of ampicillin, then cultured overnight at 37° C.

Plasmids were isolated from the *E.coli* in the same manner as described above.

Similarly, the isolated plasmid was cleaved with various restriction enzymes to examine the structure, then the nucleotide sequence was determined, thereby confirming the plasmids contained the DNA fragments of interest. The plasmid was named pQEDXR.

(2) Determination of Activity of yaeM Gene Product

① Purification of yaeM Gene Product

The pQEDXR constructed in (1) was introduced into E.coli M15 (Qiagen. Inc) having pREP4 by standard techniques, and a strain M15/pREP4+pQEDXR resistant to 200 μg/ml of ampicillin and 25 μg/ml of kanamycin was obtained.

The stain M15/pREP4+pQEDXR was cultured at 37° C. in 100 ml of LB liquid medium containing 200 μg/ml of ampicillin and 25 μg/ml of kanamycin. When the turbidity at 660 nm reached 0.8, isopropyl thiogalactoside was added to a final concentration of 0.2 mol/l. Subsequently, the strain was cultured for 5 hours at 37° C., then the supernatant of the culture was removed by centrifugation (3000 rpm, 10 minutes). The cells were suspended in 6 ml of 100 mol/l Tris-hydrochloric acid buffer (pH 8.0), then disrupted using a ultrasonicator (SONIFIER, BRANSON) while cooling with ice. The obtained cell-disrupted solution was centrifuged at 10,000 rpm for 20 minutes at 4° C., thereby collecting the supernatant The supernatant centrifuged from the cellular extract was introduced into a Ni-NTA resin column (Qiagen. Inc), then washed with 20 ml of a washing buffer (100 mol/l Tris-hydrochloric acid (pH 8.0), 50 mol/l imidazole, 0.5% Tween 20). Then 10 ml of an elution buffer (100 mol/l Tris-hydrochloric acid (pH 8.0), 200 mol/l imidazole) was introduced into the column, thus fractionating the eluate into 1 ml each.

Protein amounts for each fraction were measured using a kit for quantifying protein amount (Bio-Rad Laboratories), thus obtaining a fraction containing proteins as a purified protein fraction.

② Preparation of a Substrate, 1-deoxy-D-xylulose 5-phosphate

A reaction substrate, 1-deoxy-D-xylulose 5-phosphate was prepared as described below. 1-Deoxy-D-xylulose 5-phosphate was detected by measuring the absorbance at 195 nm using HPLC [Column: Senshu pak NH2-1251-N (4.6×250 mm, Senshu), mobile phase: 100 mol/l $KH_2PO_4$ (pH 3.5)].

The plasmid pQDXS-1 that allows overexpression of E.coli dxs gene was introduced into E.coli M15/pREP4 in the same manner as described above, obtaining a strain M15/pREP4+pQDXS-1.

This strain was cultured in the same way as in Example 8 (2)①, then dxs protein was purified using Ni-NTA resin column.

The purified dxs protein was added to a 20 ml of reaction solution [100 mol/l Tris-hydrochloric acid (pH 7.5), 10 mol/l sodium pyruvate, 30 mol/l DL-glyceraldehyde-3-phosphate, 1.5 mol/l thiamine pyruvate, 10 mol/l $MgCl_2$, 1 mol/l DL-dithiothreitol] then maintained at 37° C.

After reacting for 12 hours, the reaction solution was diluted with water to 300 ml, introduced into an activated carbon column (2.2×8 cm) followed by a Dowex 1-X8 (C1-type, 3.5×25 cm), then eluted with 1% saline solution. After the eluted fraction was concentrated, the fraction was introduced into Sephadex G-10 (1.8×100 cm), then eluted with water. Finally fractions containing 1-deoxy-D-xylulose 5-phosphate were freeze-dried, thereby obtaining about 50 mg of white powder This powder was confirmed to be 1-deoxy-D-xylulose 5-phosphate by NMR analysis (A-500, JEOL Ltd.).

③ Determination of Enzymatic Activity of yaeM Gene Product 0.3 mol/l of 1-deoxy-D-xylulose 5-phosphate (final concentration) synthesized as described above was added to 1 ml of a reaction solution containing 100 mol/l Tris-hydrochloric acid (pH 7.5), 1 mol/l $MmCl_2$, 0.3 mol/l NADPH and yaeM gene product obtained in Example 8 (2)①, and then incubated at 37° C. The increase and decrease in NADPH during incubation was traced by reading the absorbance at 340 nm using a spectrophotometer (UV-160, SHIMADZU CORP.), suggesting that NADPH decreased with time.

To confirm the structure of the reaction product, the reaction was carried out similarly, but on a larger scale, thus isolating the product 200 ml of a reaction solution with a composition the same as that described above except that the concentration of 1-deoxy-D-xylulose 5-phosphate was 0.15 mol/l, was incubated for 30 minutes at 37° C. Then the whole amount of the reaction solution was added to an activated carbon column, diluted with water to 1 L, then added to a Dowex 1-X8 (C1-type, 3.5×20 cm) column.

The solution was eluted with 400 ml of 1% saline solution, added to a Sephadex G-10 (1.8×100 cm), then eluted with water. The eluted fraction was freeze-dried, thereby isolating the reaction product.

The molecular formula of the reaction product isolated from HR-FABMS analysis was assumed to be $C_5H_{12}O_7P$ [m/z 215.0276 (M-H)$^-$, Δ−4.5 mmu]. NMR analysis for $^1H$ and $^{13}C$ resulted in the following chemical shifts.

$^1H$ NMR ($D_2O$, 500 MHz): δ 4.03 (ddd, J=11.5,6.5,2.5 Hz, 1H), 3.84 (ddd, J=11.5, 8.0, 6.5 Hz, 1H), 3.78 (dd, J=80, 2.5 Hz, 1H), 3.60 (d, J=12.0 Hz, 1H), 3.50 (d, J=12.0 Hz, 1H), 1.15 (s, 3H); $^{13}C$ NMR ($D_2O$, 125 MHz): δ75.1 (C-2), 74.8 (C-3), 67.4 (C-1), 65.9 (C-4), 19.4 (2-Me)

The chemical shifts resulted from NMR analysis for $^1H$ and $^{13}C$ of compounds obtained by treating the reaction products with alkaline phosphatase (TAKARA SHUZO CO., LTD.) were completely identical with that resulted from NMR analysis of 2-C-methyl-D erythritol synthesized in the method described in Tetrahedron Letter, 38, 6184 (1997).

Further the angle of rotation of the former compound was $[α]_D^{21}=+6.0$ (c=0.050, $H_2O$), identical with the angle of rotation $[α]_D^{25}=+7.0$ (c=0.13, $H_2O$) of 2-C-methyl-D-erythritol, reported in Tetrahedron Letter, 38, 6184 (1997).

These results reveal that the reaction product of yaeM gene product was 2-C-methyl-D-erythritol 4-phosphate. That is, yaeM gene product was found to have activity to yield 2-C-mehyl-D-erythritol 4-phosphate from 1-deoxy-D-xylulose 5-phosphate with consumption of NADPH. Based on this catalytic activity, this enzyme was named 1-deoxy-D-xylulose 5-phosphate reductoisomerase.

④ Characteristics of 1-deoxy-D-xylulose 5-phosphate Reductoisomerase

The enzymological characteristics of 1-deoxy-D-xylulose 5-phosphate reductoisomerase were examined using 1 ml of the reaction system as described in Example 8 (2) ③. Here, 1 unit is defined as the activity to oxidize 1 mmol of NADPH per a minute.

The activity decreased below 1/100 when NADPH was replaced with NADH.

No reaction occurred when 1-deoxy-D-xylulose was used instead of 1-deoxy-D-xylulose 5-phosphate.

SDS-PAGE analysis showed that this enzyme was consisted of 42 kDa polypeptide.

Table 9 shows effect on the reaction system by the addition of metals.

TABLE 9

Effect of various metal ions on the activity of 1-deoxy-D-xylulose 5-phosphate reductoisomerase

| Additives | Specific Activity (units/mg protein) |
|---|---|
| none | 0.3 |
| EDTA | N.D. |
| $MnCl_2$ | 11.8 |
| $CoCl_2$ | 6.0 |
| $MgCl_2$ | 4.0 |
| $CaCl_2$ | 0.2 |
| $NiSO_4$ | 0.2 |
| $ZnSO_4$ | 0.3 |
| $CuSO_4$ | N.D. |
| $FeSO_4$ | N.D. |

These metal ions and EDTA were added such that the concentration of each was 1 mol/l. N.D. indicates that no activity was detected.

Km for 1-deoxy-D-xylulose 5-phosphate and NADP in the presence of $MnCl_2$ were 249 µmol/l and 7.4 µmol/l, respectively.

Figure 2:
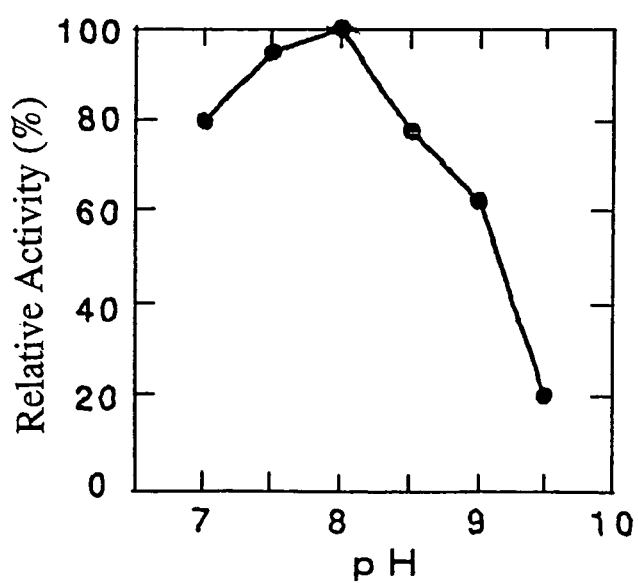
FIG. 2 shows the effect of the pH of the reaction solution on 1-deoxy-D-xylulose 5-phosphate reductoisomerase activity. Enzymatic activity measured at various pH in 100 mol/l Tris-hydrochloric acid buffer are shown. Activity is shown as a relative activity when activity at pH 8.0 is considered as 100%.

FIG. 1 shows the effect of reaction temperature and FIG. 2 shows the effect of reaction pH.

EXAMPLE 9

Construction and Characteristics of yaeM-Deleted Mutant (1) Construction of yaeM-Disrupted Mutant To test whether 1-deoxy-D-xylulose 5-phosphate reductoisomerase is essential for cell growth or not, a 1-deoxy-D-xylulose 5-phosphate reductoisomerase-deleted mutant was constructed as described below.

A kanamycin-resistant gene cassette for insertion into yaeM gene was produced as described below.

The plasmid pMEW41 obtained in Example 1 (2) ② was digested with a restriction enzyme Bal I, and was subjected to agarose gel electrophoresis, thereby obtaining a Bal I-treated DNA fragment Tn5 was digested with restriction enzymes Hind III and Sam I, then the both ends were blunt-ended using a DNA blunting kit (TAKARA SHUZO CO., LTD.).

The resultant blunt-ended DNA fragments were mixed with previously obtained Bal I-treated pMEW41DNA fragments, and then the mixture was treated with ethanol. Next the obtained DNA precipitate was dissolved into 5 µl of distilled water for ligation reaction to occur, thereby obtaining recombinant DNA.

*E. coli* JM109 (purchased from TAKARA SHUZO CO., LTD.) was transformed using this recombinant DNA according to standard techniques. Next the transformant was spread on LB agar medium containing 100 µg/ml of ampicillin and 15 µg/ml of kanamycin, then cultured overnight at 37° C.

Several ampicilin-resistant transformant colonies grown on the medium were shake-cultured for 16 hours at 37° C. in 10 ml of LB liquid medium containing 100 µg/ml of ampicilin and 15 µg/ml of kanamycin.

The resulting culture was centrifuged to collect cells.

Plasmids were isolated from the cells according to the standard techniques.

Figure 3:
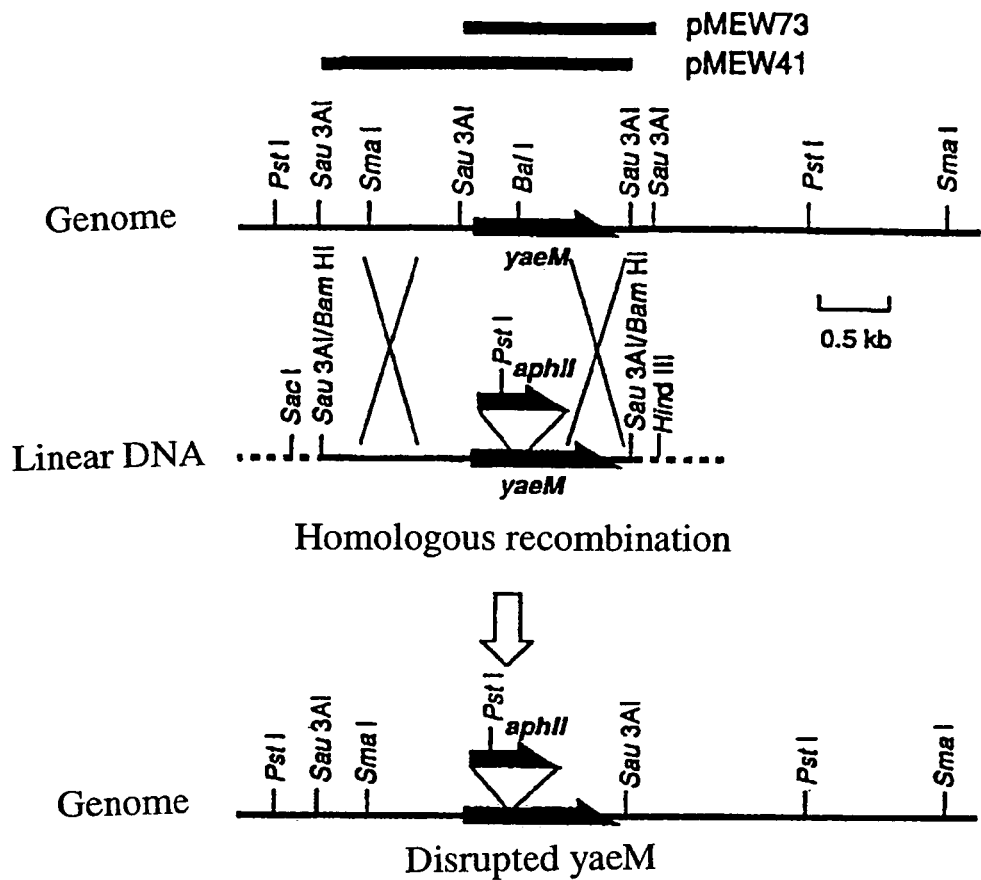
FIG. 3 shows a method for disrupting yaeM gene on a chromosome using homologous recombination.

The plasmids isolated as described above were cleaved with various restriction enzymes to test their structure. As a result, the plasmid was confirmed to contain the DNA fragment of interest and was named pMEW41Km. yaeM gene on a chromosomal DNA of *E.coli* was disrupted by homologous recombination using pMEW41Km. FIG. 3 shows the schematic diagram for this recombination. pMEW41Km was digested with restriction enzymes Hind III and Sac I, subjected to agarose gel electrophoresis, thus purifying linear fragments. *E.coli* FS1576 was transformed using the fragments according to standard techniques. The strain FS1576 is available as the strain ME9019 from National Institute of Genetics. The transformants were spread on LB agar medium containing 15 µg/ml of kanamycin and 1 g/l of 2C-methyl-D-erythritol, then cultured overnight at 37° C.

Several kanamycin-resistant colonies that grew on the medium were shake cultured for 16 hours at 37° C. in 10 ml of LB liquid medium containing 15 µg/ml of kanamycin and 1 g/l of 2-C-methyl-D-erythritol.

The resulting culture was centrifuged to collect cells.

Chromosomal DNA was isolated from the cells by the standard techniques.

The chromosomal DNA was digested with a restriction enzyme Sma I or Pst I. Chromosomal DNA of the strain FS1576 was digested with a restriction enzyme in the same way. These DNAs digested with restriction enzymes were subjected to agarose gel electrophoresis by the standard techniques, and then to Southern hybridization analysis using the kanamycin-resistant gene and yaeM gene as probes. Therefore, it was confirmed that the chromosomal DNA of the kanamycin-resistant colonies had a structure as shown in FIG. 3, that is, yaeM gene was disrupted by the kanamycin-resistant gene.

(2) Characteristics of yaeM-Disrupted Mutant

The yaeM-disrupted strain produced as described above and its parent strain FS1576 were spread on LB agar medium and the same medium containing 1 g/l of 2-C-methyl-D-erythritol, then cultured at 37° C. Table 10 shows the cell growth after 2 days of culture.

TABLE 10

Effect of deletion of yaeM gene on the *E. coli* growth

| | Cell growth on each medium[*1] | |
|---|---|---|
| Strain | LB | LB + ME[*2] |
| FS1576 | + | + |
| yaeM-deleted strain | − | + |

[*1]Cell growth (+ indicates good growth; − indicates no growth)
[*2]ME indicates the addition of 1 g/l of 2-C-methyl-D-erythritol.

No yaeM-deleted mutants grew on a medium lacking 2-C-methyl-D-erythritol. Therefore, This gene was shown to be essential for the cell growth in the absence of 2-C-methyl-D-erythritol.

EXAMPLE 10

Effect of 1-deoxy-D-xylulose 5-phosphate Reductoisomerase Inhibitor for Cell Growth The following experiments were conducted based on the assumption that fosmidomycin could inhibit 1-deoxy-D-xylulose 5-phosphate reductoisomerase because 2-C-methyl-D-erythritol 4-phosphate, a product from 1-deoxy-D-xylulose 5-phosphate reductoisomerase reaction, or reaction intermediates expected to be produced in this enzyme reaction is structurally analogous to fosmidomycin.

In the presence of fosmidomycin, the activity 1-deoxy-D-xylulose 5-phosphate reductoisomerase was measured by the method as described in Example 8 in order to examine the effect on the enzymatic activity.

Fosmidomycin had been synthesized according to the method described in Chem. Pharm. Bull., 30, 111–118 (1982).

Total volume of reaction solution was reduced to 0.2 ml from the volume of reaction solution described in Example 8 (2), but each concentration was kept at the same level as the system of Example 8 ③. Fosmidomycin at various concentration was added to the reaction solution, then the reaction was carried out at 37° C. The increase and decrease in NADPH were measured using Bench mark micro plate reader (Bio-Rad Laboratories).

Figure 4:
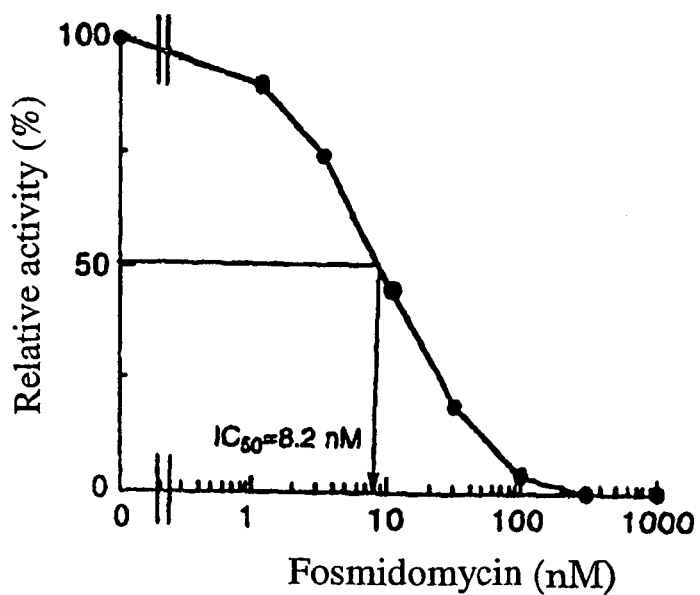
FIG. 4 shows the effect of fosmidomycin on 1-deoxy-D-xylulose 5-phosphate reductoisomerase.

As shown in FIG. 4, fosmidomycin was shown to inhibit 1-deoxy-D-xylulose 5-phosphate reductoisomerase.

E. coli W3110 was spread on LB agar medium, the same medium containing 3.13 mg/l of fosmidomycin, and the same medium containing 3.13 mg/l of fosmidomycin and 0.25 g/l of 2-C-methyl-D-erythritol, then cultured at 37° C.

Two days after culturing, the microorganism could grow on the two types of media, that is, the LB agar medium and the same medium containing fosmidomycin and 0.25 g/l of 2C-methyl-D-erythritol, but no microorganism grew on the LB agar medium supplemented only with fosmidomycin.

These results clearly shows that fosmidomycin inhibited the cell growth by inhibiting 1-deoxy-D-xylulose 5-phosphate reductoisomerase. Accordingly, a substance inhibiting yaeM gene product (1-deoxy-D-xylulose 5-phosphate reductoisomerase) activity can be an effective antibiotic agent or herbicide.

All publications, patents and patent applications cited herein are incorporated herein by reference in their entity.

INDUSTRIAL APPLICABILITY

The present invention can provide a process for producing isoprenoid compounds comprising integrating DNA into a vector wherein the DNA contains one or more DNA involved in biosynthesis of isoprenoid compounds useful in pharmaceuticals for cardiac diseases, osteoporosis, homeostasis, prevention of cancer, and immunopotentiation, health food and anti-fouling paint products against barnacles, introducing the resultant recombinant DNA into a host cell derived from prokaryote, culturing the obtained transformants in a medium, allowing the transformant to produce and accumulate isoprenoid compounds in the culture, and recovering the isoprenoid compounds from the culture; a process for producing a protein having activity to improve efficiency in the biosynthesis of isoprenoid compounds comprising integrating DNA containing one or more DNA encoding the protein into a vector, introducing the resultant recombinant DNA into a host cell, culturing the obtained transformant in a medium, allowing the transformant to produce and accumulate said protein in the culture, and recovering said protein from the culture; the protein; and novel enzymatic protein having activity to catalyze a reaction to produce 2-C-methyl-D-erythritol 4-phosphate from 1-deoxy-D-xylulose 5-phosphate; and a method for screening a compound with antibiotic and/or weeding activity comprising screening a substance inhibiting the enzyme.

Sequence Listing Free Text

SEQ ID NO: 12: synthetic DNA
SEQ ID NO: 13: synthetic DNA
SEQ ID NO: 14: synthetic DNA
SEQ ID NO: 15: synthetic DNA
SEQ ID NO: 16: synthetic DNA
SEQ ID NO: 17: synthetic DNA
SEQ ID NO: 18: synthetic DNA
SEQ ID NO: 19: synthetic DNA
SEQ ID NO: 20: synthetic DNA
SEQ ID NO: 21: synthetic DNA
SEQ ID NO: 22: synthetic DNA
SEQ ID NO: 23: synthetic DNA
SEQ ID NO: 24: synthetic DNA
SEQ ID NO: 25: synthetic DNA
SEQ ID NO: 32: synthetic DNA
SEQ ID NO: 33: synthetic DNA
SEQ ID NO: 34: synthetic DNA

The invention claimed is:

1. A process for producing an isoprenoid compound comprising the steps of:
   introducing a vector containing DNA encoding a protein comprising an amino acid sequence of SEQ ID NO:5 into a prokaryotic host cell to produce a transformant;
   culturing the transformant in a medium;
   allowing the transformant to produce and accumulate the isoprenoid compound; and
   recovering the isoprenoid compound.

2. A process for producing an isoprenoid compound comprising the steps of:
   culturing a prokaryotic transformant harboring a vector containing DNA encoding a protein comprising an amino acid sequence of SEQ ID NO:5 in a medium;
   allowing the transformant to produce and accumulate the isoprenoid compound; and
   recovering the isoprenoid compound.

3. The process according to claim 1 or 2, wherein the DNA comprises a nucleotide sequence of SEQ ID NO:10.

4. The process according to claim 1 or 2, wherein the isoprenoid compound is selected from the group consisting of ubiquinone, vitamin $K_2$ and carotenoid.

5. The process according to claim 3, wherein the isoprenoid compound is selected from the group consisting of ubiquinone, vitamin $K_2$ and carotenoid.

6. A process for producing an isoprenoid compound comprising the steps of:
   introducing a vector containing DNA which hybridizes with a nucleotide sequence consisting of SEQ ID NO:10 in the presence of 0.7 to 1.0 mol/l NaCl at 65° C. followed by washing in a 0.1 to 2-fold SSC solution at 65° C. and encodes a protein having activity to catalyze a reaction to produce 2-C-methyl-D-erythritol 4-phosphate from 1-deoxy-D-xylulose 5-phosphate into a prokaryotic host cell to produce a transformant;
   culturing the transformant in a medium;
   allowing the transformant to produce and accumulate the isoprenoid compound; and
   recovering the isoprenoid compound.

7. A process for producing an isoprenoid compound comprising the steps of:
   culturing a prokaryotic transformant harboring a vector containing DNA that hybridizes with a nucleotide sequence consisting of SEQ ID NO:10 in the presence of 0.7 to 1.0 mol/l NaCl at 65° C. followed by washing in a 0.1 to 2-fold SSC solution at 65° C. and encodes a protein having activity to catalyze a reaction to produce 2-C-methyl-D-erythritol 4-phosphate from 1-deoxy-D-xylulose 5-phosphate in a medium;
   allowing the transformant to produce and accumulate the isoprenoid compound; and
   recovering the isoprenoid compound.

8. The process according to claim 6 or 7, wherein the isoprenoid compound is selected from the group consisting of ubiquinone, vitamin $K_2$ and carotenoid.

* * * * *